United States Patent
Larsen et al.

(10) Patent No.: US 10,329,283 B2
(45) Date of Patent: Jun. 25, 2019

(54) G PROTEIN-COUPLED RECEPTOR KINASE INHIBITORS AND METHODS FOR USE OF THE SAME

(71) Applicant: THE REGENTS OF THE UNIVERSITY OF MICHIGAN, Ann Arbor, MI (US)

(72) Inventors: Scott D. Larsen, South Lyon, MI (US); John J. G. Tesmer, Ann Arbor, MI (US); Helen Waldschmidt, Ann Arbor, MI (US); Kristoff Homan, Newton, MA (US); Michael William Wilson, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/738,606

(22) PCT Filed: Jun. 27, 2016

(86) PCT No.: PCT/US2016/039526
§ 371 (c)(1),
(2) Date: Dec. 21, 2017

(87) PCT Pub. No.: WO2016/210403
PCT Pub. Date: Dec. 29, 2016

(65) Prior Publication Data
US 2018/0186779 A1    Jul. 5, 2018

Related U.S. Application Data

(60) Provisional application No. 62/185,242, filed on Jun. 26, 2015.

(51) Int. Cl.
| | |
|---|---|
| C07D 405/14 | (2006.01) |
| C07D 401/14 | (2006.01) |
| C07D 401/12 | (2006.01) |
| C07D 405/12 | (2006.01) |
| A61P 9/00 | (2006.01) |
| A61P 9/12 | (2006.01) |

(52) U.S. Cl.
CPC ........... *C07D 405/14* (2013.01); *A61P 9/00* (2018.01); *A61P 9/12* (2018.01); *C07D 401/12* (2013.01); *C07D 401/14* (2013.01); *C07D 405/12* (2013.01)

(58) Field of Classification Search
CPC .................................................. C07D 405/14
See application file for complete search history.

(56) References Cited

U.S. PATENT DOCUMENTS

| | | |
|---|---|---|
| 2007/0099944 A1 | 5/2007 | Drewry |
| 2010/0022585 A1 | 1/2010 | deLong et al. |
| 2011/0245245 A1 | 10/2011 | Mortensen et al. |

FOREIGN PATENT DOCUMENTS

WO    WO-2007/034846 A1    3/2007

OTHER PUBLICATIONS

No new references cited by the Examiner.*
Benovic et al., Inhibition of the beta-adrenergic receptor kinase by polyanions, *J. Biol. Chem.*, 264(12):6707-10 (1989).
Benovic et al., Beta-adrenergic receptor kinase: primary structure delineates a multigene family, *Science*, 246(4927):235-40 (1989).
Chen et al., Myocardial function in hearts with transgenic overexpression of the G protein-coupled receptor kinase 5, *Annals of Thoracic Surgery*, 71(4):1320-4 (2001).
Claing et al., Endocytosis of G protein-coupled receptors: roles of G protein-coupled receptor kinases and beta-arrestin proteins, *Prog. Neurobiol.*, 66(2):61-79 (2002).
Diviani et al., Effect of different G protein-coupled receptor kinases on phosphorylation and desensitization of the alpha1B-adrenergic receptor, *J. Biol. Chem.*, 271(9):5049-58 (1996).
Eschenhagen, Beta-adrenergic signaling in heart failure-adapt or die, *Nat. Med.*, 14(5):485-7 (2008).
Gold et al., Nuclear translocation of cardiac G protein-Coupled Receptor kinase 5 downstream of select Gq-activating hypertrophic ligands is a calmodulin-dependent process, *PLoS One*, 8(3):e57324 (2013).
Gurevich et al., The structural basis of arrestin-mediated regulation of G-protein-coupled receptors, *Pharmacol. Ther.*, 110:465-502 (2006).
Gurevich et al., G protein-coupled receptor kinases: more than just kinases and not only for GPCRs, *Pharmacol. Ther.*, 133:40-69 (2012).
Hata et al., Genetic manipulation of myocardial beta-adrenergic receptor activation and desensitization, *J. Mol. Cell. Cardiol.*, 37:11-21 (2004).
Hausdorff et al., Two kinases mediate agonist-dependent phosphorylation and desensitization of the beta 2-adrenergic receptor, *Symp. Soc. Exp. Biol.*, 44:225-40 (1990).
Homan et al., Identification and structure-function analysis of subfamily selective G protein-coupled receptor kinase inhibitors, *ACS Chem. Biol.*, 10:310-9 (2015).

(Continued)

*Primary Examiner* — Shawquia Jackson
(74) *Attorney, Agent, or Firm* — Marshall, Gerstein & Borun LLP

(57) ABSTRACT

Disclosed herein are novel GRK inhibitors and methods for their use in treating or preventing heart disease, such as cardiac failure, cardiac hypertrophy, and hypertension. In particular, disclosed herein are compounds of Formula (I) and pharmaceutically acceptable salt thereof, wherein the substituents are as described.

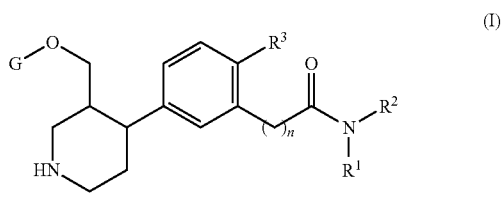

20 Claims, No Drawings

(56) References Cited

OTHER PUBLICATIONS

Homan et al., Identification and characterization of amlexanox as a G protein-coupled receptor kinase 5 inhibitor, *Molecules*, 19(10):16937-49 (2014).
Koch et al., Cardiac function in mice overexpressing the beta-adrenergic receptor kinase or a beta ARK inhibitor, *Science*, 268(5215):1350-3 (1995).
Kunapuli et al., Expression, purification, and characterization of the G protein-coupled receptor kinase GRK5, *J. Biol. Chem.*, 269(2):1099-105 (1994).
Lefkowitz et al., Role of phosphorylation in desensitization of the beta-adrenoceptor, *Trends Pharmacol. Sci.*, 11(5):190-4 (1990).
Lino et al., Rational Design and Evaluation of New Lead Compound Structures for Selective βARK1 Inhibitors, *J. Med. Chem.*, 45:2150-9 (2002).
Lymperopoulos, Beta-arrestin biased agonism/antagonism at cardiovascular seven transmembrane-spanning receptors, *Curr. Pharm Des.*, 18(2):192-8 (2012).
Lymperopoulos et al., Reduction of sympathetic activity via adrenal-targeted GRK2 gene deletion attenuates heart failure progression and improves cardiac function after myocardial infarction, *J. Biol. Chem.*, 285(21):16378-86 (2010).
Martini et al., Uncovering G protein-coupled receptor kinase-5 as a histone deacetylase kinase in the nucleus of cardiomyocytes, *Proc. Natl. Acad. Sci. USA*, 105(34):12457-62 (2008).
Palczewski et al., Rhodopsin kinase: substrate specificity and factors that influence activity, *Biochemistry*, 27(7):2306-13 (1988).
Pitcher et al., G protein-coupled receptor kinases, *Annu. Rev. Biochem.*, 67:653-92 (1998).
Raake et al., G protein-coupled receptor kinase 2 ablation in cardiac myocytes before or after myocardial infarction prevents heart failure, *Circ. Res.*, 103(4):413-22 (2008).
Raake et al., AAV6.βARKct cardiac gene therapy ameliorates cardiac function and normalizes the catecholaminergic axis in a clinically relevant large animal heart failure model, *Eur Heart J.*, 34(19): 1437-47 (2012).
Reiter et al., Molecular mechanism of β-arrestin-biased agonism at seven-transmembrane receptors, *Annu. Rev. Pharmacol. Toxicol.*, 52:179-97 (2012).
Rengo et al., Myocardial adeno-associated virus serotype 6-betaARKct gene therapy improves cardiac function and normalizes the neurohormonal axis in chronic heart failure, *Circulation*, 119:89-98 (2009).
Rockman et al., Receptor-specific in vivo desensitization by the G protein-coupled receptor kinase-5 in transgenic mice, *Proc. Natl. Acad. Sci. USA*, 93(18):9954-9 (1996).
Rockman et al., Expression of a beta-adrenergic receptor kinase 1 inhibitor prevents the development of myocardial failure in gene-targeted mice, *Proc. Natl. Acad. Sci. USA*, 95(12):7000-5 (1998).
Setyawan et al., Inhibition of protein kinases by balanol: specificity within the serine/threonine protein kinase subfamily, *Mol. Pharmacol.*, 56(2):370-6 (1999).
Shah et al., In vivo ventricular gene delivery of a beta-adrenergic receptor kinase inhibitor to the failing heart reverses cardiac dysfunction, *Circulation*, 103(9):1311-6 (2001).
Tesmer et al., Structure of human G protein-coupled receptor kinase 2 in complex with the kinase inhibitor balanol, *J. Med. Chem.*, 53(4):1867-70 (2010).
Thal et al., Paroxetine is a direct inhibitor of g protein-coupled receptor kinase 2 and increases myocardial contractility, *ACS Chemical Biology*, 7(11):1830-9 (2012).
Thal et al., Molecular mechanism of selectivity among G protein-coupled receptor kinase 2 inhibitors, *Mol. Pharmacol.*, 80(2):294-303 (2011).
Ungerer, Expression of beta-arrestins and beta-adrenergic receptor kinases in the failing human heart, *Circ. Res.*, 74(2):206-13 (1994).
Ungerer, Altered expression of beta-adrenergic receptor kinase and beta 1-adrenergic receptors in the failing human heart, *Circulation*, 87(2):454-63 (1993).
Vinge et al., Substrate specificities of g protein-coupled receptor kinase-2 and -3 at cardiac myocyte receptors provide basis for distinct roles in regulation of myocardial function, *Mol. Pharmacol.*, 72(3):582-91 (2007).
White et al., Preservation of myocardial beta-adrenergic receptor signaling delays the development of heart failure after myocardial infarction, *Proc. Natl. Acad. Sci. USA*, 97(10):5428-33 (2000).
Winstel et al., Peptide inhibitors of G protein-coupled receptor kinases, *Biochem. Pharmacol.*, 70(7):1001-8 (2005).
Yi et al., Myocyte redistribution of GRK2 and GRK5 in hypertensive, heart-failure-prone rats, *Hypertension*, 39(6):1058-63 (2002).
Yi et al., The Anatomical Record. Part A, Discoveries in Molecular, Cellular, and Evolutionary Biology 282:13-23 (2005).
International Search Report and Written Opinion of the International Search Authority, United States Patent Office, PCT/US16/39526, dated Sep. 22, 2016.
International Preliminary Report on Patentability, PCT/US16/39526, dated Dec. 26, 2017.

* cited by examiner

G PROTEIN-COUPLED RECEPTOR KINASE INHIBITORS AND METHODS FOR USE OF THE SAME

CROSS-REFERENCE TO RELATED APPLICATION

This application is filed pursuant to 35 U.S.C. § 371 as a U.S. National Phase Application of International Application No. PCT/US2016/039526 (filed on Jun. 27, 2016), claiming the benefit under 35 U.S.C. § 119(e) of U.S. Provisional Patent Application Ser. No. 62/185,242 filed Jun. 26, 2015, the disclosures of which are each hereby incorporated herein by reference.

STATEMENT OF GOVERNMENT SUPPORT

This invention was made with government support under HL071818 and HL086865 awarded by the National Institutes of Health. The Government has certain rights in the invention.

BACKGROUND

Technical Field

The present disclosure relates to inhibitors for G protein-coupled receptor kinase ("GRK"), and methods of using the GRK inhibitors for the treatment of heart disease and hypertension.

Description of Related Technology

Eukaryotic cells regulate the strength and duration of signaling cascades, and therefore, must rapidly adapt to changes in their extracellular environment. G protein-coupled receptors ("GPCRs") are the largest class of receptors in humans, and regulate nearly all aspects of eukaryotic cell physiology. GPCR activity is controlled via the phosphorylation of serine and threonine residues in GPCR cytoplasmic tails and loops by G protein-coupled receptor kinases ("GRKs") (see Gurevich et al., Pharmacol Ther 133:40-69 (2012); Pitcher et al. Annu Rev Biochem 67:653-692 (1998)). The phosphorylated GPCRs recruit arrestins (see Gurevich and Gurevich Pharmacol Ther 110:465-502 (2006)), which uncouple the GPCRs from G proteins, target the receptors to clathrin-coated pits for endocytosis, and serve as adaptors for other signaling pathways (see Claing et al., Prog Neurobiol 66:61-79 (2002); Lymperopoulos Curr Pharm Des 18:192-198 (2012); Reiter et al. Annu Rev Pharmacol Toxicol 52:179-197 (2012)).

GRKs can be classified in one of three subfamilies based on gene structure and homology. The vertebrate-specific GRK1 subfamily includes GRK1 (rhodopsin kinase) and GRK7, which are expressed in the rod and cone cells of the retina. The GRK2 subfamily, which includes GRK2 and GRK3, are Gβγ-dependent and play important roles in the heart and olfactory neurons, respectively. In particular, GRK2 phosphorylates activated β-adrenergic receptors, thereby preventing overstimulation of cAMP-dependent signaling (see, e.g., Diviani et al. J Biol Chem 271:5049-5058 (1996); Hausdorff et al., Symp Soc Exp Biol 44:225-240 (1990); Lefkowitz et al., Trends Pharmacol Sci 11:190-194 (1990)). The GRK4 subfamily includes GRK4, 5, and 6. GRK5 and 6 are ubiquitously expressed. GRK5 plays an important role in heart function, albeit distinct from GRK2. All GRKs selectively recognize and phosphorylate activated GPCRs, but phosphorylate peptide substrates derived from these same receptors with $K_M$ values up to three orders of magnitude higher than for the full length activated receptor (see Palczewski et al., Biochemistry 27:2306-2313 (1988)), indicating the existence of an allosteric docking site on GRKs.

GRK2 overexpression in the heart is a biomarker for heart failure, and leads to uncoupling of heart function from sympathetic control. In the failing heart, the loss of cardiac output promotes increased levels of circulating catecholamines, resulting in severe uncoupling of βARs and a loss of inotropic reserve (see Eschenhagen Nat Med 14:485-487 (2008)). This uncoupling coincides with a 2-3 fold increase in GRK2 activity accompanied by an increase in both protein and mRNA levels (see Ungerer Circulation 87:454-463 (1993); Ungerer Circ Res 74: 206-213 (1994)). Thus, in chronic heart failure, GRKs become overexpressed and are linked to disease progression. Studies in mice overexpressing GRK2 in the heart show attenuation of isoproterenol (Iso)-stimulated contractility, reduced cAMP levels, and impaired cardiac function (see Koch et al., Science 268:1350-1353 (1995)), likely through desensitization of cardiac $β_1$-adrenergic receptors (see Vinge et al. Mol Pharmacol 72:582-591 (2007)). Therefore, inhibition of GRK2 function could be beneficial during heart failure (see Hata et al., J Mol Cell Cardiol 37:11-21 (2004); Lymperopoulos et al., J Biol Chem 285:16378-16386 (2010)). For example, studies in animal models using the GRK2 inhibitory protein βARKct, or with cardiac-specific GRK2 gene deletion, have shown that inhibition of GRK2 or lowering expression improves heart failure outcome (see Raake et al., Eur Heart J, Jan. 19, 2012; Raake et al., Circ Res 103:413-422 (2008); Rengo et al., Circulation 119:89-98 (2009); Rockman et al., Proc Natl Acad Sci USA 95:7000-7005 (1998); Shah et al., Circulation 103:1311-1316 (2001); White et al., Proc Natl Acad Sci USA 97:5428-5433 (2000)).

Because GRK2 overexpression in the heart is a biomarker for heart failure, inhibitors of GRK2 have been developed for the treatment of cardiovascular disease. Polyanionic GRK2 inhibitors, such as heparin and dextran sulfate, however, are nonselective (see Benovic et al., J Biol Chem 264:6707-6710 (1989)). Although the natural product balanol was found to inhibit GRK2 in the low nanomolar range, it is a non-selective inhibitor of the protein kinase A, G and C family (AGC kinases) (see Setyawan et al., Mol Pharmacol 56:370-376 (1999); Tesmer et al., J Med Chem 53:1867-1870 (2010)). Other inhibitors of GRKs have also been described, but these either have poor potency (see Iino et al., J Med Chem 45:2150-2159 (2002), low selectivity (see Winstel et al., Biochem Pharmacol 70:1001-1008 (2005)), or non-drug like properties (see Benovic et al., Science 246:235-240 (1989)). Paroxetine, a selective serotonin re-uptake inhibitor ("SSRI") is a moderately selective inhibitor of GRK2, but only exhibits micromolar potency of around 20 µM (see Thal et al., ACS Chem Biol 7:1830-1830 (2012)). Takeda103A is selective for the GRK2/3 subfamily (see WO 2007/034846), but has poor bioavailability (see Thal et al., Mol Pharmacol 80:294-303 (2011)).

GRK5 overexpression in transgenic mouse models results in higher levels of β-adrenergic receptor desensitization (see Rockman et al. Proc Natl Acad Sci USA 93: 9954-9959 (1996)), decreased cardiac output and contractility (see Chen et al. Annals of Thoracic Surgery 71:1320-1324 (2001)), and exaggerated hypertrophy and early heart failure compared to control mice (see Martini et al. Proc Natl Acad Sci USA 105:12457-12462 (2008)). It is also suggested that GRK5 is at least partially responsible for changes in myocardial function during heart failure. Increased nuclear accumulation of GRK5 in cardiomyocytes has been observed in spontaneously hypertensive heart failure rats (see Yi et al. Hypertension 39:1058-1063 (2002); Yi et al. The Anatomical Record. Part A, Discoveries in Molecular, Cellular, and Evolutionary Biology 282:13-23 (2005)), during the hypertrophic response to pressure overload (see Martini et al. Proc Natl Acad Sci USA 105:12457-12462 (2008)), and after myocyte stimulation with $G_q$-coupled receptor agonists such as phenylephrine or angiotensin II (see Gold et al. PLoS One 8:e57324, (2013)). In the nucleus, GRK5 augments the transcription of MEF2-associated hypertrophic genes by phosphorylating histone deacetylase-5 (HDAC5), a myocyte enhancer factor-2 (MEF2) repressor (see Martini et al. Proc Natl Acad Sci USA 105:12457-12462 (2008)). Without being bound by any particular theory, these data is consistent with the hypothesis that GRK5 is involved in cardiac hypertrophy that results from chronic hypertension. As for GRK2, polyanions such as heparin and dextran sulfate are potent but non-selective inhibitors of GRK5 (see Kunapuli et al. J. Biol. Chem. 269:1099-105 (1994)). The FDA approved drug amlexanox was recently identified as a GRK5 inhibitor with about 10 μM micromolar potency (see Homan et al., Molecules 19:16937-49 (2014)), and inhibitors against other kinase targets developed by GlaxoSmithKline, such as GSK216323A, demonstrate low micromolar potency against GRK5, but only moderate or no selectivity for GRK5 over GRK2 (see Homan et al. ACS Chem. Biol. 10:310-319 (2015)).

Therefore, there is a need for GRK inhibitors that exhibit high potency, high selectivity, and good pharmacokinetic properties for the treatment and prevention of cardiac disease.

SUMMARY

Described herein are compounds of Formula (I):

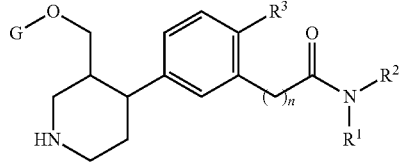

(I)

wherein:
G is

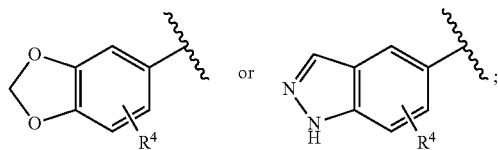

n is 0, 1, or 2;
$R^1$ is H, $C_{1-8}$alkyl, $C_{2-8}$alkenyl, $C_{3-8}$ cycloalkyl, $C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;
$R^2$ is $C_{1-8}$alkyl, $C_{2-8}$alkenyl, $C_{0-4}$alkylene-$C_{3-8}$ cycloalkyl, $C_{0-4}$alkylene-$C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;
$R^3$ is H, F, Cl, $CF_3$, $CHF_2$, $CH_2F$, or $CH_3$; and
$R^4$ is H, F, or Cl.

In some embodiments, the compound of Formula (I) comprises a compound of Formula (I'):

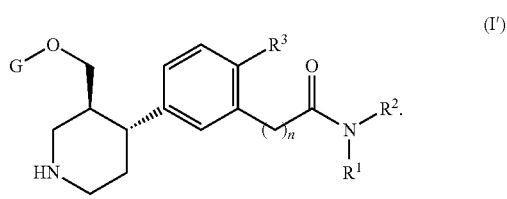

(I')

In some embodiments, $R^1$ is H. In other embodiments, $R^1$ is $C_{1-8}$alkyl or $C_{2-8}$alkenyl.

In some embodiments, $R^2$ is $C_{1-8}$ alkyl. In other embodiments, $R^2$ is $C_{0-4}$alkylene-$C_{3-8}$ cycloalkyl or $C_{0-4}$alkylene-$C_{3-8}$ cycloalkenyl. In various embodiments, $R^2$ is $C_{1-4}$ alkylene-aryl or $C_{1-4}$ alkylene-heteroaryl, such as $C_{1-2}$ alkylene-aryl or $C_{1-2}$ alkylene-heteroaryl. For example, $R^2$ can comprise

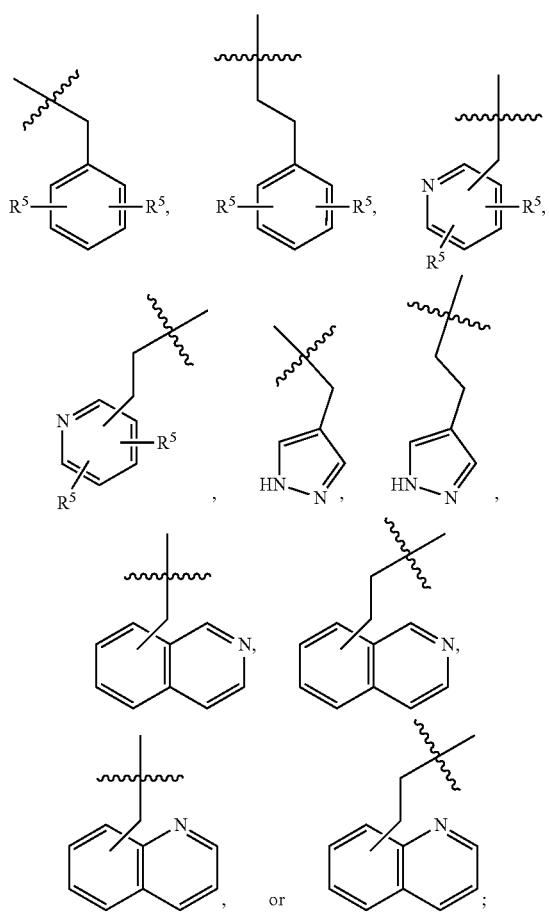

wherein each $R^5$ independently is H, halo, $C_{1-4}$ alkyl, or $C_{1-4}$ alkoxyl. In some embodiments, $R^2$ comprises

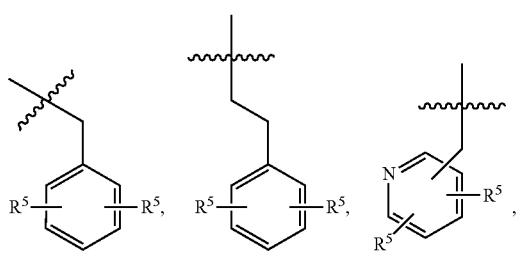
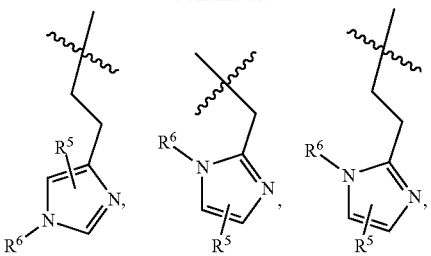
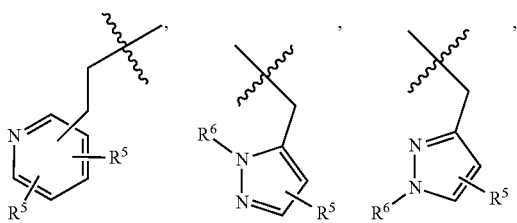
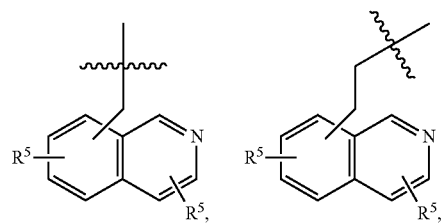
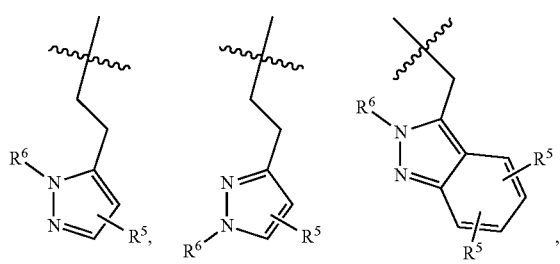
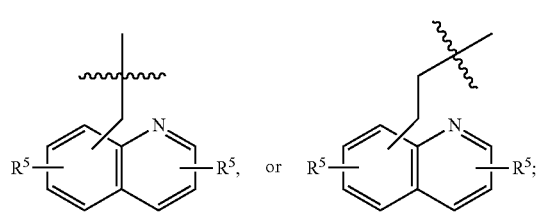
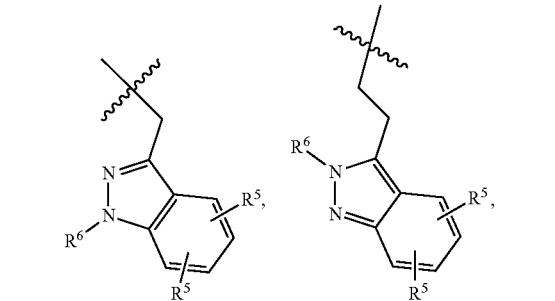
wherein each $R^5$ independently is H, halo, $C_{1-4}$ alkyl, or $C_{1-4}$ alkoxyl, and $R^6$ H or $C_{1-5}$ alkyl. For example, $R^2$ can include
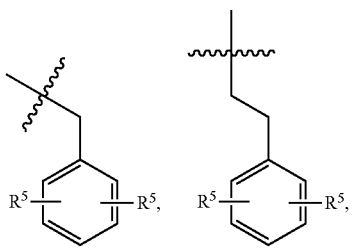
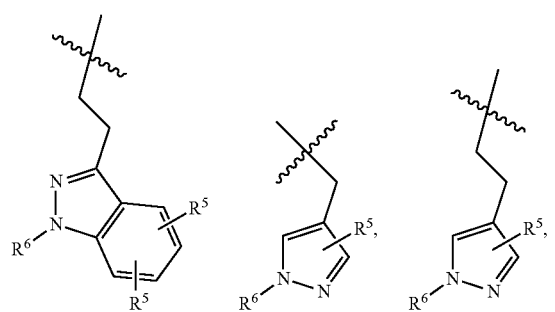
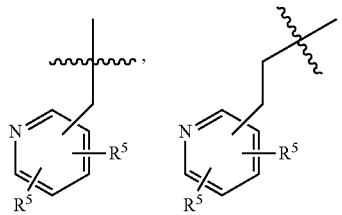
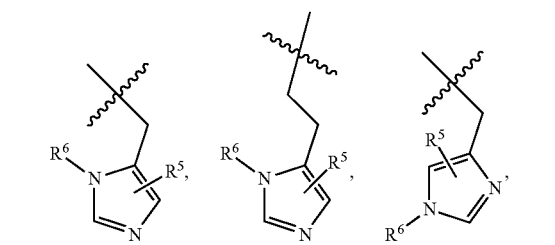
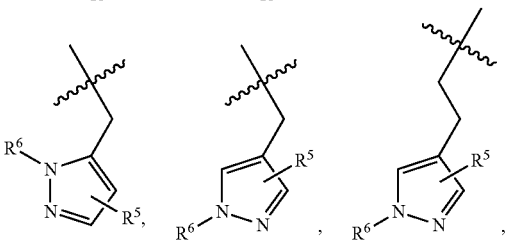

-continued

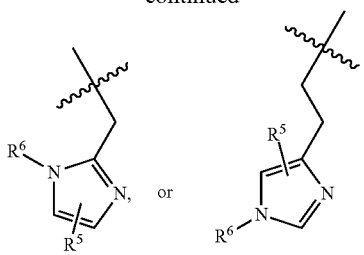 or 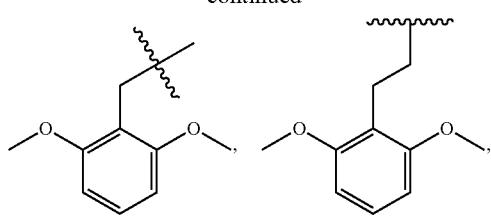

In some embodiments, each $R^5$ is H. In other embodiments, one $R^5$ is H and one $R^5$ is selected from the group consisting of halo (e.g., F or Cl), $C_{1-4}$ alkyl (e.g., $CH_3$ or $CF_3$), or $C_{1-4}$ alkoxyl (e.g., $OCH_3$ or $OCF_3$). In other embodiments, each $R^5$ is halo (e.g., F or Cl), $C_{1-4}$ alkyl (e.g., $CH_3$ or $CF_3$), or $C_{1-4}$ alkoxyl (e.g., $OCH_3$ or $OCF_3$). In any of these embodiments, each $R^5$ can be ortho. In some embodiments, $R^6$ is H. In various embodiments, $R^6$ is $C_{1-5}$ alkyl. In some cases, $R^6$ is methyl. For example, $R^2$ can comprise

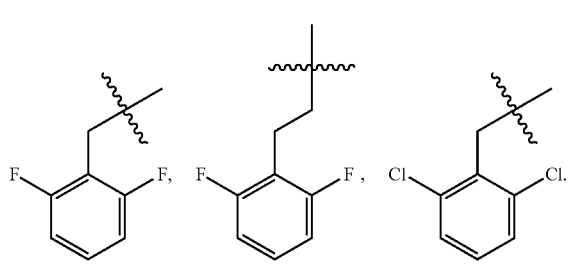

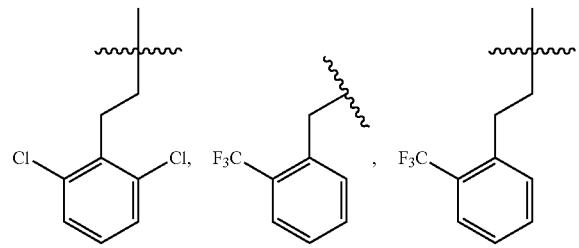

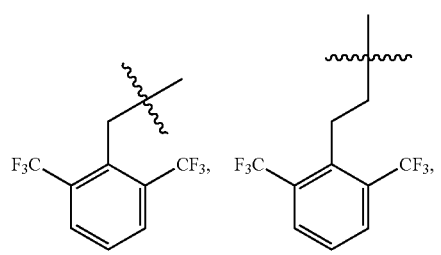

-continued

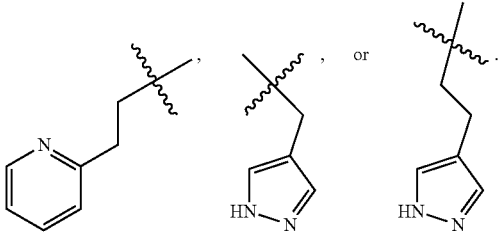

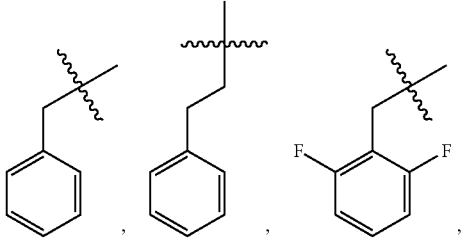

In some cases, $R^2$ can comprise:

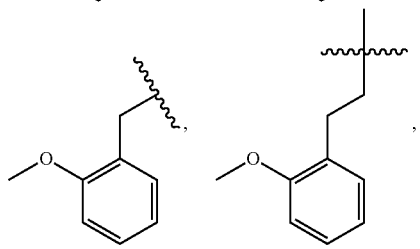

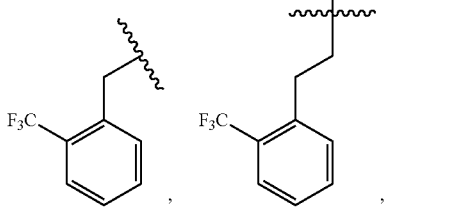

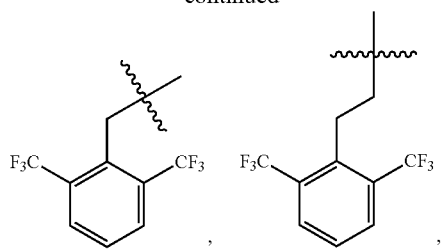
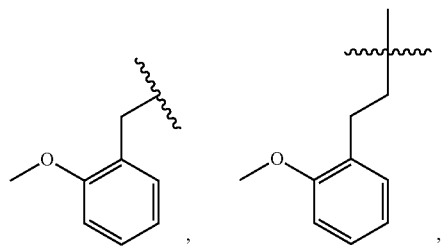
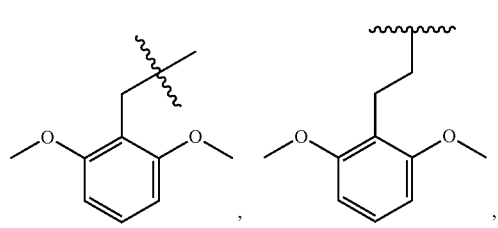
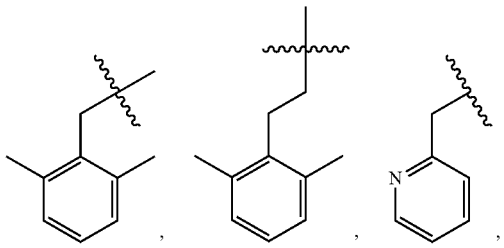
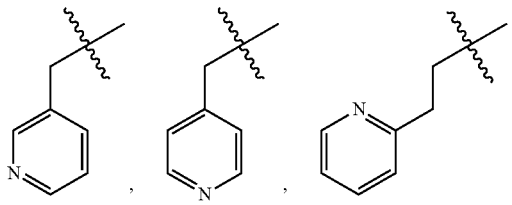
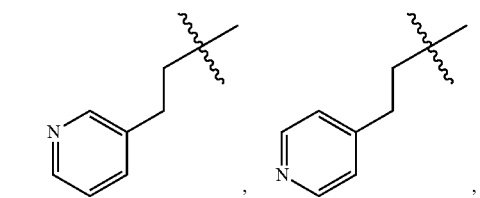
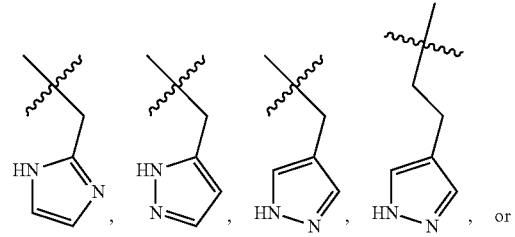

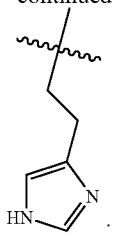

In some embodiments, $R^3$ is H or Cl. In other embodiments, $R^3$ is F. In some cases, $R^3$ is $CF_3$, $CHF_2$, $CH_2F$, or $CH_3$.

In some cases, $R^4$ is H. In various cases, $R^4$ is Cl or F.

In some embodiments, n is 0. In other embodiments, n is 1. In yet other embodiments, n is 2.

In some cases, G is

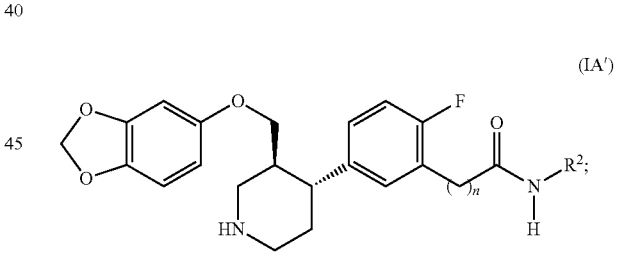

In various cases, G is

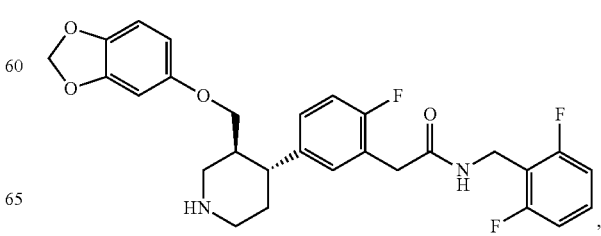

In some embodiments, the compound of Formula (I') comprises a compound of Formula (IA'):

(IA')

n is 0 or 1; and
$R^2$ is $C_{1-2}$ alkylene-aryl or $C_{1-2}$ alkylene-heteroaryl.

For example, described herein are compounds selected from the group consisting of:

E01

E02
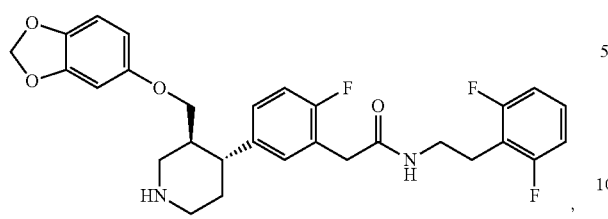
E03
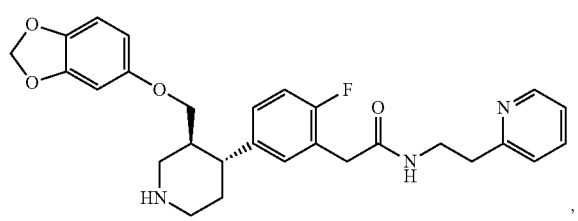
E04
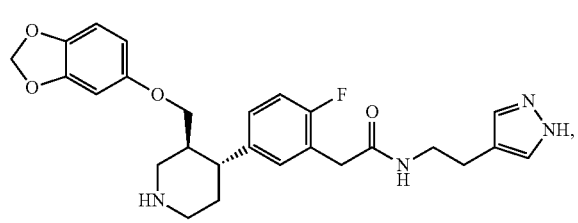
E05
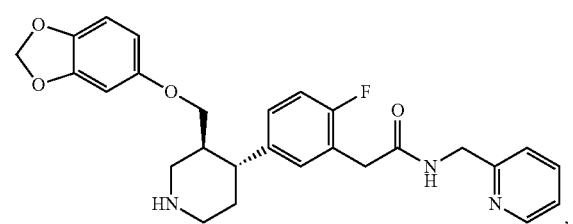
E06
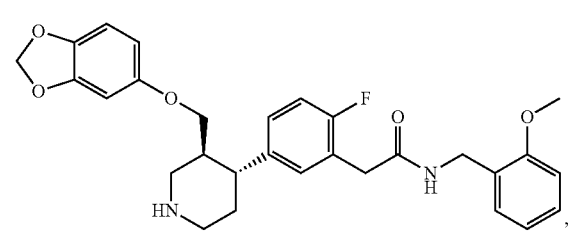
E07
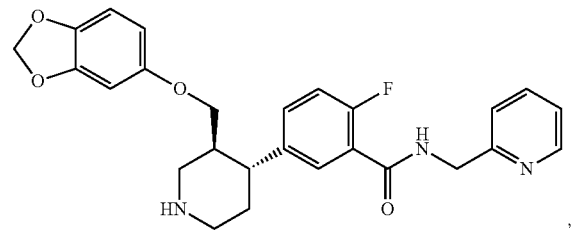
E08
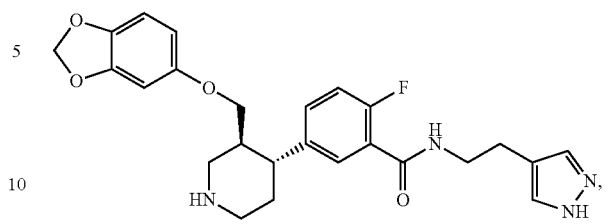
E09
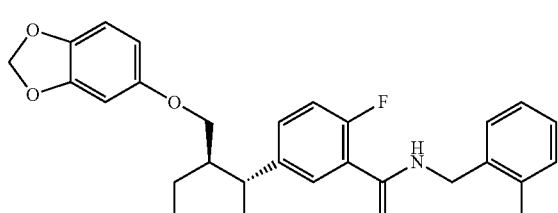
E10
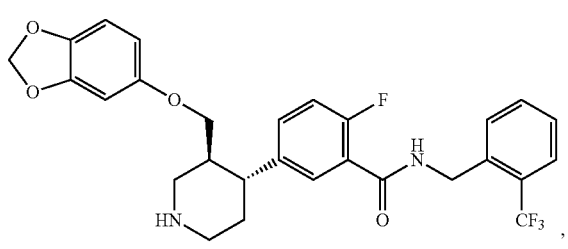
E11
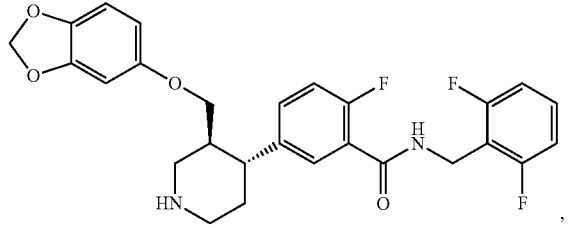
E12
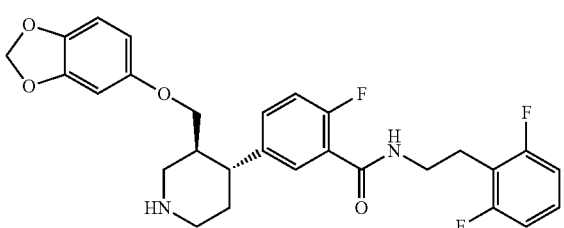
E13
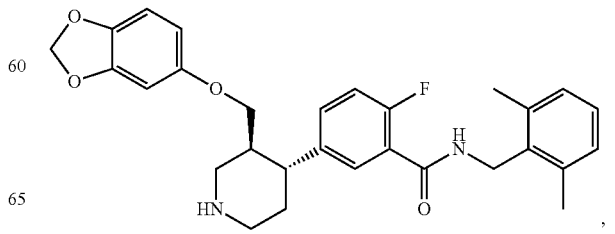

13
-continued
E14
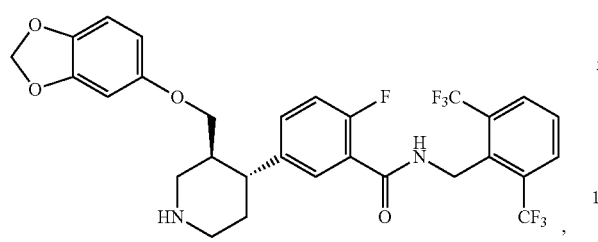
E15
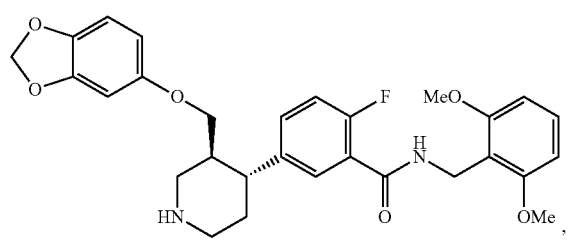
E16
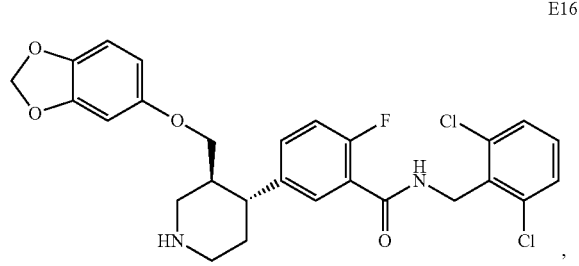
E17
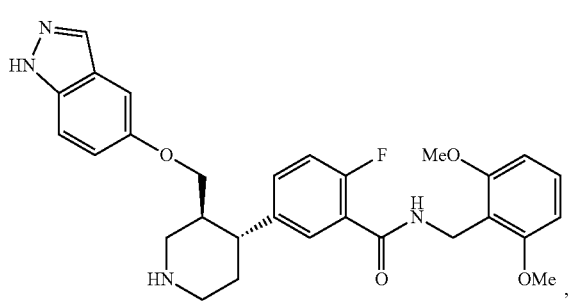
E18
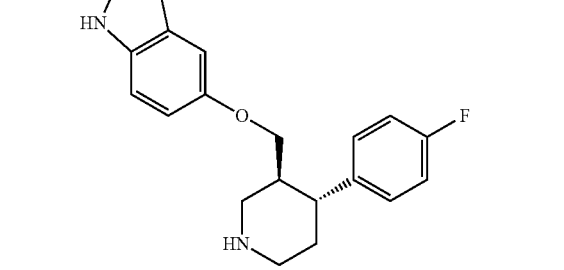
14
-continued
E19
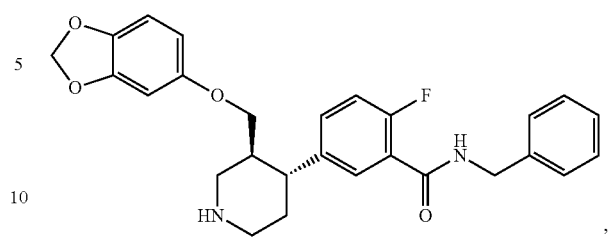
E20
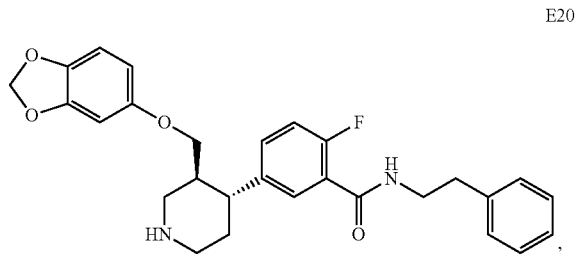
E22
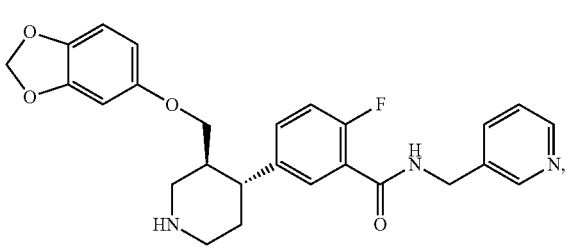
E22
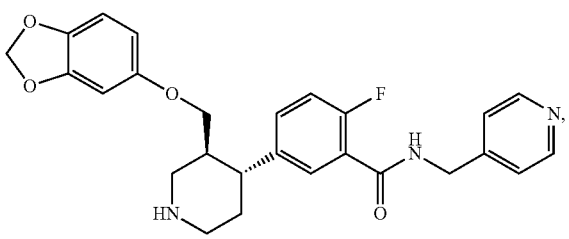
E23
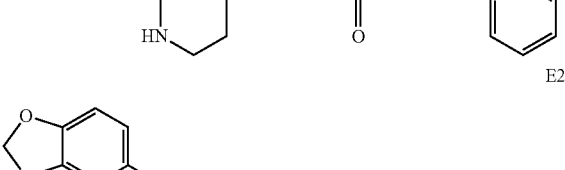
E24

E25

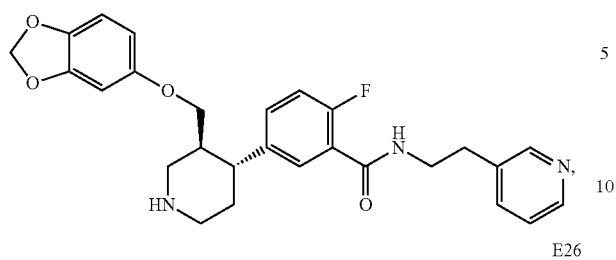

E26

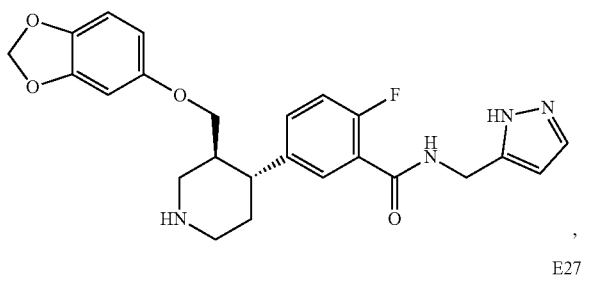

E27

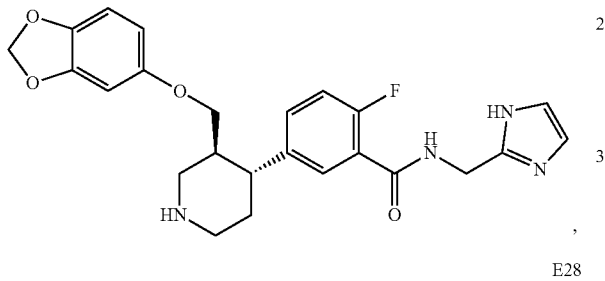

E28

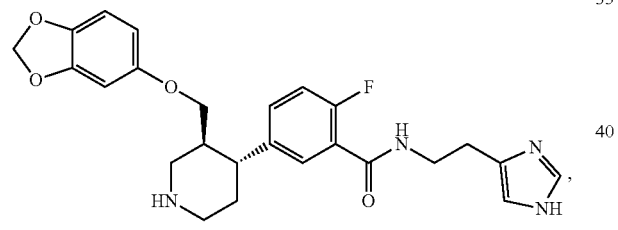

E29

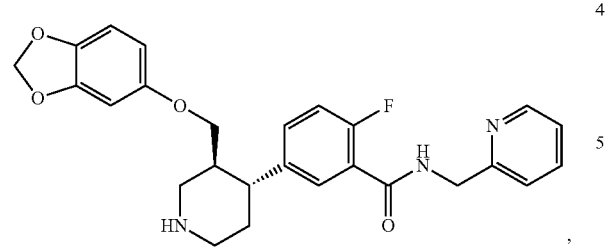

E30

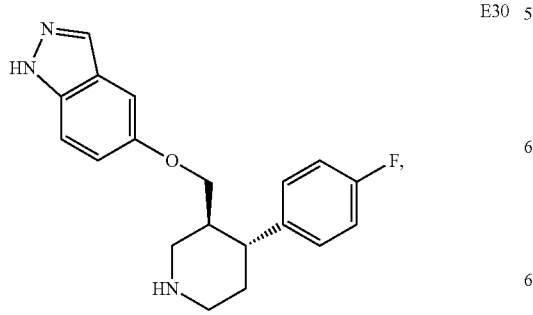

E31

, and

E32

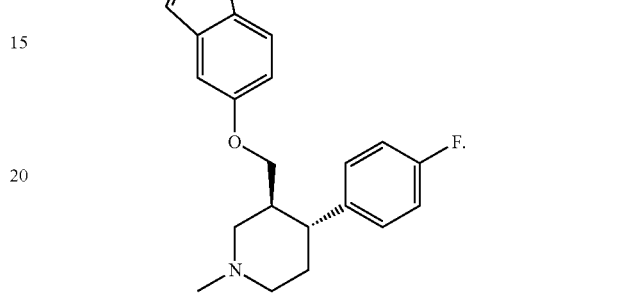

Also provided herein are compounds selected from the group consisting of E1-E17.

Another aspect of the disclosure relates to a pharmaceutical formulation comprising a compound as disclosed herein, or a pharmaceutically acceptable salt thereof, as defined herein, and a pharmaceutically acceptable excipient.

Yet another aspect of the invention relates to a method of inhibiting GRK in a cell, such as GRK 2 and/or GRK5, comprising contacting the cell with a compound as disclosed herein (e.g., Formula (I), Formula (I'), or Formula (IA')) or a pharmaceutically acceptable salt thereof, as defined herein, or a pharmaceutical formulation thereof, in an amount effective to inhibit GRK, such as GRK2 and/or GRK5. In some cases, the cell is a myocyte, such as a cardiomyocyte. The contacting can occur, for example, in vivo. In some embodiments, the contacting comprises administering to a subject in need thereof. In some cases, the subject suffers from heart disease. The heart disease can be one or more of cardiac failure, cardiac hypertrophy, and hypertension.

Still another aspect of the disclosure relates to a method of treating heart disease in a subject comprising administering to the subject a therapeutically effective amount of a pharmaceutical formulation comprising a compound described herein (e.g., a compound of Formula (I), Formula (I'), or Formula (IA')), or a pharmaceutically acceptable salt thereof, as defined herein.

Further aspects and advantages will be apparent to those of ordinary skill in the art from a review of the following detailed description, taken in conjunction with the drawings. While the inhibitors and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Disclosed herein are inhibitors of GRK, such as GRK2 and/or GRK5. The GRK inhibitors disclosed herein can be used to treat or prevent heart disease (e.g., cardiac failure, cardiac hypertrophy, hypertension), improving the quality of life for afflicted individuals.

The GRK inhibitors disclosed herein have a structure of Formula (I)

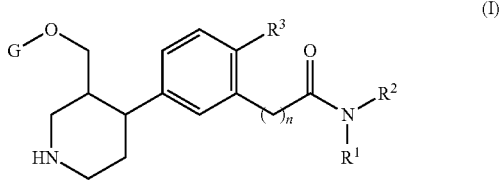

(I)

wherein the substituents are as described in detail below.

In some cases, the compounds described herein (e.g., the compounds of Formulae (I), (I'), (IA'), and pharmaceutically acceptable salts thereof) inhibit GRK2 with an $IC_{50}$ of about 15 µM or less. In some embodiments, the compounds described herein (e.g., the compounds of Formulae (I), (I'), (IA'), and pharmaceutically acceptable salts thereof) have an $IC_{50}$ value for GRK2 of less than about 10 µM, or less than about 5 µM, or less than about 1 µM, or less than about 0.5 µM, or less than about 0.4 µM, or less than about 0.3 µM, or less than about 0.2 µM, or less than about 0.1 µM, or less than about 0.05 µM. In various cases, the $IC_{50}$ value of the compounds described herein (e.g., the compounds of Formulae (I), (I'), (IA'), and pharmaceutically acceptable salts thereof) is about 0.05 µM to about 15 µM, or about 0.05 µM to about 0.4 µM, or about 0.05 µM to about 0.1 µM.

In various cases, the compounds described herein (e.g., the compounds of Formulae (I), (I'), (IA'), and pharmaceutically acceptable salts thereof) optionally inhibit GRK5 with an $IC_{50}$ of about 75 µM or less. In some embodiments, the compounds described herein (e.g., the compounds of Formulae (I), (I'), (IA'), and pharmaceutically acceptable salts thereof) have an $IC_{50}$ value for GRK5 of less than about 60 µM, or less than about 50 µM, or less than about 40 µM, or less than about 30 µM, or less than about 20 µM, or less than about 10 µM, or less than about 0.5 µM, or less than about 0.2 µM. In various cases, the $IC_{50}$ value of the compounds described herein is about 0.2 µM to about 75 µM, or about 0.5 µM to about 60 µM, or about 10 µM to about 40 µM.

In various cases, the compounds described herein (e.g., the compounds of Formulae (I), (I'), (IA'), and pharmaceutically acceptable salts thereof) selectively inhibit GRK2 over GRK5. Without being bound by any particular theory, the hydrophobic subsite of GRK2 is either larger than GRK5, or can bind a ligand in a more closed conformation. Therefore, compounds having a substituted amide group (e.g., wherein at least one of $R^1$ and $R^2$ is other than hydrogen), such as compounds of Formulae (I), (I'), (IA'), and pharmaceutically acceptable salts thereof, favor GRK2 over GRK5. As used herein, a compound describe herein is "selective" for GRK2 over GRK5 if it inhibits GRK2 to a greater extent compared to GRK5. In some cases, the compounds described herein (e.g., the compounds of Formula (I), (I'), (IA'), and pharmaceutically acceptable salts thereof) inhibit GRK2 at least 50% more than GRK5 (e.g., at least 1.5-fold), as measured in the assays as described in the Examples section below. In various cases, the selectivity for GRK2 over GRK5 is at least 2.0-fold, or at least 10-fold, or at least 20-fold, or at least 50-fold, or at least 100-fold, or at least 200-fold, or at least 300-fold, or at least 400-fold, or at least 500-fold, or at least 600-fold, or at least 700-fold, or at least 800-fold, or at least 900-fold, or at least 1000-fold, or at least 1100-fold, or at least 1200-fold, or at least 1300-fold, or at least 1400-fold, or at least 1500-fold, or at least 1600-fold, or at least 1700-fold, or at least 1800-fold, or at least 1900-fold, or at least 2000-fold.

In various cases, the compounds described herein (e.g., the compounds of Formulae (I), (I'), (IA'), and pharmaceutically acceptable salts thereof) selectively inhibit GRK2 over GRK1. As used herein, a compound of Formula (I) is "selective" for GRK2 over GRK1 if it inhibits GRK2 to a greater extent compared to GRK1. In some cases, the compounds described herein inhibits GRK2 at least 50% more than GRK1 (e.g., at least 1.5-fold), as measured in the assays as described in the Examples section below. In various cases, the selectivity for GRK2 over GRK1 is at least 2.0-fold, or at least 10-fold, or at least 20-fold, or at least 50-fold, or at least 100-fold, or at least 200-fold, or at least 300-fold, or at least 400-fold, or at least 500-fold, or at least 600-fold, or at least 700-fold, or at least 800-fold, or at least 900-fold, or at least 1000-fold, or at least 1100-fold, or at least 1200-fold, or at least 1300-fold, or at least 1400-fold, or at least 1500-fold, or at least 1600-fold, or at least 1700-fold, or at least 1800-fold, or at least 1900-fold, or at least 2000-fold.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_2$-$C_7$ alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkylene" refers to an alkyl group having a substituent. For example, the term "alkylene-aryl" refers to an alkyl group substituted with an aryl group. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group.

As used herein, the term "heterocycloalkyl" is defined similarly as cycloalkyl, except the ring contains one to three heteroatoms independently selected from oxygen, nitrogen, or sulfur. Nonlimiting examples of heterocycloalkyl groups include piperdine, pyrazolidine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected alkyl, alkylene OH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, and alkyleneheteroaryl.

As used herein, the term "cycloalkenyl" is defined similarly to "cycloalkyl" except for containing at least one carbon-carbon double bond. The term $C_n$ means the cycloalkenyl group has "n" carbon atoms. For example, $C_5$ cycloalkenyl refers to a cycloalkenyl group that has 5 carbon atoms in the ring. $C_5$-$C_8$ cycloalkenyl refers to cycloalkenyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkenyl groups include cyclopropenyl, cyclobutenyl, cyclopentenyl, cyclohexenyl, cycloheptenyl, and cyclooctenyl. Unless otherwise indicated, a cycloalkenyl group can be an unsubstituted cycloalkenyl group or a substituted cycloalkenyl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "alkoxy" or "alkoxyl" as used herein refers to a "—O— alkyl" group. The alkoxy or alkoxyl group can be unsubstituted or substituted.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, ether, polyether, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds (e.g., a GRK inhibitor or combination of GRK inhibitors) that ameliorates, attenuates or eliminates one or more symptoms of a particular disease or condition (e.g., heart disease), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans). The terms patient and subject includes males and females.

As used herein, the term "pharmaceutically acceptable" means that the referenced substance, such as a compound of the present invention, or a formulation containing the compound, or a particular excipient, are safe and suitable for administration to a patient or subject. The term "pharmaceutically acceptable excipient" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

GRK Inhibitors

Provided herein is a compound of Formula (I), or a pharmaceutically acceptable salt thereof:

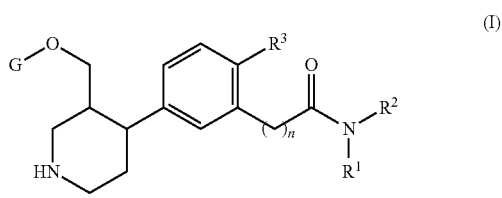

wherein:
n is 0, 1, or 2;
R$^1$ is H, C$_{1-8}$alkyl, C$_{2-8}$alkenyl, C$_{3-8}$ cycloalkyl, C$_{3-8}$ cycloalkenyl, C$_{1-4}$ alkylene-aryl, C$_{1-4}$ alkylene-heteroaryl, C$_{3-8}$ cycloalkylene-aryl, or C$_{3-8}$ cycloalkylene-heteroaryl;
R$^2$ is C$_{1-8}$alkyl, C$_{2-8}$alkenyl, C$_{0-4}$alkylene-C$_{3-8}$ cycloalkyl, C$_{0-4}$alkylene-C$_{3-8}$ cycloalkenyl, C$_{1-4}$ alkylene-aryl, $C_{1-4}$ alkylene-heteroaryl, $C_{3-8}$ cycloalkylene-aryl, or $C_{3-8}$ cycloalkylene-heteroaryl;
$R^3$ is H, F, Cl, $CF_3$, $CHF_2$, $CH_2F$, or $CH_3$; and
$R^4$ is H, F, or Cl.

In some embodiments, the compound of Formula (I) comprises a compound of Formula (I'):

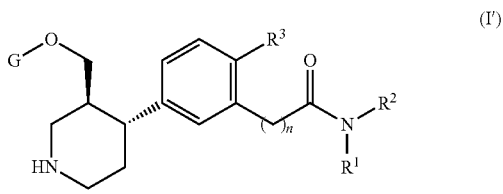

wherein, the substituents are described above.

In some embodiments, $R^1$ is H. In various embodiments, $R^1$ is $C_{1-8}$alkyl, for example, $C_{1-4}$ alkyl (e.g., methyl, ethyl, n-propyl, isopropyl, n-butyl, isobutyl, sec-butyl, or tert-butyl), or $C_{5-8}$ alkyl (e.g., $C_5$ alkyl or $C_6$ alkyl or $C_7$ alkyl or $C_8$ alkyl). In some cases, $R^1$ is $C_{2-8}$ alkenyl, for example, $C_{2-4}$alkenyl (e.g., $C_2$ alkenyl or $C_3$ alkenyl or $C_4$ alkenyl) or $C_{5-8}$alkenyl (e.g., $C_5$ alkenyl or $C_6$ alkenyl or $C_7$ alkenyl or $C_8$ alkenyl). The $C_{2-8}$ alkenyl can be monounsaturated. In some embodiments, $R^1$ is $C_{3-8}$ cycloalkyl (e.g., cyclopropyl, cyclobutyl, cyclopentyl, cyclohexyl) or cycloheptyl) or $C_{3-8}$ cycloalkenyl (e.g., cyclopentenyl, cyclohexenyl, or cycloheptenyl). The cycloalkyl and cycloalkenyl can be an isolated hydrocarbon ring or fused to a cycloalkyl group, a heterocycloalkyl group, an aryl group, a heteroaryl group, or a combination thereof. In some embodiments, $R^1$ is $C_{1-4}$ alkylene-aryl (e.g., $CH_2$-aryl, $CH_2CH_2$-aryl, or $CH_2CH_2CH_2$-aryl) or $C_{1-4}$ alkylene-heteroaryl (e.g., $CH_2$-heteroaryl, $CH_2CH_2$-heteroaryl, or $CH_2CH_2CH_2$-heteroaryl). In some cases, $R^1$ is $C_{3-8}$ cycloalkylene-aryl (e.g., cyclopropylene-aryl, cyclobutylene-aryl, cyclopentylene-aryl, or cyclohexylene-aryl) or $C_{3-8}$ cycloalkylene-heteroaryl (e.g., cyclopropylene-heteroaryl, cyclobutylene-heteroaryl, cyclopentylene-heteroaryl, or cyclohexylene-heteroaryl). In any of the embodiments disclosed herein, the aryl can be, for example, phenyl, naphthyl, tetrahydronaphthyl, phenanthrenyl, indanyl, indenyl, anthracenyl, and fluorenyl. In some cases, the aryl is phenyl or naphthyl. For example, the aryl can be phenyl. In any of the embodiments disclosed herein, the heteroaryl can be, for example, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl or benzothiazolyl. In some cases, the heteroaryl is pyridyl or pyrazolyl. The aryl group or heteroaryl group can be substituted or unsubstituted. In some embodiments, the aryl group or heteroaryl group is substituted with one or more of halo (e.g., fluoro, chloro, bromo, or a combination thereof), $C_{1-4}$ alkyl (e.g., methyl, trifluoromethyl, ethyl, propyl, isopropyl, n-butyl, isobutyl, sec-butyl, tert-butyl, or a combination thereof), $C_{1-4}$ alkoxyl (e.g., methoxyl, trifluoromethoxyl, ethoxyl, n-propoxyl, isopropoxyl, n-butoxyl, isobutoxyl, sec-butoxyl, tert-butoxyl, or a combination thereof), or a combination thereof. In various cases, the aryl group or heteroaryl group is monosubstituted. In some cases, the aryl group or heteroaryl group is disubstituted.

In various embodiments, $R^2$ is $C_{1-8}$alkyl, for example, $C_{1-4}$ alkyl (e.g., methyl, ethyl, n-propyl, n-butyl, isobutyl, sec-butyl, or tert-butyl) or $C_{5-8}$ alkyl (e.g., $C_5$ alkyl or $C_6$ alkyl or $C_7$ alkyl or $C_8$ alkyl). In some cases, $R^2$ is $C_{2-8}$ alkenyl, for example, $C_{2-4}$alkenyl (e.g., $C_2$ alkenyl or $C_3$ alkenyl or $C_4$ alkenyl) or $C_{5-8}$alkenyl (e.g., $C_5$ alkenyl or $C_6$ alkenyl or $C_7$ alkenyl or $C_8$ alkenyl). The $C_{2-8}$ alkenyl can be monounsaturated. In some embodiments, $R^2$ is $C_{0-4}$alkylene-$C_{3-8}$ cycloalkyl (e.g., cyclopropyl, cyclobutyl, cyclopentyl, cyclohexyl, or cycloheptyl) or $C_{0-4}$alkylene-$C_{3-8}$ cycloalkenyl (e.g., cyclopentenyl, cyclohexenyl, or cycloheptenyl). The cycloalkyl and cycloalkenyl can be an isolated hydrocarbon ring or fused to a cycloalkyl group, a heterocycloalkyl group, an aryl group, a heteroaryl group, or a combination thereof. In some embodiments, $R^2$ is $C_{1-4}$ alkylene-aryl (e.g., $CH_2$-aryl, $CH_2CH_2$-aryl, or $CH_2CH_2CH_2$-aryl) or $C_{1-4}$ alkylene-heteroaryl (e.g., $CH_2$-heteroaryl, $CH_2CH_2$-heteroaryl, or $CH_2CH_2CH_2$-heteroaryl). In some cases, $R^2$ is $C_{3-8}$ cycloalkylene-aryl (e.g., cyclopropylene-aryl, cyclobutylene-aryl, cyclopentylene-aryl, or cyclohexylene-aryl) or $C_{3-8}$ cycloalkylene-heteroaryl (e.g., cyclopropylene-heteroaryl, cyclobutylene-heteroaryl, cyclopentylene-heteroaryl, or cyclohexylene-heteroaryl). In any of the embodiments disclosed herein, the aryl can be, for example, phenyl, naphthyl, tetrahydronaphthyl, phenanthrenyl, indanyl, indenyl, anthracenyl, and fluorenyl. In some cases, the aryl is phenyl or naphthyl. For example, the aryl can be phenyl. In any of the embodiments disclosed herein, the heteroaryl can be, for example, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl or benzothiazolyl. In some cases, the heteroaryl is pyridyl or pyrazolyl. The aryl group or heteroaryl group can be substituted or unsubstituted. In some embodiments, the aryl group or heteroaryl group is substituted with one or more of halo (e.g., fluoro, chloro, bromo, or a combination thereof), $C_{1-4}$ alkyl (e.g., methyl, trifluoromethyl, ethyl, propyl, isopropyl, n-butyl, isobutyl, sec-butyl, tert-butyl, or a combination thereof), $C_{1-4}$ alkoxyl (e.g., methoxyl, trifluoromethoxyl, ethoxyl, n-propoxyl, isopropoxyl, n-butoxyl, isobutoxyl, sec-butoxyl, tert-butoxyl, or a combination thereof), or a combination thereof. In various cases, the aryl group or heteroaryl group is monosubstituted. In some cases, the aryl group or heteroaryl group is disubstituted. For example, $R^2$ can comprise

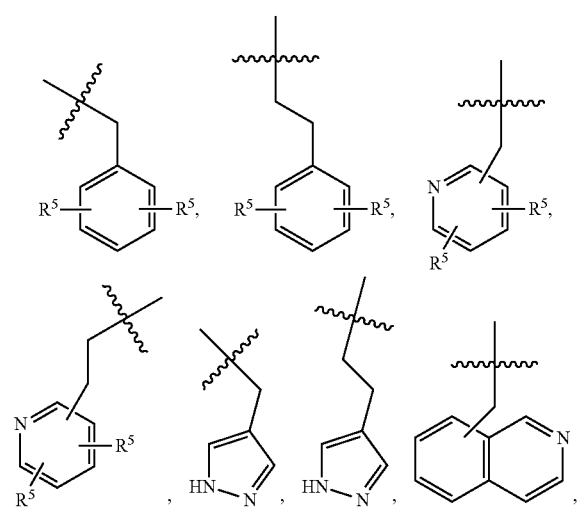

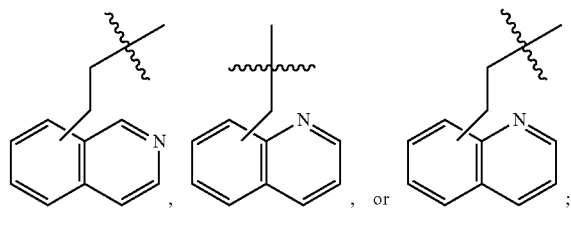
wherein each $R^5$ independently is H, halo, $C_{1-4}$ alkyl, or $C_{1-4}$ alkoxyl. In some embodiments, $R^2$ comprises
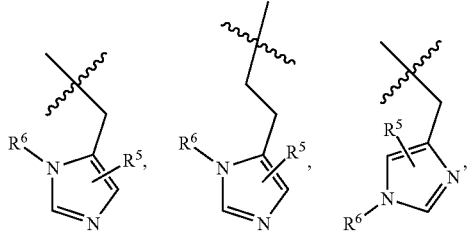
wherein each $R^5$ independently is H, halo, $C_{1-4}$ alkyl, or $C_{1-4}$ alkoxyl, and $R^6$ is H or $C_{1-5}$ alkyl (e.g., $CH_3$). For example, $R^2$ can include -continued

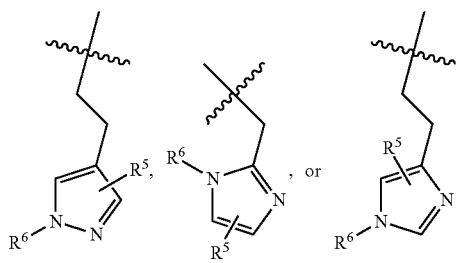

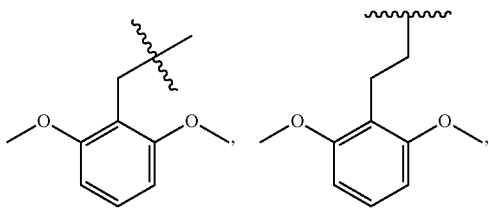

In some embodiments, each $R^5$ is H. In other embodiments, one $R^5$ is H and one $R^5$ is selected from halo (e.g., F or Cl), $C_{1-4}$ alkyl (e.g., $CH_3$ or $CF_3$), and $C_{1-4}$ alkoxyl (e.g., $OCH_3$ or $OCF_3$). In some cases, each $R^5$ is halo (e.g., F or Cl), or $C_{1-4}$ alkyl (e.g., $CH_3$ or $CF_3$), or $C_{1-4}$ alkoxyl (e.g., $OCH_3$ or $OCF_3$). In some of these embodiments, each $R^5$ is ortho to the alkylene chain. In some cases, each $R^5$ is meta to the alkylene chain. In several of these embodiments, one $R^5$ is ortho to the alkylene chain and the other $R^5$ is para to the alkylene chain. In some cases, one $R^5$ is ortho to the alkylene chain and the other $R^5$ is meta to the alkylene chain. In some embodiments, $R^6$ is H. In various embodiments, $R^6$ is $C_{1-5}$ alkyl. In some cases, $R^6$ is methyl. In various cases, $R^2$ can comprise a structure selected from

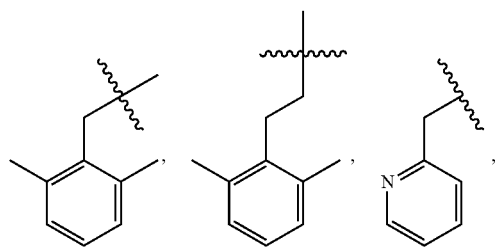

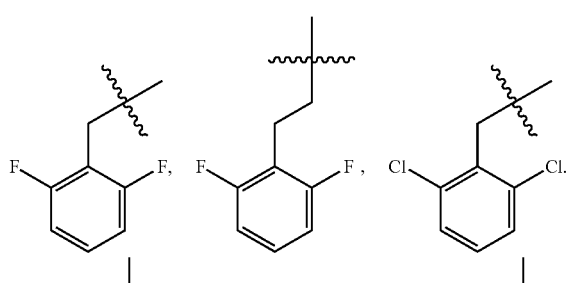

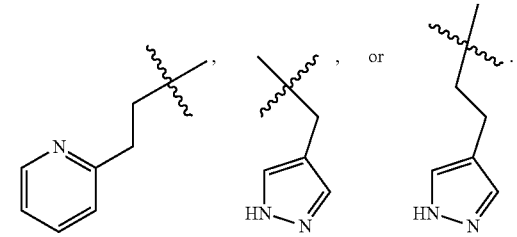

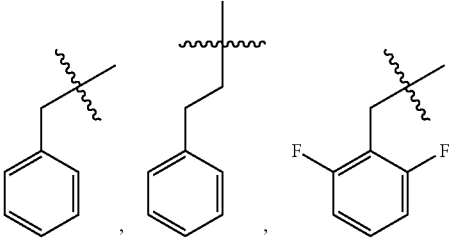

In some cases, $R^2$ can comprise

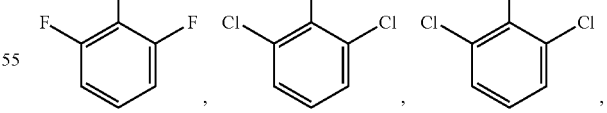

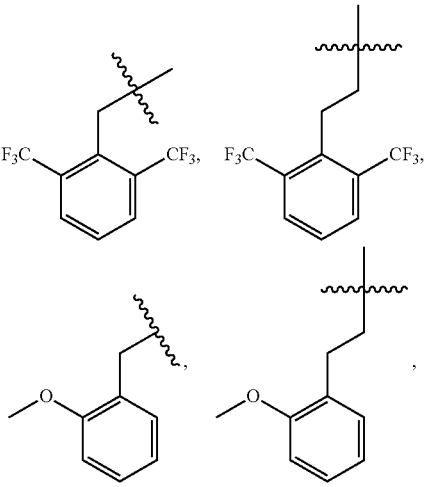

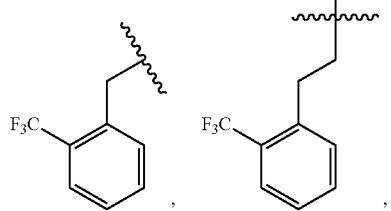

27
-continued

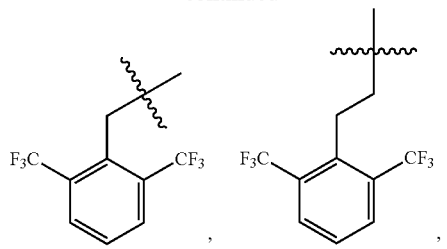

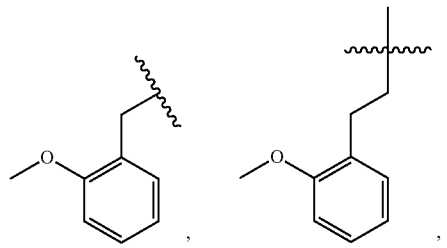

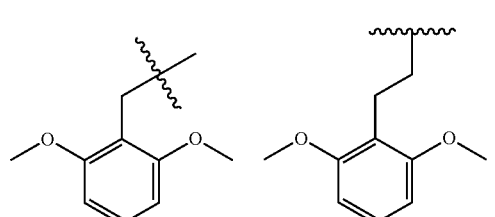

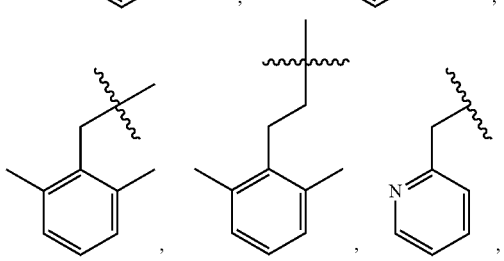

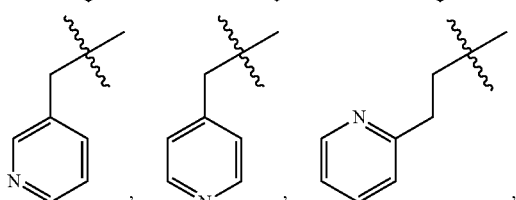

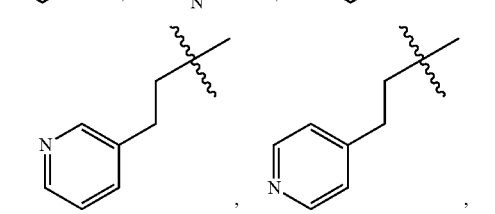, or

28
-continued

.

In some embodiments, $R^3$ is H, Cl, or $CH_3$. In various embodiments, $R^3$ is $CF_3$, $CHF_2$, or $CH_2F$. In other embodiments, $R^3$ is F.

In various embodiments, $R^4$ is H. In some embodiments, $R^4$ is Cl or F.

In some embodiments, n is 0. In various embodiments, n is 1. In some cases, n is 2.

In some cases, G is

.

In various cases, G is

.

Also provided herein is a compound of Formula (IA'), or a pharmaceutically acceptable salt thereof:

(IA')

wherein:
n is 0 or 1, and
$R^2$ is $C_{1-2}$ alkylene-aryl or $C_{1-2}$ alkylene-heteroaryl.

In some of these embodiments, $R^2$ is $CH_2$-aryl, $CH_2CH_2$-aryl, or $CH_2CH_2CH_2$-aryl, as previously described. In several of these embodiments, $R^2$ is $CH_2$-heteroaryl, $CH_2CH_2$-heteroaryl, or $CH_2CH_2CH_2$-heteroaryl, as previously described. The aryl group or heteroaryl group can be substituted or unsubstituted. In some embodiments, the aryl group or heteroaryl group is substituted with one or more of halo (e.g., fluoro, chloro, bromo, or a combination thereof), $C_{1-4}$ alkyl (e.g., methyl, trifluoromethyl, ethyl, propyl, isopropyl, n-butyl, isobutyl, sec-butyl, tert-butyl, or a combination thereof), $C_{1-4}$ alkoxyl (e.g., methoxyl, trifluoromethoxyl, ethoxyl, n-propoxyl, isopropoxyl, n-butoxyl, isobutoxyl, sec-butoxyl, tert-butoxyl, or a combination thereof), or a combination thereof, as previously described. For example, $R^2$ can comprise

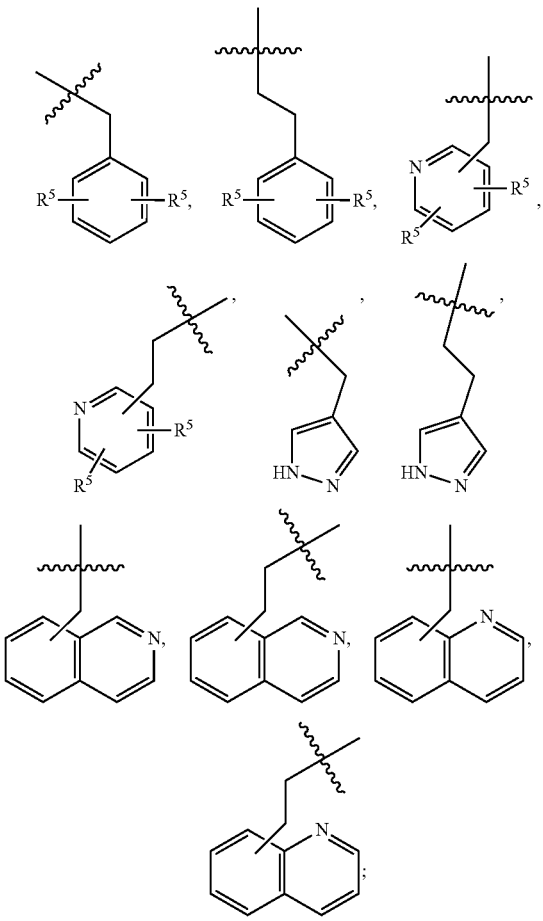

wherein each $R^5$ independently is H, halo, $C_{1-4}$ alkyl, or $C_{1-4}$ alkoxyl, as previously described. In some embodiments, $R^2$ comprises

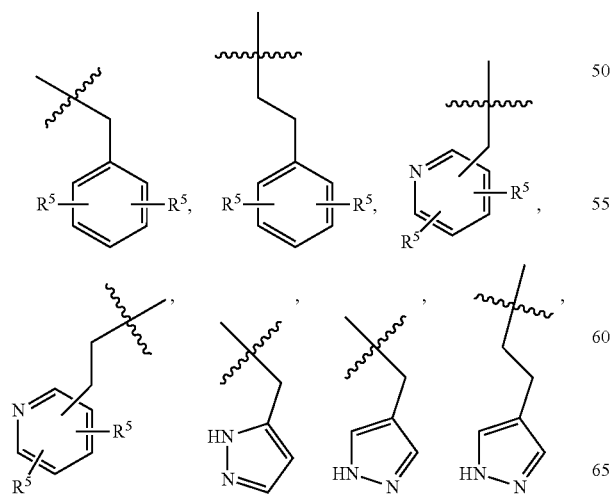

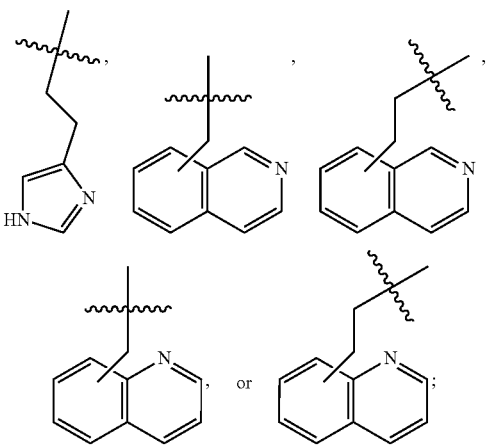

wherein each $R^5$ independently is H, halo, $C_{1-4}$ alkyl, or $C_{1-4}$ alkoxyl, as previously described. In various cases, $R^2$ can comprise a structure selected from

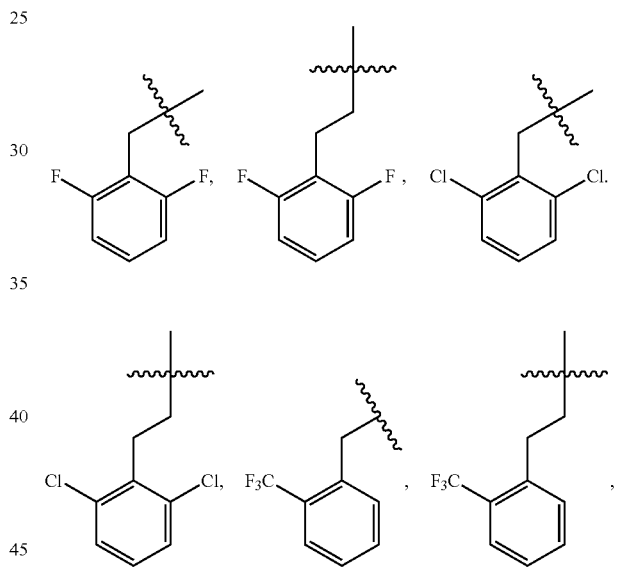

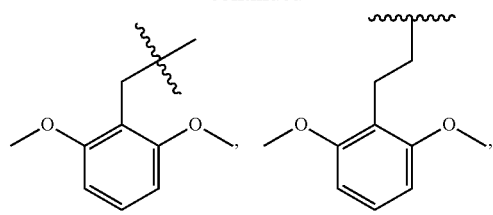
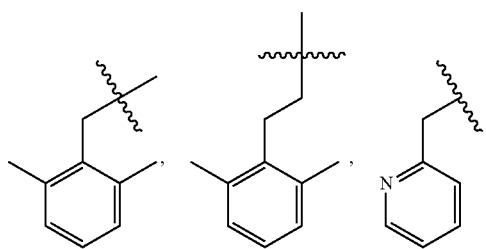
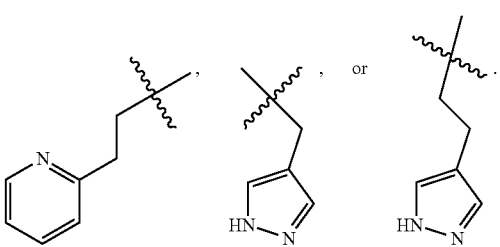
In some cases, R² can comprise
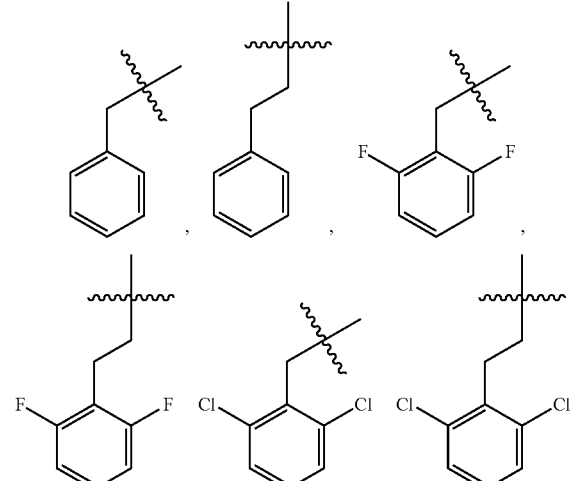
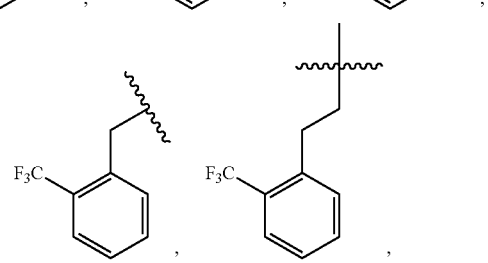
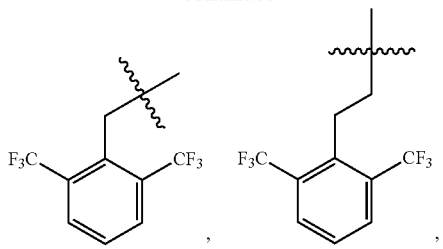
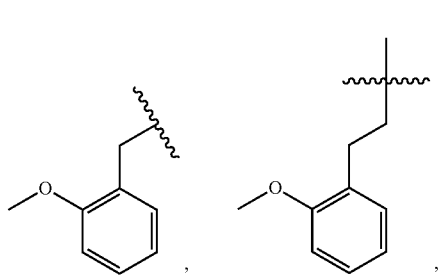
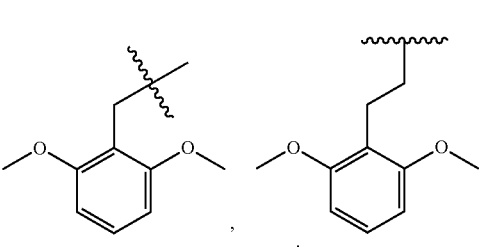
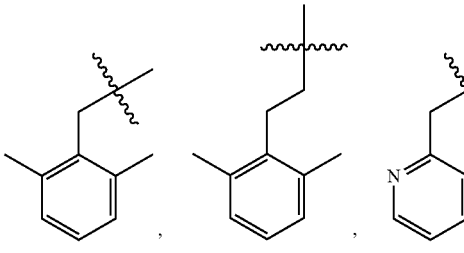
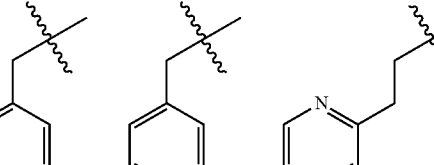
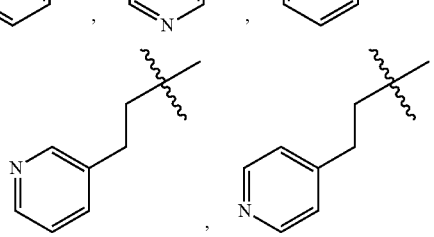, or -continued
Also provided herein are compounds selected from the group consisting of:
E01
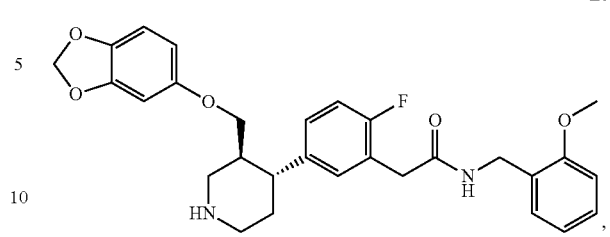
E02
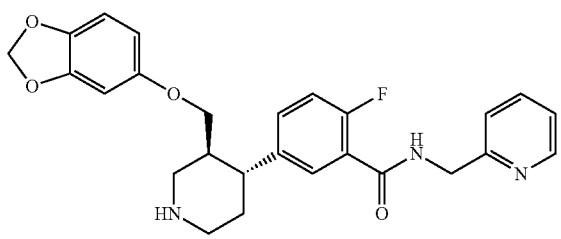
-continued
E06
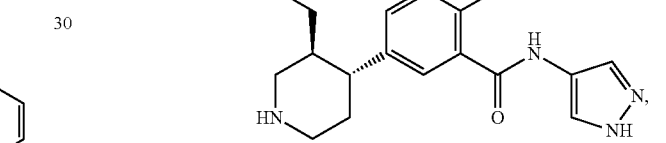
E07
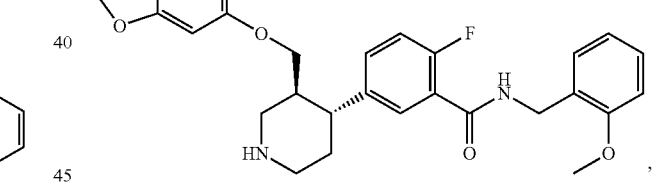
E08
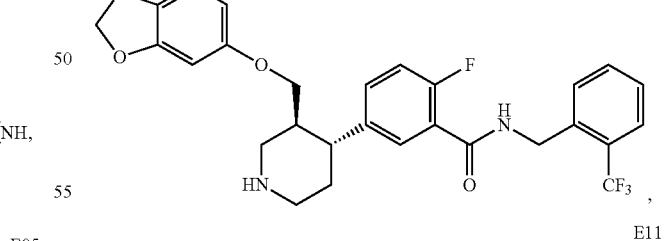
E09
E03
E04
E05
E10
E11

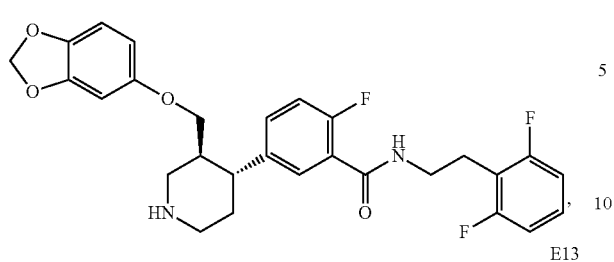
E12
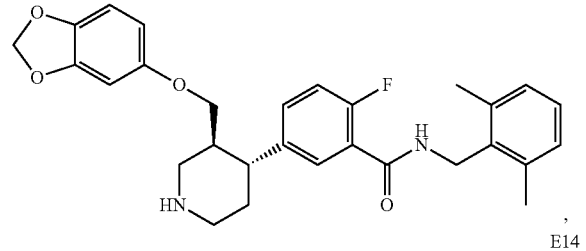
E13
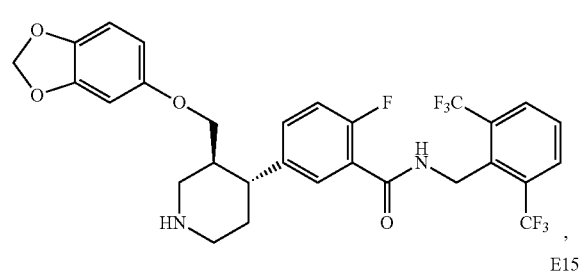
E14
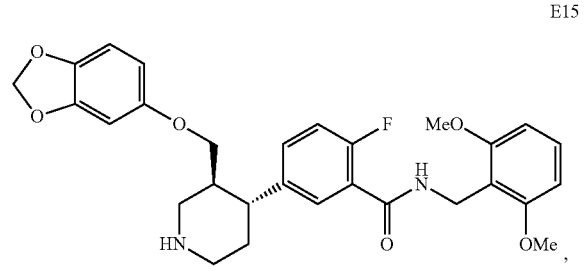
E15
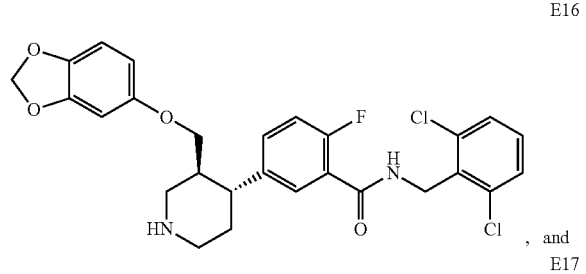
E16
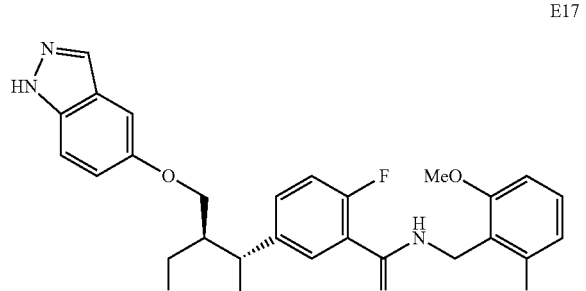
E17
Also provided herein are compounds selected from the group consisting of E1-E17, as described above,
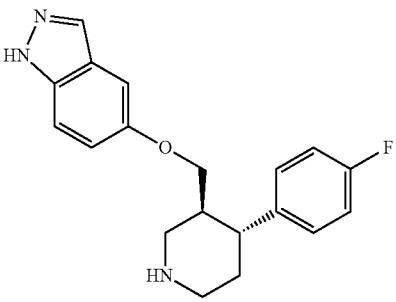
E18
E19
E20
E21
E22
E23

-continued

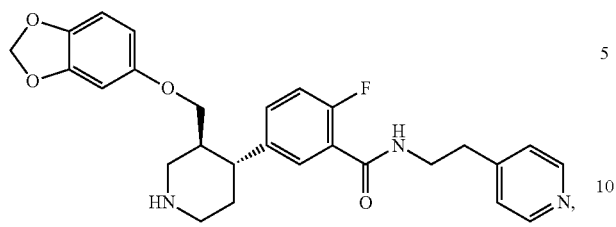
E24

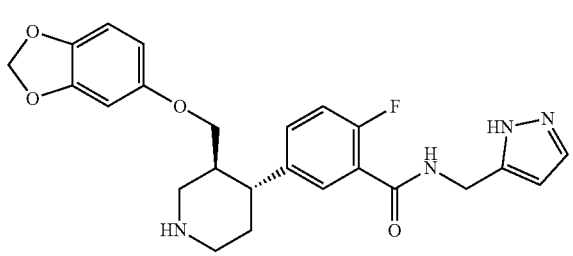
E25

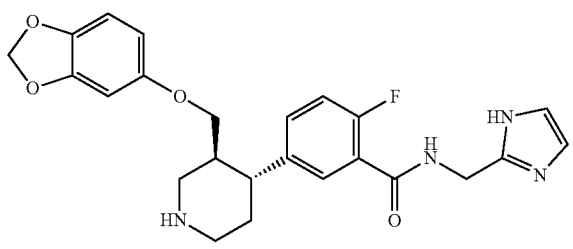
E26

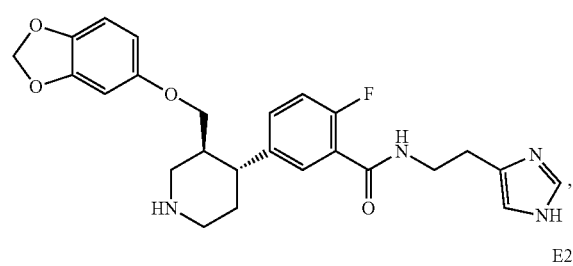
E27

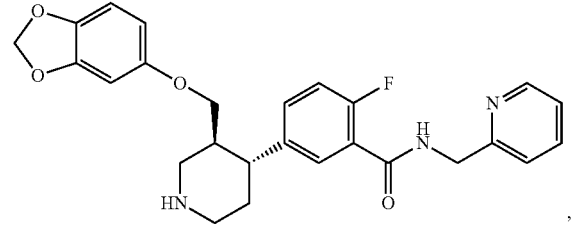
E28

E29

-continued

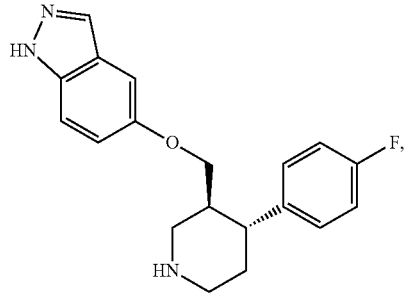
E30

E31

E32

Synthesis of GRK Inhibitors

The compounds described herein are can be synthesized by any method known to one skilled in the art. For example, 4-(4-fluorophenyl)-3-hydroxymethylpiperidine, when appropriately protected on the nitrogen and oxygen, can undergo a lithiation reaction ortho to the fluorine to introduce an aldehyde or carboxylic acid onto the phenyl ring. The carboxylic acid can be converted to an amide in a single step, and the aldehyde can be converted to the homologous carboxymethyl group through reduction, mesylation, cyanation, and hydrolysis. The 3-hydroxymethyl group on the piperidine can be functionalized with sesamol or hydroxyindazole in one or two steps. Additional synthetic procedures for preparing the compounds described herein can be found in the Examples section.

Methods of Use

The compounds described herein (e.g., the compounds of Formulae (I), (I'), (IA'), and pharmaceutically acceptable salts thereof) can inhibit GRK2, GRK5, or both. In some embodiments, the compounds described herein are selective for GRK2 over GRK5, or GRK2 over GRK1. Overexpression of GRK2 has been implicated in a variety of conditions, including heart disease (see e.g., Ungerer Circulation 87:454-463 (1993); Ungerer Circ Res 74: 206-213 (1994)). As such, further provided are methods of treating or preventing heart disease using the compounds disclosed herein.

Thus, one aspect of the disclosure relates to a method of inhibiting GRK2, GRK5, or both comprising contacting the GRK with a compound described herein (e.g., a compound of Formulae (I), (I'), or (IA'), or a pharmaceutical salt thereof), in an amount effective to inhibit the GRK. For example, the GRK can be inhibited in a cell by contacting the cell with a compound described herein (e.g., a compound of Formulae (I), (I'), (IA'), or a pharmaceutically acceptable salt thereof). The cell can be a myocyte, such as a cardiomyocyte. The contacting of the cell can occur in vitro or in vivo. In some cases, contacting of the cell occurs in vitro. In other cases, contacting of the cell occurs in vivo. The compounds described herein can contact a cell in vivo by administering a compound described herein to a subject in need of GRK inhibition, such as GRK2 and/or GRK5 inhibition. Therefore, the disclosure includes administering one or more of a compound described herein to a subject, such as a human, in need thereof. In some embodiments, the subject suffers from heart disease. Specifically contemplated heart diseases include, but are not limited to, cardiac failure, cardiac hypertrophy, hypertension, and a combination thereof.

In view of the above, in various aspects, the disclosure includes a method of treating heart disease in a subject. The method comprises administering a therapeutically effective amount of a compound described herein (e.g., a compound of Formulae (I), (I'), (IA'), or pharmaceutically acceptable salt thereof) to a subject in need of GRK2 and/or GRK5 inhibition, such that GRK2 and/or GRK 5 is inhibited. Conditions resulting from overexpression of GRK2 can include those related to, for example, heart disease (e.g., cardiac failure, cardiac hypertrophy, hypertension, or a combination thereof). Use of a compound described herein (e.g., a compounds of Formulae (I), (I'), (IA'), or a pharmaceutically acceptable salts thereof) to treat a condition resulting from overexpression of GRK2 in a subject, as well as use of a compound described herein (e.g., a compounds of Formulae (I), (I'), (IA'), or a pharmaceutically acceptable salts thereof) in the preparation of a medicament for treating the condition, also are contemplated.

Further guidance for using compounds described herein (e.g., a compound of Formulae (I), (I'), (IA'), or pharmaceutically acceptable salts thereof) for inhibiting GRK can be found in the Examples section, below.

Pharmaceutical Formulations

Also provided herein are pharmaceutical formulations that include a compound described herein (e.g., a compound of Formulae (I), (I'), (IA'), or a pharmaceutically acceptable salts thereof), as previously described herein, and one or more pharmaceutically acceptable excipients.

The compounds described herein can be administered to a subject in a therapeutically effective amount. The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

The compounds disclosed herein can be administered in combination with one or more additional pharmaceutically active compounds/agents. The additional pharmaceutically active compounds/agents may be small molecules or can be macromolecules such as proteins, antibodies, peptibodies, DNA, RNA or fragments of such macromolecules.

The compounds disclosed herein and other pharmaceutically active compounds, if desired, can be administered to a patient or subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds described herein can be administered to a patient or subject at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the patient or subject, the severity of the condition or disease being treated, and the pharmacological activity of the compound being administered. The determination of dosage ranges and optimal dosages for a particular patient or subject is within the ordinary skill in the art.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions might be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention.

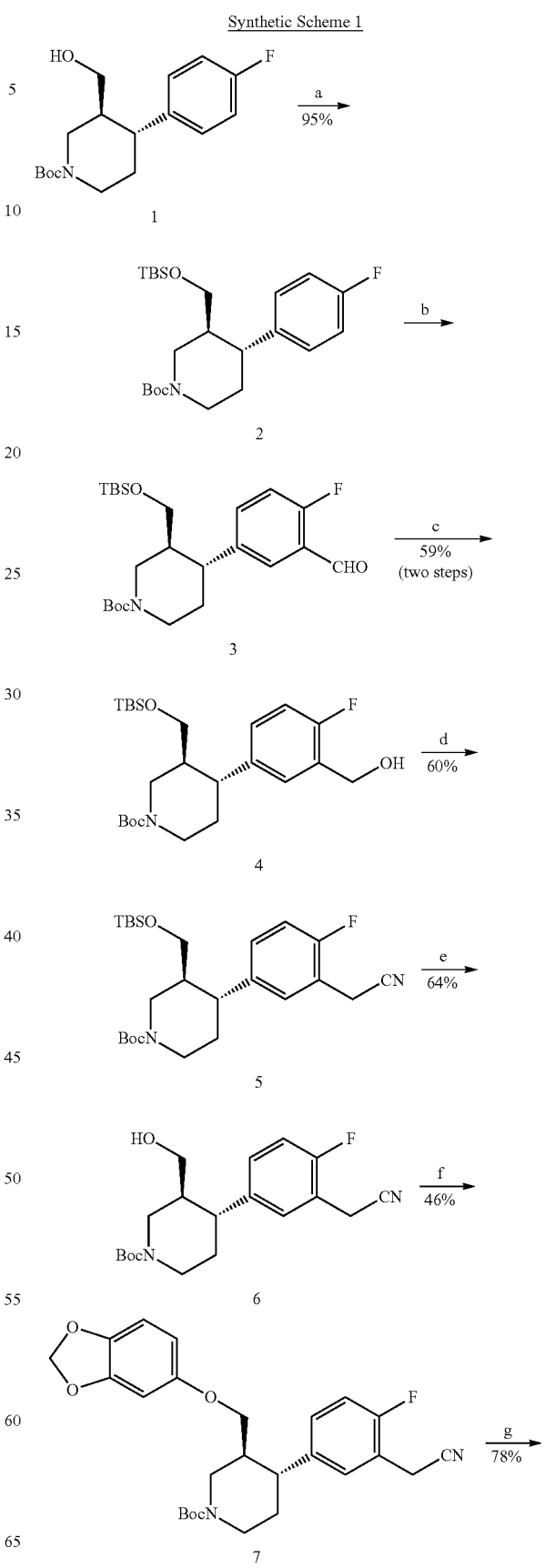

-continued

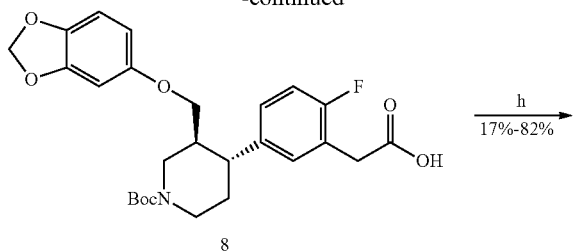

8

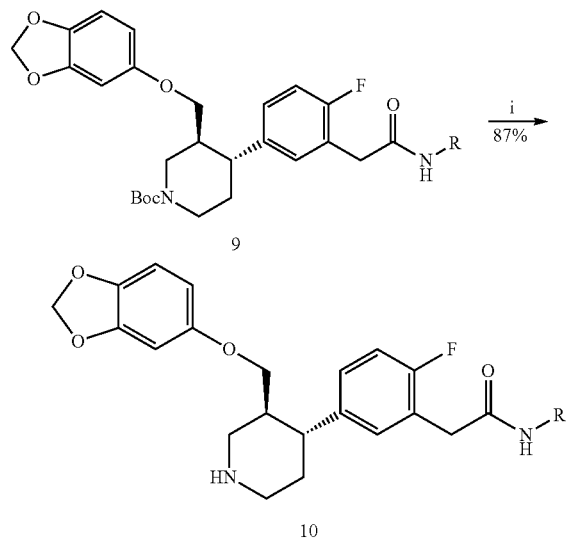

A) TBSCl, DIEA, imidazole, CH₂Cl₂, b) TMEDA, Sec-BuLi, THF, then DMF, c) NaBH₄, THF, MeOH, d) i: Ms₂O, DIEA, CH₂Cl₂, ii: NaCN, DMSO e) TBAF, THF, f) i: Ms₂O, DIEA, CH₂Cl₂, ii: NaH, sesamol, DMF g) NaOH, EtOH, 98° C., h) DIEA, EDC, HOBt, amine, i) 4M HCl/dioxanes Preparation of (3S,4R)-tert-butyl3-(((tert-butyldimethylsilyl)oxy)methyl)-4-(4-fluorophenyl)piperidine-1-carboxylate (2)

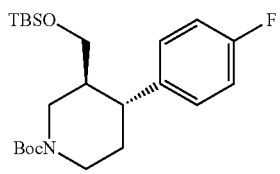 [SMILES: CC(C)(C)OC(=O)N1CC[C@@H](c2ccc(F)cc2)[C@H](CO[Si](C)(C)C(C)(C)C)C1]

(3S,4R)-tert-butyl 4-(4-fluorophenyl)-3-(hydroxymethyl) piperidine-1-carboxylate (1.00 g, 3.23 mmol) dissolved in 32 mL of anhydrous methylene chloride was added to a 100 mL round bottom flask. Tert-butyldimethylsilyl chloride (0.73 g, 4.85 mmol) and imidazole (0.22 g, 3.23 mmol) were added to the reaction vessel producing a cloudy white mixture. Lastly, N,N-diisopropylethylamine (0.85 mL, 4.85 mmol) was added, giving a clear solution. The reaction was stirred overnight at room temperature. Methylene chloride was used to dilute the reaction followed by washing with NaCl (2×). The organic layer was dried over MgSO₄, concentrated in vacuo, and purified using flash chromatography (130 mL silica gel) with a 10%-20% EtOAc/Hexane gradient to give (3S,4R)-tert-butyl-3-(((tert-butyldimethylsilyl)oxy)methyl)-4-(4-fluorophenyl)piperidine-1-carboxylate (1.32 g, TLC R$_f$:0.64 (20% EtOAc/Hexane), 96%). ¹H NMR (DMSO-d₆, 400 MHz) δ: 7.26-7.19 (m, 2H), 7.09 (t, J=8 Hz, 2H), 4.26 (d, J=8.0 Hz, 1H), 4.01 (br s, 1H), 3.46-3.02 (m, 4H), 2.69 (s, 1H), 1.81-1.43 (m, 3H), 1.39 (s, 9H), 0.80 (s, 9H), −0.13 (s, 6H); HPLC purity: 86%; MS (ESI+) m/z: 424.4 (M+1), 446.4 (M+Na⁺).

Preparation of (3S,4R)-tert-butyl-3-(((tert-butyldimethylsilyl)oxy)methyl)-4-(4-fluoro-3-formylphenyl) piperidine-1-carboxylate (3)

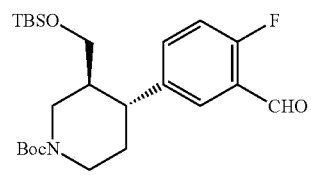 [SMILES: CC(C)(C)OC(=O)N1CC[C@@H](c2ccc(F)c(C=O)c2)[C@H](CO[Si](C)(C)C(C)(C)C)C1]

N1,N1,N2,N2-tetramethylethylene-1,2-diamine (0.548 g, 4.72 mmol) was added to THF (10 mL) in a 50 mL round bottom flask cooled to −78° C. under nitrogen. Sec-buytl-lithium (3.63 mL, 4.72 mmol) was added and the reaction mixture was stirred for ten minutes then (3S,4R)-tert-butyl 3-(((tert-butyldimethylsilyl)oxy)methyl)-4-(4-fluorophenyl) piperidine-1-carboxylate (0.998 g, 2.36 mmol) in THF (10 mL) was added and the solution was stirred at −78° C. for 1 hour. A solution of anhydrous DMF (2 ml) in THF (5 mL) was added and the reaction was allowed to warm to room temperature (4 hours). The reaction was quenched with NH₄Cl (10 mL), extracted with ether 2×, washed with NaCl 3×, dried over MgSO₄, concentrated in vacuo, and purified using flash chromatography with a 1%-10% EtOAc/Hexane gradient to give (3S,4R)-tert-butyl-3-(((tert-butyldimethylsilyl)oxy)methyl)-4-(4-fluoro-3-formyl-phenyl)piperidine-1-carboxylate (1.075 g crude, took all crude to next step, R$_f$:0.46 (10% EtOAc/Hexanes)). ¹H NMR (DMSO-d₆, 400 MHz) δ: 10.20 (s, 1H), 7.71-7.26 (m, 2H), 7.35 (t, J=8.0 Hz, 1H), 4.27 (d, J=12.0 Hz, 1H), 4.05 (br s, 1H), 3.55-3.10 (m, 4H), 2.63-2.55 (m, 1H), 1.83-1.52 (m, 3H), 1.57 (s, 9H), 0.82 (s, 9H), −0.12 (s, 6H); HPLC purity: 95%; MS (ESI+) m/z: 452.4 (M+1).

Preparation of (3S,4R)-tert-butyl-3-(((tert-butyldimethylsilyl)oxy)methyl)-4-(4-fluoro-3-(hydroxymethyl)phenyl)piperidine-1-carboxylate (4)

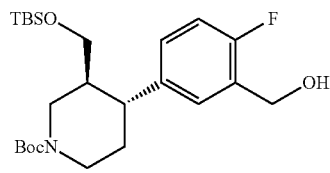 [SMILES: CC(C)(C)OC(=O)N1CC[C@@H](c2ccc(F)c(CO)c2)[C@H](CO[Si](C)(C)C(C)(C)C)C1]

(3S,4R)-tert-butyl 3-(((tert-butyldimethylsilyl)oxy) methyl)-4-(4-fluoro-3-formylphenyl)-peridine-1-carboxylate (crude, 1.075 g, 2.38 mmol) was added to THF (15 mL) in a 50 mL round bottom flask cooled to 0° C. Sodium borohydride (0.0262 g, 1.19 mmol) was added and the reaction mixture was allowed to come to room temperature and stirred 3 hours. Methanol (10 mL) and citric acid (5%, 10 mL) were added to the reaction mixture and allowed to stir 30 minutes. The reaction was extracted with ether/ethyl acetate 2×, washed with NaCl 2×, dried over MgSO₄, concentrated in vacuo, and purified using flash chromatography (80 mL silica gel) of 20% EtOAc/Hexane to give (3S,4R)-tert-butyl 3-(((tert-butyldi-methylsilyl)oxy)methyl)-4-(4-fluoro-3-(hydroxymethyl)phenyl)piperidine-1-carboxylate (0.627 g, $R_f$:0.22 (20% EtOAc/Hexanes), 59% yield from 2). $^1$H NMR (DMSO-$d_6$, 400 MHz) δ: 7.30 (d, J=8.0 Hz, 1H) 7.15-7.08 (m, 1H) 7.05 (t, J=8.0 Hz, 1H), 5.24 (s, 1H), 4.52 (s, 2H), 4.30 (d, J=12.0 Hz, 1H), 4.05 (br s, 1H), 3.35 (s, 1H), 3.24 (s, 1H), 3.14 (t, J=8.0 Hz, 1H), 2.72 (s, 2H), 1.82-1.46 (m, 3H), 1.42 (s, 9H), 0.83 (s, 9H), 0.09 (s, 6H); HPLC purity: 95%; MS (ESI+) m/z: 454.4 (M+1), 476.4 (M+Na$^+$).

Preparation of (3S,4R)-tert-butyl-3-(((tert-butyldimethylsilyl)oxy)methyl)-4-(3-(cyanomethyl)-4-fluorophenyl)piperidine-1-carboxylate (5)

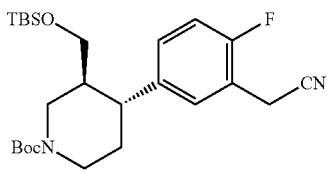

(3S,4R)-tert-butyl 3-(((tert-butyldimethylsilyl)oxy)methyl)-4-(4-fluoro-3-(hydroxymethyl)phenyl)piperidine-1-carboxylate (0.344 g, 0.759 mmol) was added to anhydrous dichloromethane (8 mL) in a 50 mL round bottom flask cooled to 0° C. under nitrogen. Diisopropylethylamine (0.265 mL, 1.517 mmol) was added to the reaction mixture followed by methanesulfonic anhydride and the reaction mixture was stirred for 0.5 hours. The reaction mixture was washed 1× with distilled water, dried over MgSO$_4$, and concentrated in vacuo. Anhydrous dimethyl sulfoxide (8 mL) was added to the 50 mL flask followed by sodium cyanide (0.112 g, 2.276 mmol) and stirred overnight at room temperature under nitrogen. The reaction was diluted with ether and washed with NaCl (6×). The aqueous layers were then washed 2× with ether. The organic layers were combined, dried over MgSO$_4$, concentrated in vacuo, and purified using flash chromatography (30 mL silica gel) of 10-20% gradient of EtOAc/Hexane to give (3S,4R)-tert-butyl-3-(((tert-butyldimethylsilyl)oxy)methyl)-4-(3-(cyanomethyl)-4-fluorophenyl)piperidine-1-carboxylate (0.210 g, $R_f$:0.51 (20% EtOAc/Hexanes), 60% yield). $^1$H NMR (CDCl$_3$, 400 MHz) δ: 7.25-7.18 (m, 1H) 7.13 (s, 1H) 7.03 (t, J=9.0 Hz, 1H), 4.37-4.16 (m, 2H), 3.74 (s, 2H), 3.37-3.23 (m, 1H), 3.19-3.08 (m, 1H), 2.68 (br s, 2H), 1.82-1.56 (m, 4H), 1.48 (s, 9H), 1.24 (s, 9H), −0.07 (s, 6H); HPLC purity: 99%; MS (ESI+) m/z: 463.1 (M+1), 485.1 (M+Na$^+$).

Preparation of (3S,4R)-tert-butyl-4-(3-(cyanomethyl)-4-fluorophenyl)-3-(hydroxymethyl)piperidine-1-carboxylate (6)

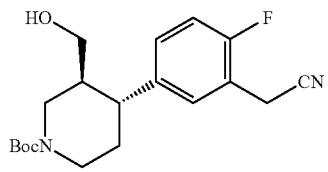 [SMILES: CC(C)(C)OC(=O)N1CC[C@@H](c2ccc(F)c(CC#N)c2)[C@H](CO)C1]

(3S,4R)-tert-butyl 3-(((tert-butyldimethylsilyl)oxy)methyl)-4-(3-(cyanomethyl)-4-fluorophenyl)piperidine-1-carboxylate (0.501 g, 1.081 mmol) and tetra-n-butyl ammonium fluoride (1.30 mL, 1.30 mmol) were added to THF (10 mL) in a 50 mL round bottom flask at room temperature and allowed to stir overnight. The next day another equivalent of tetra-n-butylammonium fluoride (1.30 mL, 1.30 mmol) was added to the reaction mixture and stirred for 3.0 hours. The reaction mixture was quenched with NH$_4$Cl, extracted with ether/ethyl acetate 1× and washed with NaCl (2×). The organic layers were combined, dried over MgSO$_4$, concentrated in vacuo, and purified using flash chromatography (25 mL silica gel) of 30-50% gradient of EtOAc/Hexane to give (3S,4R)-tert-butyl-4-(3-(cyanomethyl)-4-fluorophenyl)-3-(hydroxymethyl) piperidine-1-carboxylate (0.240 g, $R_f$:0.33 (30% EtOAc/Hexanes), 64% yield). $^1$H NMR (CDCl$_3$, 400 MHz) δ: 7.24 (dd, J$_1$=2.4 Hz, J$_2$=7.2 Hz, 1H) 7.18-7.12 (m, 1H) 7.03 (t, J=9.0 Hz, 1H), 4.41-4.32 (m, 2H), 4.19 (br s, 1H), 3.74 (s, 1H), 3.42 (dd, J$_1$=3.0 Hz, J$_2$=11.0 Hz, 1H), 3.24 (q, J=6.4 Hz, 1H), 2.87-2.52 (m, 3H), 1.87-1.57 (m, 4H), 1.48 (s, 9H); HPLC purity: 89%; MS (ESI+) m/z: 349.3 (M+1), 371.3 (M+Na$^+$).

Preparation of (3S,4R)-tert-butyl 3-((benzo[d][1,3]dioxol-5-yloxy)methyl)-4-(3-(cyanomethyl)-4-fluorophenyl)piperidine-1-carboxylate (7)

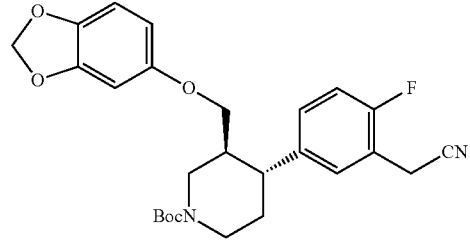 [SMILES: CC(C)(C)OC(=O)N1CC[C@@H](c2ccc(F)c(CC#N)c2)[C@H](COc2ccc3c(c2)OCO3)C1]

(3S,4R)-tert-butyl-4-(3-(cyanomethyl)-4-fluorophenyl)-3-(hydroxymethyl)piperidine-1-carboxylate was added to a dry 25 mL round bottom flask, with 5 mL anhydrous dichloromethane cooled to 0° C. followed by DIEA (0.346 mL, 1.979 mmol) and lastly, methanesulfonic anhydride (0.230 g, 1.319 mmol) and stirred for 2 hours. The reaction mixture was washed 1× with NaCl, dried of MgSO$_4$, and concentrated in vacuo. To a separate 25 mL round bottom flask sodium hydride (0.058 g, 1.451 mmol) was added with DMF under nitrogen at 0° C. followed by sesamol (0.1913 g, 1.385 mmol) in 2 mL DMF and stirred for 20 minutes. The dried, mesylated (3S,4R)-tert-butyl-4-(3-(cyanomethyl)-4-fluorophenyl)-3-(hydroxymethyl)piperidine-1-carboxylate was then added with 2 mL DMF to the reaction vessel with the activated sesamol, heated to 70° C., and stirred for 10 minutes. The reaction was quenched with NH$_4$Cl, extracted with EtOAc/ether 2×, washed with brine 3×, dried over MgSO$_4$ and purified using flash chromatography with a 0% to 80% gradient of EtOAc/Hexanes to give (3S,4R)-tert-butyl 3-((benzo[d][1,3]dioxol-5-yloxy)methyl)-4-(3-(cyanomethyl)-4-fluorophenyl) piperidine-1-carboxylate (0.138 g, Rf: 0.40 (40% EtOAc/Hexanes), 46% yield). $^1$H NMR (CDCl$_3$, 400 MHz) δ: 7.25-7.21 (m, 1H), 7.16-7.12 (m, 1H), 7.02 (t, J=8.8 Hz, 1H), 6.63 (d, J=8.8, 1H), 6.35 (d, J=2.4, 1H), 6.14 (dd, J$_1$=2.4 Hz, J$_2$=8.4 Hz, 1H), 5.88 (s, 2H), 4.43 (broad s, 1H), 4.25 (broad s, 1H), 3.72 (s, 2H), 3.62-3.59 (m, 1H), 3.46-3.42 (m, 1H), 2.90-2.67 (m, 3H), 2.10-1.60 (m, 3H), 1.50 (s, 9H); HPLC purity: 98%; MS (ESI+) m/z: 469.1 (M+1), 491.1 (M+Na⁺).

Preparation of 2-(5-((3S,4R)-3-((benzo[d][1,3]dioxol-5-yloxy)methyl)-1-(tert-butoxycarbonyl) piperidin-4-yl)-2-fluorophenyl)acetic acid (8)

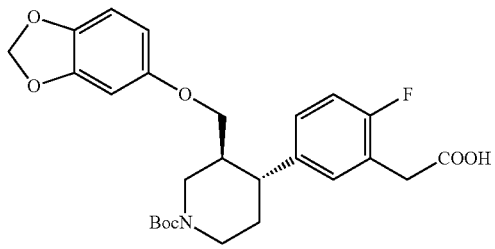 [SMILES: CC(C)(C)OC(=O)N1CC[C@@H](c2ccc(F)c(CC(=O)O)c2)[C@H](COc2ccc3c(c2)OCO3)C1]

(3S,4R)-tert-butyl 3-((benzo[d][1,3]dioxol-5-yloxy)methyl)-4-(3-(cyanomethyl)-4-fluorophenyl) piperidine-1-carboxylate (0.459 g) in EtOH (3.0 mL) was added to a 25 mL pressure vessel followed by 50% NaOH (0.26 mL) and heated to 98° C. overnight. The following day further excess 50% NaOH (0.10 mL) was added and the reaction was again stirred overnight. The reaction mixture was cooled to room temperature and diluted with H₂O then 2N HCl was added to reach pH 2.0. The resulting suspension was extracted with dichloromethane 3×, washed with NaCl 2×, dried with MgSO₄, and concentrated in vacuo to give 2-(5-((3S,4R)-3-((benzo[d][1,3]dioxol-5-yloxy)methyl)-1-(tert-butoxycarbonyl)piperidin-4-yl)-2-fluorophenyl)acetic acid without further purification (0.372 g, 78% yield). ¹H NMR (CDCl₃, 400 MHz) δ: 7.11-7.04 (m, 2H), 7.00 (t, J=9.0 Hz, 1H), 6.20 (d, J=8.8, 1H), 6.34 (2, 1H), 6.14 (d, J=8.4 Hz, 1H), 5.88 (s, 2H), 4.42 (broad s, 1H), 4.23 (broad s, 1H), 3.66 (s, 2H), 3.64-3.58 (m, 1H), 3.48-3.42 (m, 1H), 2.88-2.72 (m, 2H), 2.71-2.60 (m, 1H), 2.04-1.92 (m, 1H), 1.85-1.63 (m, 3H), 1.49 (s, 9H); HPLC purity: 87%; MS (ESI+) m/z: 488.2 (M+1), 410.2 (M+Na⁺); (ESI−) m/z: 486.2 (M−1).

Preparation of (3S,4R)-tert-butyl 3-((benzo[d][1,3] dioxol-5-yloxy)methyl)-4-(3-(2-((2,6-difluorobenzyl)amino)-2-oxoethyl)-4-fluorophenyl)piperidine-1-carboxylate (9a)

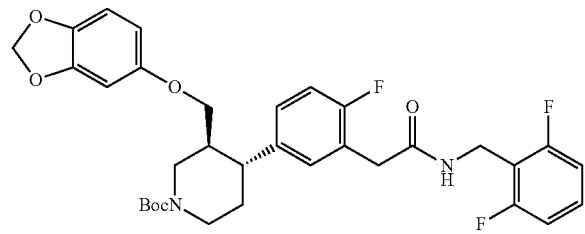 [SMILES: CC(C)(C)OC(=O)N1CC[C@@H](c2ccc(F)c(CC(=O)NCc3c(F)cccc3F)c2)[C@H](COc2ccc3c(c2)OCO3)C1]

2-(5-((3S,4R)-3-((benzo[d][1,3]dioxol-5-yloxy)methyl)-1-(tert-butoxycarbonyl)piperidin-4-yl)-2-fluorophenyl)acetic acid (0.100 g, 0.205 mmol), 1-Ethyl-3-(3-dimethylaminopropyl)carbodiimide (0.045 g, 0.287 mmol), N,N-diisopropylethylamine (0.036 mL, 0.205 mmol), 4-diethylaminopyridine (0.013 g, 0.103 mmol), and 2,6-difluorobenzylamine (0.049 mL, 0.410 mmol) were added to THF (5 mL) in a 15 mL round bottom flask and stirred overnight at room temperature. Diluted with ethyl acetate and saturated sodium bicarbonate and then separated the layers. The organic layer was then washed with 10% citric acid (1×), brine (2×), dried with MgSO₄, and concentrated in vacuo. Purified using flash chromatography in a gradient of 40%-90% EtOAc/Hexanes to give as an oil (3S,4R)-tert-butyl 3-((benzo[d][1,3]dioxol-5-yloxy)methyl)-4-(3-(2-((2, 6-difluorobenzyl)amino)-2-oxoethyl)-4-fluorophenyl)piperidine-1-carboxylate (0.046 g, 36% yield). MS (ESI+) m/z: 613.1 (M+1), 635.1 (M+Na⁺).

The following intermediates 9b-f were prepared in a manner analogous to that used for Intermediate 9a using the appropriate amines instead of 2,6-difluorobenzylamine.

Preparation of (3S,4R)-tert-butyl 3-((benzo[d][1,3] dioxol-5-yloxy)methyl)-4-(3-(2-((2,6-difluorophenethyl)amino)-2-oxoethyl)-4-fluorophenyl)piperidine-1-carboxylate (9b)

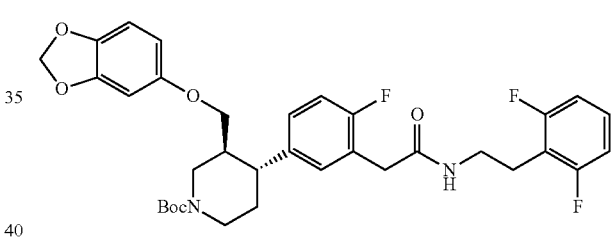

¹H NMR (CDCl₃, 400 MHz) δ: 7.19, 7.13-7.07, 6.97, 6.61, 6.33, 6.13, 5.86, 5.58, 4.43, 4.24, 3.60, 3.51-3.40, 2.92-2.73, 2.66, 2.00, 1.77, 1.70, 1.50.

Preparation of (3S,4R)-tert-butyl 3-((benzo[d][1,3] dioxol-5-yloxy)methyl)-4-(4-fluoro-3-(2-oxo-2-((pyridin-2-ylmethyl)amino)ethyl)phenyl)piperidine-1-carboxylate (9c)

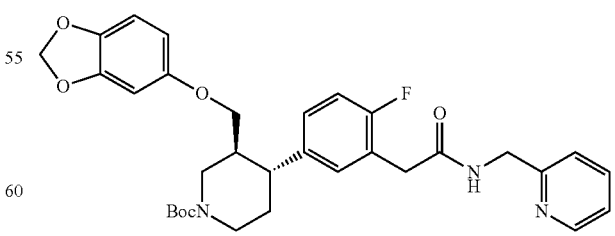

¹H NMR (CDCl₃, 400 MHz) δ: 8.44, 7.65, 7.24, 7.18-7.12, 7.07, 6.99, 6.89, 6.60, 6.33, 6.13, 5.87, 4.52, 4.43, 4.24, 3.66-3.60, 3.49-3.42, 2.89-2.71, 2.66, 2.13, 2.01, 1.89-1.78, 1.69, 1.49.

(3S,4R)-tert-butyl 3-((benzo[d][1,3]dioxol-5-yloxy)methyl)-4-(4-fluoro-3-(2-((2-methoxybenzyl)amino)-2-oxoethyl)phenyl)piperidine-1-carboxylate (9d)

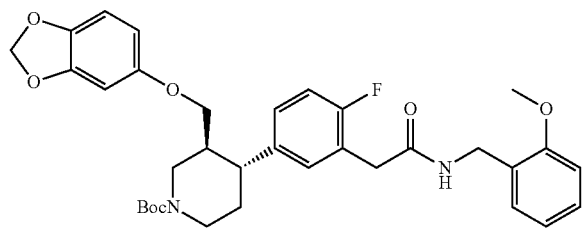 [SMILES: COc1ccccc1CNC(=O)Cc1cc([C@@H]2CCN(C(=O)OC(C)(C)C)C[C@H]2COc2ccc3c(c2)OCO3)ccc1F]

¹H NMR (CDCl₃, 400 MHz) δ: 7.24, 7.20, 7.11-7.04, 6.98, 6.88, 6.83, 6.61, 6.33, 6.12, 6.04, 5.87, 4.42-4.39, 4.23, 3.75, 3.65-3.44, 3.41, 2.78, 2.63, 1.98, 1.879-1.63, 1.50.

(3S,4R)-tert-butyl 3-((benzo[d][1,3]dioxol-5-yloxy)methyl)-4-(4-fluoro-3-(2-oxo-2-((2-(pyridin-2-yl)ethyl)amino)ethyl)phenyl)piperidine-1-carboxylate (9e)

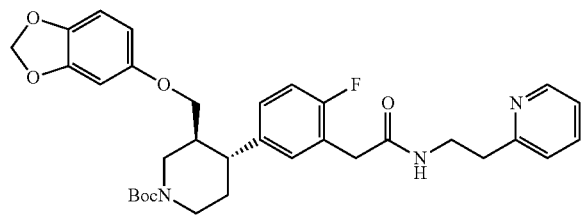 [SMILES: CC(C)(C)OC(=O)N1CC[C@@H](c2ccc(F)c(CC(=O)NCCc3ccccn3)c2)[C@H](COc2ccc3c(c2)OCO3)C1]

¹H NMR (CDCl₃, 400 MHz) δ: 8.40, 7.75, 7.05, 6.91, 6.58, 6.31, 6.09, 5.84, 4.40, 4.21, 3.59-3.34, 2.99, 2.76, 2.62, 2.00, 1.75-1.58, 1.48.

(3S,4R)-tert-butyl 4-(3-(2-((2-(1H-pyrazol-4-yl)ethyl)amino)-2-oxoethyl)-4-fluorophenyl)-3-((benzo[d][1,3]dioxol-5-yloxy)methyl)piperidine-1-carboxylate (9f)

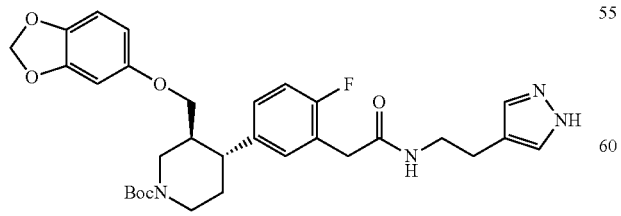

¹H NMR (CDCl₃, 400 MHz) δ: 7.32, 7.09-7.03, 6.98, 6.62, 6.33, 5.87, 5.55, 4.42, 4.24, 3.62-3.47, 3.41, 2.79, 2.65, 1.94, 1.81-1.72, 1.51.

Example 1: 2-(5-((3S,4R)-3-((benzo[d][1,3]dioxol-5-yloxy)methyl)piperidin-4-yl)-2-fluorophenyl)-N-(2,6-difluorobenzyl)acetamide hydrochloride (CCG 208945) (E01)

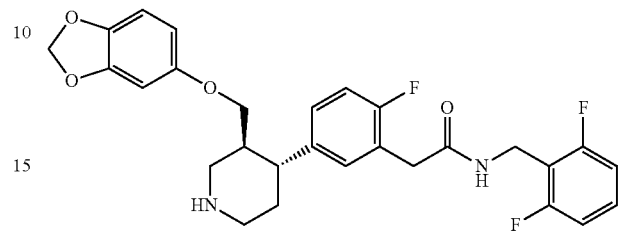

(3S,4R)-tert-butyl 3-((benzo[d][1,3]dioxol-5-yloxy)methyl)-4-(3-(2-((2,6-difluorobenzyl)amino)-2-oxoethyl)-4-fluorophenyl)piperidine-1-carboxylate was added to dioxane (0.5 mL) followed by 4M HCl/dioxane (0.186 mL) and stirred at room temperature for one hour. The reaction was concentrated in vacuo, then diethyl ether was added to precipitate a white solid which was then concentrated to give 2-(5-((3S,4R)-3-((benzo[d][1,3]dioxol-5-yloxy)methyl)piperidin-4-yl)-2-fluorophenyl)-N-(2,6-difluorobenzyl)acetamide as a white solid (0.032 g, 0.057 mmol, 87% yield). ¹H NMR (DMSO, 500 MHz) δ: 8.52, 7.39, 7.16-7.12, 7.08, 6.73, 6.48, 6.18, 5.92, 4.32, 3.57, 3.50-3.40, 3.28, 3.17, 2.91-2.79, 2.72, 2.34, 1.90, 1.81-1.74.

The following Examples 2-6 were prepared from Intermediates 9b-f in a manner analogous to that described for Example 1.

Example 2: 2-(5-((3S,4R)-3-((benzo[d][1,3]dioxol-5-yloxy)methyl)piperidin-4-yl)-2-fluorophenyl)-N-(2,6-difluorophenethyl)acetamide hydrochloride (CCG 215086) (E02)

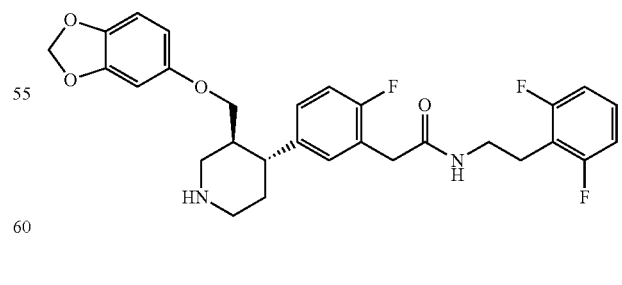

¹HNMR (DMSO, 500 MHz) δ: 8.20, 7.29, 7.17-6.97, 6.68, 6.43, 6.14, 5.88, 3.56-3.29, 3.22, 3.18-3.09, 2.73, 2.61, 2.49, 2.12, 1.70.

Example 3: 2-(5-((3S,4R)-3-((benzo[d][1,3]dioxol-5-yloxy)methyl)piperidin-4-yl)-2-fluorophenyl)-N-(2-(pyridin-2-yl)ethyl)acetamide hydrochloride (CCG 215142) (E03)

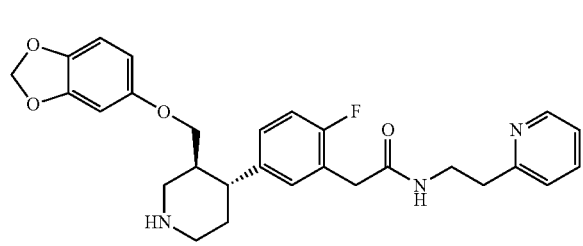 [SMILES: O=C(Cc1cc([C@@H]2CCNC[C@H]2COc2ccc3c(c2)OCO3)ccc1F)NCCc1ccccn1]

¹HNMR (MeOD, 500 MHz) δ: 8.70, 8.43, 7.87, 7.20, 7.043, 6.63, 6.40, 6.20, 5.85, 5.49, 3.71-3.42, 3.22, 3.15, 2.98-2.79, 2.43, 2.04, 1.29.

Example 4: N-(2-(1H-pyrazol-4-yl)ethyl)-2-(5-((3S, 4R)-3-((benzo[d][1,3]dioxol-5-yloxy)methyl)piperidin-4-yl)-2-fluorophenyl)acetamide hydrochloride (CCG 222886) (E04)

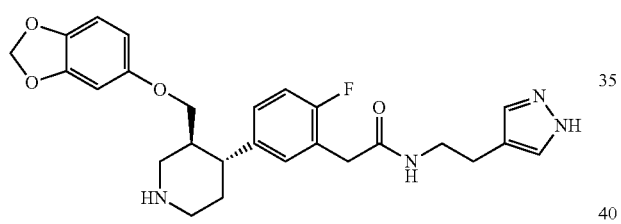

¹HNMR (DMSO, 400 MHz) δ: 9.18, 8.19, 7.61, 7.14, 7.11, 6.73, 6.50, 6.19, 5.92, 3.63-3.56, 3.55-3.46, 3.44, 3.37, 3.22, 3.17, 2.96, 2.80, 2.58, 2.46-2.38, 1.98, 1.9-1.82.

Example 5: 2-(5-((3S,4R)-3-((benzo[d][1,3]dioxol-5-yloxy)methyl)piperidin-4-yl)-2-fluorophenyl)-N-(pyridin-2-ylmethyl)acetamide hydrochloride (CCG215143) (E05)

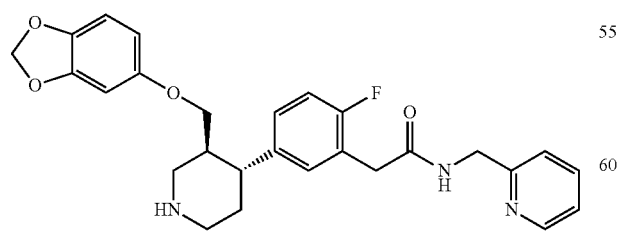

¹HNMR (CD₃O₃, 400 MHz) δ: 8.75, 8.53, 8.02-7.88, 7.30, 7.21, 7.07, 6.61, 6.39, 6.18, 5.85, 3.72, 3.71-3.46, 3.15, 3.01-2.89, 2.45, 2.05.

Example 6: 2-(5-((3S,4R)-3-((benzo[d][1,3]dioxol-5-yloxy)methyl)piperidin-4-yl)-2-fluorophenyl)-N-(2-methoxybenzyl)acetamide hydrochloride (CCG 215140) (E06)

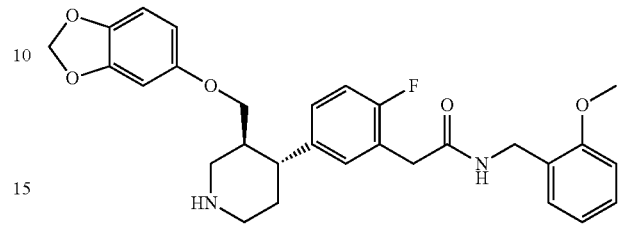

¹HNMR (CDCl₃, 400 MHz) δ: 9.89, 7.25-7.11, 7.01, 6.89, 6.83, 6.61, 6.33, 6.13-6.03, 5.88, 4.39, 3.77, 3.72-3.39, 3.13, 3.03, 2.89, 2.64, 2.37, 2.03, 1.61.

Synthetic Scheme 2

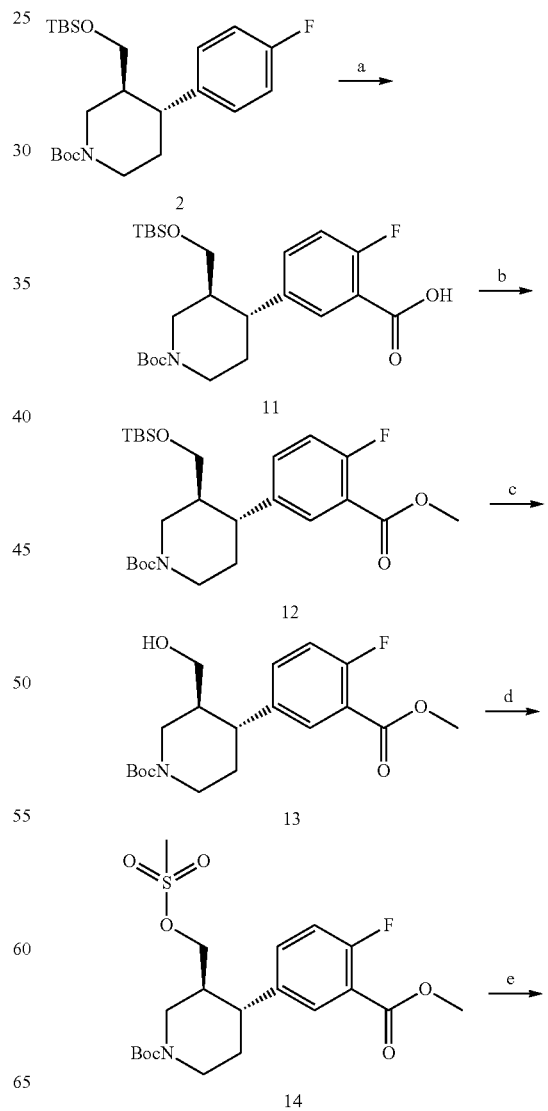

-continued

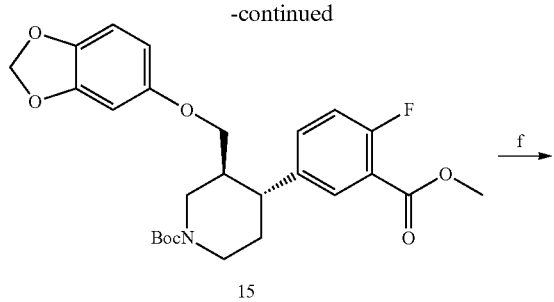

15

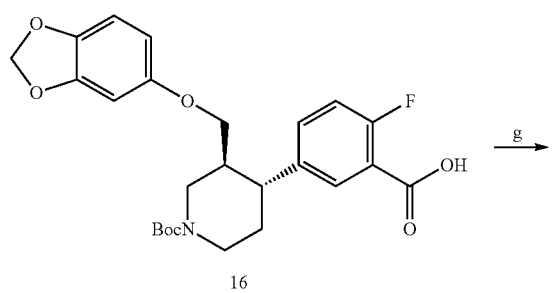

16

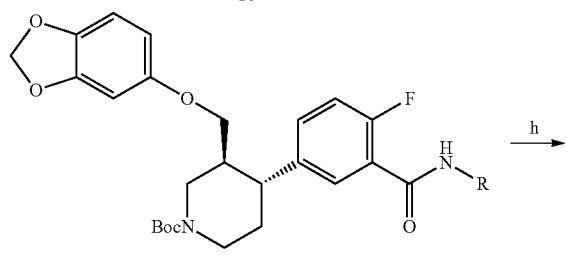

17

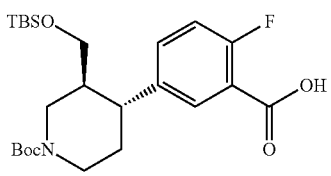 [SMILES: CC(C)(C)OC(=O)N1CC[C@@H](c2ccc(F)c(C(=O)O)c2)[C@H](CO[Si](C)(C)C(C)(C)C)C1]

18 a) TMEDA, Sec-BuLi, THF, then CO$_2$, b) TMS-diazomethane, 20% MeOH/Toluene, c) TBAF, AcOH, THF, 60° C., d) Ms$_2$O, DIEA, CH$_2$Cl$_2$ e) NaH, sesamol, DMF, f) NaOH, MeOH, H$_2$O, g) DIEA, EDC, HOBt, amine, h) 4M HCl/dioxanes Preparation of 5-((3S,4R)-1-(tert-butoxycarbonyl)-3-(((tert-butyldimethylsilyl)oxy)methyl)piperidin-4-yl)-2-fluorobenzoic acid (11)

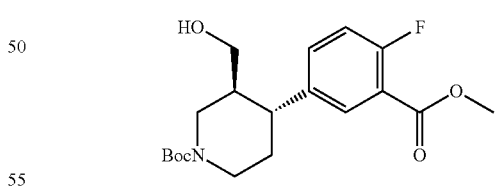

N1,N1,N2,N2-tetramethylethylene-1,2-diamine (0.549 g, 4.72 mmol) was added to THF (10 mL) in a 50 mL round bottom flask cooled to −78° C. under argon. Sec-buytl-lithium (3.63 mL, 4.72 mmol) was added and the reaction mixture was stirred for thirty minutes then (3S,4R)-tert-butyl 3-(((tert-butyldimethyl silyl)oxy)methyl)-4-(4-fluorophenyl)piperidine-1-carboxylate (1.0 g, 2.36 mmol) in THF (10 mL) was added and the solution was stirred at −78° C. for 1 hour. Freshly broken CO$_2$ was added and the mixture allowed to warm to room temperature. The reaction was extracted with ether 2×, washed with NaCl 2×, dried with MgSO$_4$ and concentrated in vacuo. The resulting intermediate was used without further purification.

Preparation of (3S,4R)-tert-butyl 3-(((tert-butyldimethylsilyl)oxy)methyl)-4-(4-fluoro-3-(methoxycarbonyl)phenyl) piperidine-1-carboxylate (12)

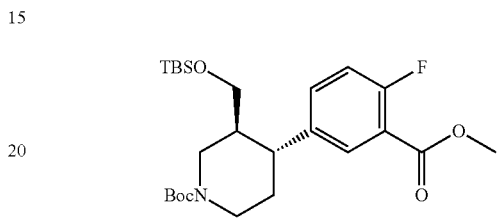

To a solution of 5-((3S,4R)-1-(tert-butoxycarbonyl)-3-(((tert-butyldimethylsilyl)oxy)methyl)piperidin-4-yl)-2-fluorobenzoic acid (1.08 g, 2.31 mmol) in 20% (V/V) Methanol/toluene (30 mL) was added drop wise TMS-diazomethane (1.27 mL, 2.54 mmol). Gas evolved and reaction is slightly yellow. The reaction was stirred for 30 minutes and was then quenched with acetic acid until gas no longer evolved and the yellow color was gone. Then the reaction was concentrated in vacuo. Dissolved in ethyl acetate and ether and washed 2× with brine, dried with MgSO$_4$ and concentrated. The crude product was purified using flash chromatography with a 20%-30% EtOAc/Hexane gradient to give (3S,4R)-tert-butyl 3-(((tert-butyldimethylsilyl)oxy)methyl)-4-(4-fluoro-3-(methoxycarbonyl)phenyl) piperidine-1-carboxylate (0.96 g crude, 1.99 mmol, 86% yield over two steps). $^1$H NMR (DMSO-d$_6$, 400 MHz) δ: 7.69, 7.59-7.53, 7.29, 4.25, 4.02, 3.84, 3.23, 3.14, 2.74, 2.58, 1.81-1.51, 1.42, 0.82, −0.10.

Preparation of (3S,4R)-tert-butyl 4-(4-fluoro-3-(methoxycarbonyl)phenyl)-3-(hydroxymethyl)piperidine-1-carboxylate (13)

To a solution of (3S,4R)-tert-butyl 3-(((tert-butyldimethylsilyl)oxy)methyl)-4-(4-fluoro-3-(methoxycarbonyl)phenyl) piperidine-1-carboxylate (1.68 g, 3.49 mmol) in THF (50 mL) was added acetic acid (0.60 mL, 10.46 mmol) followed by tetrabutylammonium fluoride (1.0 M, 10.46 mL, 10.46 mmol). The resulting mixture was stirred overnight at 60° C. Diluted with ethyl acetate/ether and treated with saturated aq. NH$_4$Cl. The layers were separated and the organic layer was washed with NaCl (2×), dried with MgSO$_4$, and concentrated in vacuo. Purified using flash chromatography with a 10%-30% EtOAc/Hexane gradient to give (3S,4R)-tert-butyl 4-(4-fluoro-3-(methoxycarbonyl)phenyl)-3-(hydroxymethyl)piperidine-1-carboxylate as a clear oil (1.29 g, 3.51 mmol, 100% yield). ¹H NMR (DMSO-d₆, 400 MHz) δ: 7.69, 7.54, 7.28, 4.47, 4.26, 3.99, 3.85, 3.09, 2.96, 2.75, 2.57, 1.69, 1.52 1.42.

Preparation of (3S,4R)-tert-butyl 4-(4-fluoro-3-(methoxycarbonyl)phenyl)-3-(((methylsulfonyl)oxy)methyl)piperidine-1-carboxylate) (14)

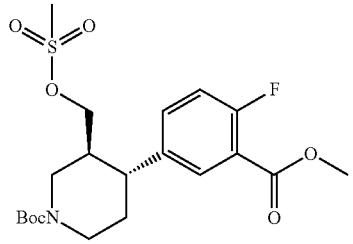 [SMILES: COC(=O)c1cc([C@@H]2CCN(C(=O)OC(C)(C)C)C[C@H]2COS(C)(=O)=O)ccc1F]

To a 0° C. solution of (3S,4R)-tert-butyl 4-(4-fluoro-3-(methoxycarbonyl) phenyl)-3-(hydroxymethyl)piperidine-1-carboxylate (0.687 g, 1.87 mmol) in 25 mL DCM was added diisopropylethylamine (0.980 mL, 5.61 mmol) followed by methanesulfonylchloride (0.651 g, 3.74 mmol). The reaction was allowed to warm to room temperature and stirred overnight. The resulting product was washed with water (1×), then brine (1×), dried over MgSO₄, and concentrated in vacuo to give a clear oil (0.833 g crude). The product was used in subsequent reactions without further purification.

Preparation of (3S,4R)-tert-butyl 3-((benzo[d][1,3]dioxol-5-yloxy)methyl)-4-(4-fluoro-3-(methoxycarbonyl)phenyl) piperidine-1-carboxylate (15)

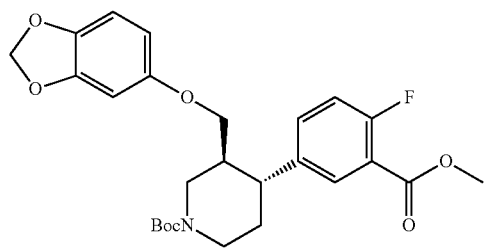 [SMILES: COC(=O)c1cc([C@@H]2CCN(C(=O)OC(C)(C)C)C[C@H]2COc2ccc3c(c2)OCO3)ccc1F]

To a 0° C. solution of benzo[d][1,3]dioxol-5-ol (0.543 g, 3.93 mmol) in 5 mL DMF was added 60% sodium hydride in mineral oil (0.164 g, 4.11 mmol). The solution turned light pink and was stirred for five minutes. To the reaction was added (3S,4R)-tert-butyl 4-(4-fluoro-3-(methoxycarbonyl)phenyl)-3-(((methylsulfonyl)oxy)methyl)piperidine-1-carboxylate (0.833 g, 1.87 mmol) in 5 mL DMF. The reaction was heated to 70° C. for 1 hour then cooled to room temperature and treated with sat. NH₄Cl solution. Extracted with ethyl acetate/ether (2×), washed with brine, dried with MgSO₄, and concentrated in vacuo. The crude product was purified by flash chromatography using a gradient of 5% MeOH/DCM to give as a clear oil (3S,4R)-tert-butyl 3-((benzo[d][1,3]dioxol-5-yloxy)methyl)-4-(4-fluoro-3-(methoxycarbonyl)phenyl)piperidine-1-carboxylate (0.452 g, 0.927 mmol, 50% yield over two steps). ¹H NMR (DMSO, 400 MHz) δ: 7.72, 7.58, 7.28, 6.72, 6.45, 6.17, 5.92, 4.92, 4.04, 3.83, 3.55-3.47, 2.91-2.55, 2.05, 1.72, 1.61, 1.43.

Preparation of 5-((3S,4R)-3-((benzo[d][1,3]dioxol-5-yloxy)methyl)-1-(tert-butoxycarbonyl)piperidin-4-yl)-2-fluorobenzoic acid (16)

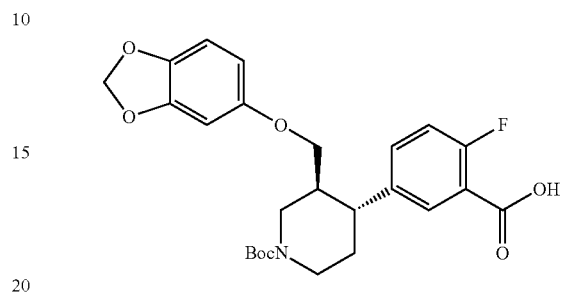

To a round bottom flask equipped with a stir bar was added (3S,4R)-tert-butyl 3-((benzo[d][1,3]dioxol-5-yloxy)methyl)-4-(4-fluoro-3-(methoxycarbonyl)phenyl)piperidine-1-carboxylate (0.297 g, 0.608 mmol), 1M NaOH (1.83 mL, 1.825 mmol), H₂O (5 mL), and Methanol (12 mL). The reaction was stirred overnight at room temperature. Ether was added to the reaction and the resulting layers were separated. To the aqueous layer, 10% citric acid was added to give a pH of 4. The aqueous layer was then extracted 2× with ethyl acetate. The ethyl acetate layers were then combined and washed 1× with NaCl, dried with MgSO₄, and concentrated to give, with no further purification, as an amorphous solid 5-((3S,4R)-3-((benzo[d][1,3]dioxol-5-yloxy)methyl)-1-(tert-butoxycarbonyl)piperidin-4-yl)-2-fluorobenzoic acid (0.226 g, 0.477 mmol, 79% yield). ¹H NMR (DMSO, 400 MHz) δ: 13.21, 7.70, 7.57-7.51, 7.23, 6.72, 6.46, 6.17, 5.92, 4.30, 4.04, 3.53-3.48, 2.83-2.60, 2.03, 1.75-1.68, 1.59, 1.43.

Preparation of (3S,4R)-tert-butyl 3-((benzo[d][1,3]dioxol-5-yloxy)methyl)-4-(4-fluoro-3-((pyridin-2-ylmethyl)carbamoyl)phenyl)piperidine-1-carboxylate (17a)

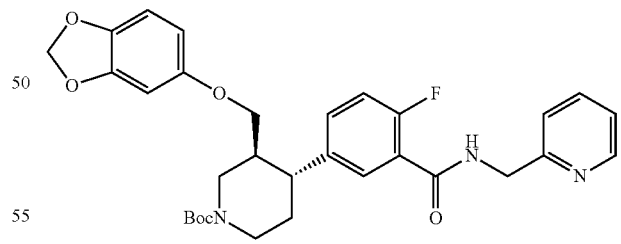

5-((3S,4R)-3-((benzo[d][1,3]dioxol-5-yloxy)methyl)-1-(tert-butoxycarbonyl)piperidin-4-yl)-2-fluorobenzoic acid (0.100 g, 0.211 mmol), 1-ethyl-3-(3-dimethylaminopropyl) carbodiimide (0.066 g, 0.422 mmol), N,N-diisopropylethylamine (0.074 mL, 0.422 mmol), hydroxybenzotriazole (0.057 g, 0.422 mmol), and pyridin-2-ylmethanamine (0.044 mL, 0.422 mmol) were added to THF (5 mL) in a 15 mL round bottom flask and stirred overnight at room temperature. The resulting solution was diluted with ethyl acetate and saturated sodium bicarbonate, and then the layers were separated. The organic layer was then washed with brine (2×), dried with MgSO$_4$, and concentrated in vacuo. The crude product was purified using flash chromatography using 70% EtOAc/Hexanes to give as a clear oil (3S,4R)-tert-butyl 3-((benzo[d][1,3]dioxol-5-yloxy)methyl)-4-(4-fluoro-3-((pyridin-2-ylmethyl)carbamoyl)phenyl)piperidine-1-carboxylate (0.088 g, 0.155 mmol, 74% yield). $^1$H NMR (CDCl$_3$, 400 MHz) δ: 8.56, 8.02-7.93, 7.70-7.62, 7.35-7.24, 7.20, 7.05, 6.60, 6.33, 6.11, 5.85, 4.78, 4.44, 4.23, 3.58, 3.44, 2.86-2.67, 2.15-2.04, 1.83-1.65, 1.48.

The following intermediates 17b-j were prepared in a manner analogous to that used for Intermediate 17a using the appropriate amines instead of pyridin-2-ylmethanamine.

Preparation of (3S,4R)-tert-butyl 4-(3-((2-(1H-pyrazol-4-yl)ethyl)carbamoyl)-4-fluorophenyl)-3-((benzo[d][1,3]dioxol-5-yloxy)methyl)piperidine-1-carboxylate (17b)

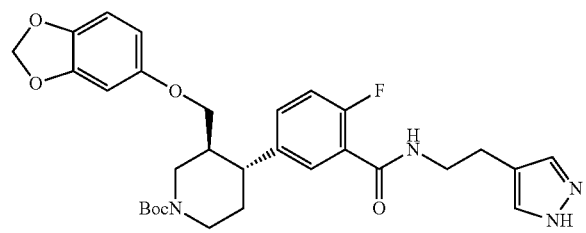 [SMILES: CC(C)(C)OC(=O)N1CC[C@@H](c2ccc(F)c(C(=O)NCCc3cn[nH]c3)c2)[C@H](COc2ccc3c(c2)OCO3)C1]

Prepared as described for Intermediate 17a from Intermediate 16 and 4-(2-aminoethyl)pyrazole. $^1$H NMR (CDCl$_3$, 400 MHz) δ: 7.92, 7.49, 7.02, 6.82-6.75, 6.62, 6.34, 6.13, 5.88, 4.45, 4.24, 3.68, 3.58, 3.44, 2.96-2.70, 2.09, 1.81-1.70, 1.50.

Preparation of (3S,4R)-tert-butyl-3-((benzo[d][1,3]dioxol-5-yloxy)methyl)-4-(4-fluoro-3-((2-methoxybenzyl)carbamoyl)phenyl)piperidine-1-carboxylate (17c)

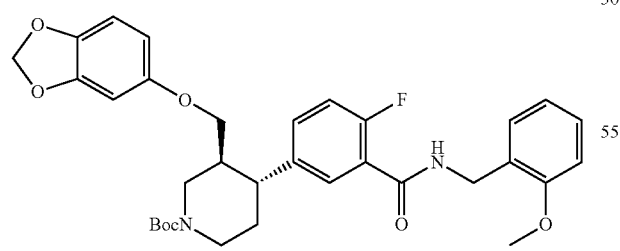

Prepared as described for Intermediate 17a from intermediate 16 and 2-methoxy benzylamine. $^1$H NMR (CDCl$_3$, 400 MHz) δ 8.71 (s, 1H), 8.05-7.82 (m, 1H), 7.43 (dd, J=13.1, 6.0 Hz, 1H), 7.33 (dd, J=7.4, 1.7 Hz, 1H), 7.29-7.13 (m, 2H), 7.00 (t, J=10.0 Hz, 1H), 6.96-6.78 (m, 2H), 6.19 (s, 1H), 5.98-5.75 (m, 2H), 5.58 (dd, J=5.9, 2.0 Hz, 1H), 4.97 (s, 2H), 4.65 (d, J=5.7 Hz, 2H), 3.93-3.78 (m, 3H), 3.74-3.53 (m, 2H), 2.70 (d, J=45.6 Hz, 3H), 1.67-1.53 (m, 1H), 1.36-0.97 (m, 9H).

Preparation of (3S,4R)-tert-butyl-3-((benzo[d][1,3]dioxol-5-yloxy)methyl)-4-(4-fluoro-3-((2-(trifluoromethyl)benzyl)carbamoyl)phenyl)piperidine-1-carboxylate (17d)

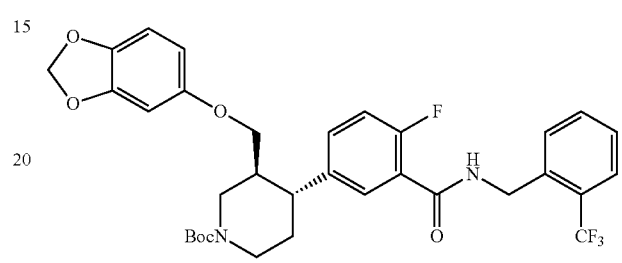

Prepared as described for Intermediate 17a from intermediate 16 and (2-(trifluoromethyl)phenyl)methanamine. $^1$H NMR (CDCl$_3$, 400 MHz) δ 7.91 (m, 1H), 7.65 (t, J=6.2 Hz, 2H), 7.52 (t, J=7.6 Hz, 1H), 7.38 (t, J=7.7 Hz, 1H), 7.25-7.23 (m, 3H), 7.12-6.92 (m, 2H), 6.20 (br s, 1H), 5.87 (m, 2H), 5.09-4.96 (m, 2H), 4.83 (d, J=5.9 Hz, 2H), 4.26 (br s, 1H), 3.64 (m, 2H), 2.71-2.61 (m, 2H), 1.75 (m, 1H), 1.49 (s, 9H).

Preparation of (3S,4R)-tert-butyl-3-((benzo[d][1,3]dioxol-5-yloxy)methyl)-4-(3-((2,6-difluorobenzyl)carbamoyl)-4-fluorophenyl)piperidine-1-carboxylate (17e)

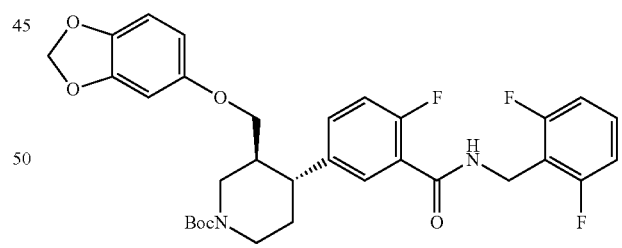

Prepared as described for Intermediate 17a from Intermediate 16 and 2,6-difluorobenzylamine. $^1$H NMR (CDCl$_3$, 400 MHz) δ 7.95 (dd, J=7.5, 2.4 Hz, 1H), 7.35-7.20 (m, 2H), 7.16-7.13 (m, 1H), 7.01 (dd, J=11.8, 8.4 Hz, 1H), 6.94-6.75 (m, 2H), 6.60 (d, J=8.5 Hz, 1H), 6.32 (d, J=2.4 Hz, 1H), 6.11 (dd, J=8.5, 2.5 Hz, 1H), 5.87 (s, 2H), 4.46 (br s, 1H), 4.19 (br s, 1H), 3.56 (dd, J=9.5, 2.8 Hz, 1H), 3.42 (dd, J=9.4, 6.6 Hz, 1H), 2.80-2.69 (m, 3H), 2.07 (m, 2H), 1.74-1.69 (m, 3H), 1.49 (s, 9H).

Preparation of (3S,4R)-tert-butyl-3-((benzo[d][1,3]dioxol-5-yloxy)methyl)-4-(3-((2,6-difluorophenethyl)carbamoyl)-4-fluorophenyl)piperidine-1-carboxylate (17f)

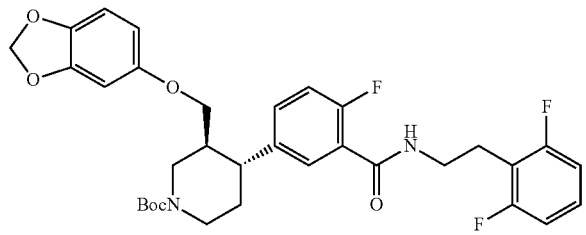 [SMILES: CC(C)(C)OC(=O)N1CC[C@@H](c2ccc(F)c(C(=O)NCCc3c(F)cccc3F)c2)[C@H](COc2ccc3c(c2)OCO3)C1]

Prepared as described for Intermediate 17a from Intermediate 16 and 2-(2,6-difluorophenyl)ethan-1-amine. $^1$H NMR (CDCl$_3$, 400 MHz) δ 7.90 (dd, J=7.5, 2.4 Hz, 1H), 7.24-7.07 (m, 2H), 7.00 (dd, J=11.6, 8.4 Hz, 1H), 6.95-6.65 (m, 4H), 6.60 (d, J=8.5 Hz, 1H), 6.32 (d, J=2.4 Hz, 1H), 6.11 (dd, J=8.5, 2.5 Hz, 1H), 5.86 (s, 2H), 4.41 (br s, 1H), 4.22 (br s, 1H), 3.70 (q, J=6.9 Hz, 1H), 3.56 (m, 1H), 3.49-3.28 (m, 1H), 3.02 (t, J=6.8 Hz, 2H), 2.79-2.68 (m, 2H), 2.10-2.04 (m, 1H), 1.87-1.65 (m, 2H), 1.48 (s, 9H).

Preparation of (3S,4R)-tert-butyl-3-((benzo[d][1,3]dioxol-5-yloxy)methyl)-4-(3-((2,6-dimethylbenzyl)carbamoyl)-4-fluorophenyl)piperidine-1-carboxylate (17g)

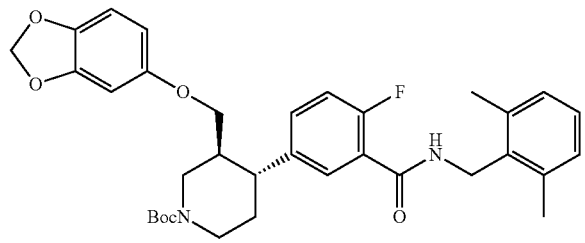 [SMILES: Cc1cccc(C)c1CNC(=O)c1cc([C@@H]2CCN(C(=O)OC(C)(C)C)C[C@H]2COc2ccc3c(c2)OCO3)ccc1F]

Prepared as described for Intermediate 17a from Intermediate 16 and 2,6-dimethylbenzylamine. $^1$H NMR (CD$_3$OD, 400 MHz) δ 7.48, 7.35, 7.13-6.98, 6.59, 6.34, 6.14, 5.83, 4.60, 4.40, 4.18, 3.58, 3.49, 2.77, 2.38, 1.82-1.61, 1.48.

Preparation of (3S,4R)-tert-butyl-3-((benzo[d][1,3]dioxol-5-yloxy)methyl)-4-(3-((2,6-bis(trifluoromethyl)benzyl)carbamoyl)-4-fluorophenyl)piperidine-1-carboxylate (17h)

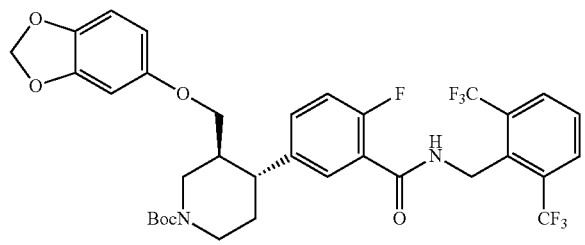 [SMILES: CC(C)(C)OC(=O)N1CC[C@@H](c2ccc(F)c(C(=O)NCc3c(C(F)(F)F)cccc3C(F)(F)F)c2)[C@H](COc2ccc3c(c2)OCO3)C1]

Prepared as described for Intermediate 17a from Intermediate 16 using 2,6-ditrifluoromethylbenzylamine hydrochloride. $^1$H NMR (CD$_3$OD, 400 MHz) δ 8.06, 7.75, 7.46, 7.36, 7.08, 6.59, 6.34, 6.14, 5.84, 4.85, 4.44-4.35, 4.18, 3.58, 3.49, 2.77, 1.77, 1.69, 1.48.

Preparation of (3S,4R)-tert-butyl 3-((benzo[d][1,3]dioxol-5-yloxy)methyl)-4-(3-((2,6-dimethoxybenzyl)carbamoyl)-4-fluorophenyl)piperidine-1-carboxylate (17i)

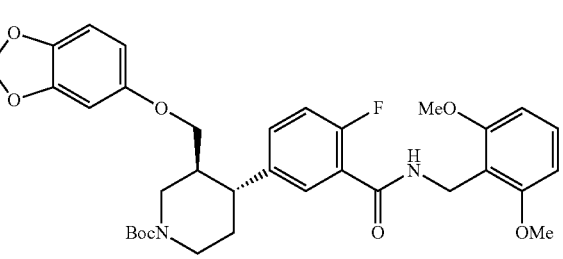

Prepared as described for intermediate 17a from intermediate 16 using 2,6-dimethoxybenzylamine. $^1$H NMR (CD$_3$OD, 400 MHz) δ 7.97, 7.62, 7.35, 7.24, 7.08, 6.64, 6.58, 6.32, 6.13, 5.82, 4.65, 4.40, 4.22-4.13, 3.83, 3.61-3.43, 2.75, 2.10-1.98, 1.81-1.72, 1.66, 1.48.

Preparation of (3S,4R)-tert-butyl 3-((benzo[d][1,3]dioxol-5-yloxy)methyl)-4-(3-((2,6-dichlorobenzyl)carbamoyl)-4-fluorophenyl)piperidine-1-carboxylate (17j)

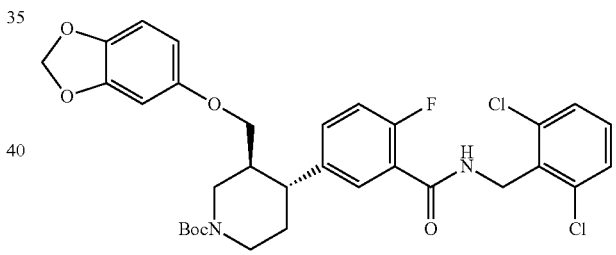

Prepared as described for intermediate 17a from intermediate 16 using 2,6-dichlorobenzylamine. $^1$H NMR (CD$_3$OD, 400 MHz) δ 7.52, 7.45-7.33, 7.29, 7.10, 6.59, 6.34, 6.14, 5.84, 4.86, 4.40, 4.23-4.14, 3.59, 3.49, 3.35, 2.98-2.72, 2.10-1.99, 1.82-1.74, 1.68, 1.49.

Preparation of tert-butyl (3S,4R)-3-((benzo[d][1,3]dioxol-5-yloxy)methyl)-4-(3-(benzylcarbamoyl)-4-fluorophenyl)piperidine-1-carboxylate (17k)

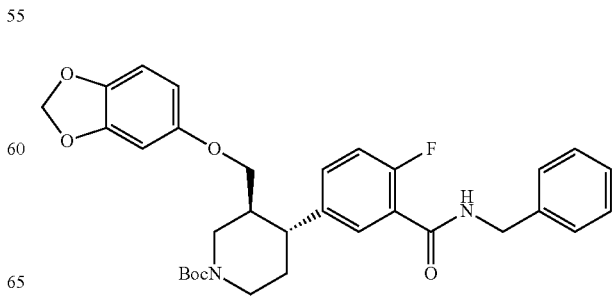

Prepared as described for intermediate 17a from intermediate 16 using benzylamine. ¹H NMR (500 MHz, Chloroform-d) δ 7.97 (dd, J=7.5, 2.5 Hz, 1H), 7.38-7.34 (m, 3H), 7.29 (ddt, J=8.7, 6.4, 3.4 Hz, 2H), 7.03 (ddd, J=14.9, 10.0, 4.2 Hz, 2H), 6.62 (d, J=8.4 Hz, 1H), 6.34 (d, J=2.5 Hz, 1H), 6.13 (dd, J=8.5, 2.5 Hz, 1H), 5.87 (s, 2H), 4.68 (d, J=5.6 Hz, 2H), 4.45 (s, 1H), 4.25 (s, 1H), 3.59 (dd, J=9.4, 2.8 Hz, 1H), 3.45 (dd, J=9.5, 6.5 Hz, 1H), 2.77 (dt, J=23.6, 11.9 Hz, 3H), 2.10 (ddq, J=11.5, 7.7, 4.0 Hz, 1H), 1.80 (d, J=13.2 Hz, 1H), 1.76-1.68 (m, 1H), 1.50 (s, 9H).

Preparation of tert-butyl (3S,4R)-3-((benzo[d][1,3]dioxol-5-yloxy)methyl)-4-(4-fluoro-3-(phenethylcarbamoyl)phenyl)piperidine-1-carboxylate (17l)

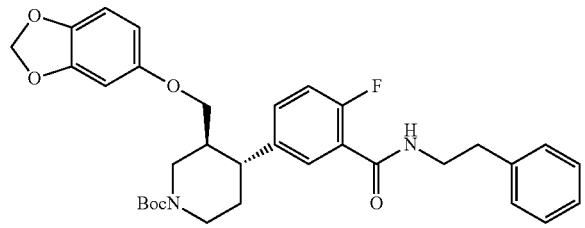 [SMILES: CC(C)(C)OC(=O)N1CC[C@@H](c2ccc(F)c(C(=O)NCCc3ccccc3)c2)[C@H](COc2ccc3c(c2)OCO3)C1]

Prepared as described for intermediate 17a from intermediate 16 using 2-phenylethylamine. ¹H NMR (500 MHz, Chloroform-d) δ 7.93 (dd, J=7.5, 2.4 Hz, 1H), 7.37-7.30 (m, 2H), 7.29-7.23 (m, 4H), 7.01 (dd, J=11.6, 8.4 Hz, 1H), 6.80-6.71 (m, 1H), 6.63 (d, J=8.4 Hz, 1H), 6.35 (d, J=2.5 Hz, 1H), 6.14 (dd, J=8.5, 2.5 Hz, 1H), 5.88 (s, 2H), 4.46 (s, 1H), 4.25 (s, 1H), 3.74 (q, J=5.9 Hz, 2H), 3.59 (dd, J=9.5, 2.9 Hz, 1H), 3.45 (dd, J=9.5, 6.6 Hz, 1H), 2.94 (t, J=7.0 Hz, 2H), 2.87-2.69 (m, 3H), 2.10 (tdt, J=10.4, 7.0, 3.0 Hz, 1H), 1.83-1.67 (m, 2H), 1.51 (s, 9H).

Preparation of tert-butyl (3S,4R)-3-((benzo[d][1,3]dioxol-5-yloxy)methyl)-4-(4-fluoro-3-((pyridin-3-ylmethyl)carbamoyl)phenyl)piperidine-1-carboxylate (17m)

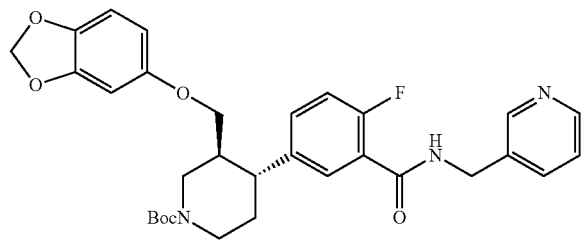 [SMILES: CC(C)(C)OC(=O)N1CC[C@@H](c2ccc(F)c(C(=O)NCc3cccnc3)c2)[C@H](COc2ccc3c(c2)OCO3)C1]

Prepared as described for intermediate 17a from intermediate 16 using 3-picoylamine. ¹H NMR (500 MHz, Chloroform-d) δ 8.62 (d, J=2.3 Hz, 1H), 8.55 (dd, J=4.7, 1.6 Hz, 1H), 7.96 (dd, J=7.5, 2.4 Hz, 1H), 7.71 (d, J=7.7 Hz, 1H), 7.29 (td, J=7.9, 4.9 Hz, 2H), 7.12-7.01 (m, 2H), 6.62 (d, J=8.4 Hz, 1H), 6.34 (d, J=2.4 Hz, 1H), 6.13 (dd, J=8.4, 2.5 Hz, 1H), 5.87 (s, 2H), 4.69 (d, J=5.9 Hz, 2H), 4.44 (s, 1H), 4.24 (s, 1H), 3.59 (dd, J=9.4, 2.8 Hz, 1H), 3.45 (dd, J=9.5, 6.5 Hz, 1H), 2.78 (dt, J=22.3, 13.0 Hz, 3H), 2.14-2.06 (m, 1H), 1.84-1.69 (m, 2H), 1.50 (s, 9H).

Preparation of tert-butyl (3S,4R)-3-((benzo[d][1,3]dioxol-5-yloxy)methyl)-4-(4-fluoro-3-((pyridin-4-ylmethyl)carbamoyl)phenyl)piperidine-1-carboxylate (17n)

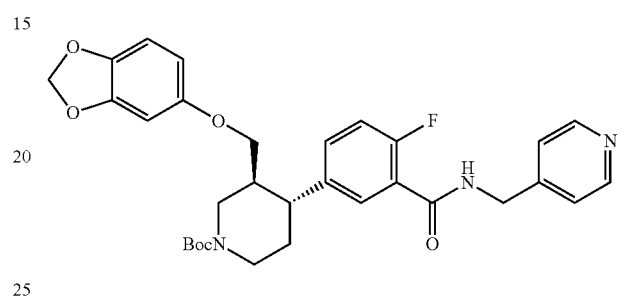

Prepared as described for intermediate 17a from intermediate 16 using 4-(aminomethyl)pyridine. ¹H NMR (500 MHz, Chloroform-d) δ 8.60-8.53 (m, 2H), 7.96 (dd, J=7.5, 2.4 Hz, 1H), 7.32 (ddd, J=7.9, 4.8, 2.4 Hz, 1H), 7.28-7.23 (m, 2H), 7.21 (dt, J=12.7, 6.0 Hz, 1H), 7.07 (dd, J=11.7, 8.5 Hz, 1H), 6.62 (d, J=8.4 Hz, 1H), 6.34 (d, J=2.4 Hz, 1H), 6.13 (dd, J=8.5, 2.5 Hz, 1H), 5.87 (s, 2H), 4.68 (d, J=6.0 Hz, 2H), 4.44 (s, 1H), 4.25 (s, 1H), 3.59 (dd, J=9.5, 2.8 Hz, 1H), 3.45 (dd, J=9.5, 6.4 Hz, 1H), 2.87-2.70 (m, 3H), 2.09 (dtt, J=10.4, 6.9, 3.4 Hz, 1H), 1.85-1.67 (m, 2H), 1.50 (s, 9H).

Preparation of tert-butyl (3S,4R)-3-((benzo[d][1,3]dioxol-5-yloxy)methyl)-4-(4-fluoro-3-((2-(pyridin-2-yl)ethyl)carbamoyl)phenyl)piperidine-1-carboxylate (17o)

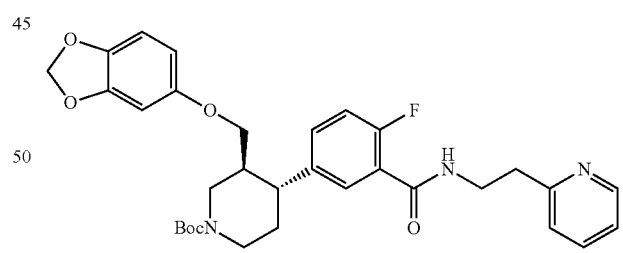

Prepared as described for intermediate 17a from intermediate 16 using 2-(2-aminoethyl)pyridine. ¹H NMR (500 MHz, Chloroform-d) δ 8.56 (dt, J=5.1, 1.2 Hz, 1H), 7.91 (dd, J=7.4, 2.4 Hz, 1H), 7.70-7.63 (m, 1H), 7.62 (td, J=7.6, 1.8 Hz, 1H), 7.25-7.22 (m, 1H), 7.19 (d, J=7.8 Hz, 1H), 7.16 (ddd, J=7.7, 4.9, 1.1 Hz, 1H), 7.00 (dd, J=11.5, 8.4 Hz, 1H), 6.61 (d, J=8.5 Hz, 1H), 6.33 (d, J=2.4 Hz, 1H), 6.12 (dd, J=8.5, 2.5 Hz, 1H), 5.87 (s, 2H), 4.44 (s, 1H), 4.24 (s, 1H), 3.90 (q, J=5.9 Hz, 2H), 3.58 (dd, J=9.5, 2.9 Hz, 1H), 3.44 (dd, J=9.4, 6.7 Hz, 1H), 3.10 (t, J=6.4 Hz, 2H), 2.82-2.68 (m, 3H), 2.09 (dtd, J=11.0, 7.5, 3.4 Hz, 1H), 1.80-1.66 (m, 2H), 1.50 (s, 9H).

Preparation of tert-butyl (3S,4R)-3-((benzo[d][1,3]dioxol-5-yloxy)methyl)-4-(4-fluoro-3-((2-(pyridin-4-yl)ethyl)carbamoyl)phenyl)piperidine-1-carboxylate (17p)

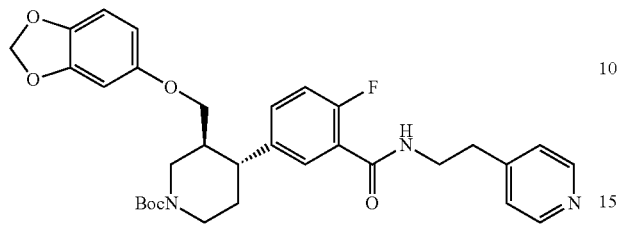

Prepared as described for intermediate 17a from intermediate 16 using 4-(2-aminoethyl)pyridine. $^1$H NMR (500 MHz, Chloroform-d) δ 8.56-8.52 (m, 2H), 7.92 (dd, J=7.5, 2.4 Hz, 1H), 7.31-7.25 (m, 4H), 7.18-7.15 (m, 2H), 7.02 (dd, J=11.7, 8.5 Hz, 1H), 6.76 (dt, J=12.4, 5.8 Hz, 1H), 6.62 (d, J=8.5 Hz, 1H), 6.34 (d, J=2.5 Hz, 1H), 6.13 (dd, J=8.5, 2.5 Hz, 1H), 5.87 (s, 2H), 4.44 (s, 1H), 4.24 (s, 1H), 3.75 (q, J=6.8 Hz, 2H), 3.58 (dd, J=9.5, 2.9 Hz, 1H), 3.49 (d, J=4.9 Hz, 1H), 3.44 (dd, J=9.5, 6.5 Hz, 1H), 2.95 (t, J=7.0 Hz, 2H), 2.86-2.69 (m, 3H), 2.08 (dtd, J=13.1, 6.8, 5.9, 3.2 Hz, 1H), 1.79 (d, J=13.7 Hz, 1H), 1.76-1.66 (m, 1H), 1.50 (s, 9H).

Preparation of tert-butyl (3S,4R)-3-((benzo[d][1,3]dioxol-5-yloxy)methyl)-4-(4-fluoro-3-((2-(pyridin-3-yl)ethyl)carbamoyl)phenyl)piperidine-1-carboxylate (17a)

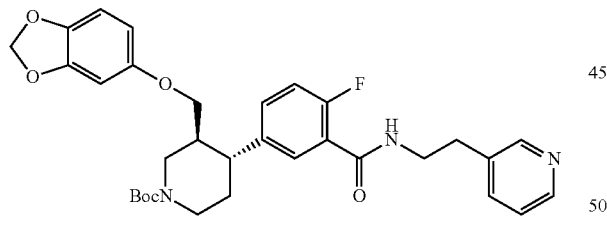

Prepared as described for intermediate 17a from intermediate 16 using 3-(2-aminoethyl)pyridine. $^1$H NMR (500 MHz, Chloroform-d) δ 8.52-8.48 (m, 2H), 7.92 (dd, J=7.5, 2.4 Hz, 1H), 7.58 (dt, J=7.8, 2.0 Hz, 1H), 7.30-7.27 (m, 1H), 7.02 (dd, J=11.7, 8.4 Hz, 1H), 6.76 (dt, J=12.4, 5.8 Hz, 1H), 6.62 (d, J=8.5 Hz, 1H), 6.34 (d, J=2.4 Hz, 1H), 6.13 (dd, J=8.5, 2.5 Hz, 1H), 5.87 (s, 2H), 4.44 (s, 1H), 4.24 (s, 1H), 3.73 (q, J=6.8 Hz, 2H), 3.58 (dd, J=9.5, 2.9 Hz, 1H), 3.44 (dd, J=9.5, 6.5 Hz, 1H), 2.95 (t, J=7.1 Hz, 2H), 2.88-2.69 (m, 3H), 2.09 (dtt, J=10.8, 7.3, 3.5 Hz, 1H), 1.83-1.67 (m, 2H), 1.50 (s, 9H).

Preparation of tert-butyl (3S,4R)-4-(3-(((1H-pyrazol-5-yl)methyl)carbamoyl)-4-fluorophenyl)-3-((benzo[d][1,3]dioxol-5-yloxy)methyl)piperidine-1-carboxylate (17r)

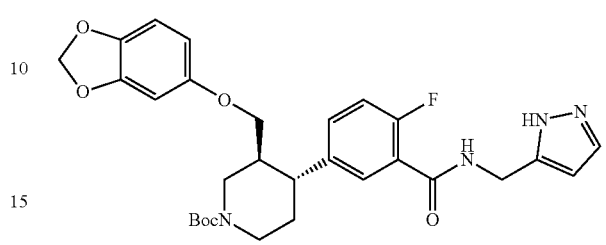

Prepared as described for intermediate 17a from intermediate 16 using 2H-pyrazol-3-ylmethylamine hydrochloride. $^1$H NMR (400 MHz, Chloroform-d) δ 10.71 (bs, 1H) 7.95 (dd, J=7.5, 2.4 Hz, 1H), 7.52 (d, J=2.1 Hz, 1H), 7.37 (dt, J=11.8, 5.5 Hz, 1H), 7.28 (d, J=5.7 Hz, 1H), 7.03 (dd, J=11.6, 8.4 Hz, 1H), 6.61 (d, J=8.5 Hz, 1H), 6.34 (d, J=2.5 Hz, 1H), 6.28 (d, J=2.1 Hz, 1H), 6.12 (dd, J=8.5, 2.5 Hz, 1H), 5.87 (q, J=1.4 Hz, 2H), 4.73-4.65 (m, 2H), 4.45 (s, 1H), 4.25 (s, 1H), 3.58 (dd, J=9.5, 2.8 Hz, 1H), 3.43 (dd, J=9.5, 6.5 Hz, 1H), 2.85-2.68 (m, 3H), 2.09 (td, J=7.7, 7.0, 3.8 Hz, 1H), 1.73 (dq, J=18.5, 14.0 Hz, 2H), 1.50 (s, 9H).

Preparation of tert-butyl (3S,4R)-4-(3-(((1H-imidazol-2-yl)methyl)carbamoyl)-4-fluorophenyl)-3-((benzo[d][1,3]dioxol-5-yloxy)methyl)piperidine-1-carboxylate (17s)

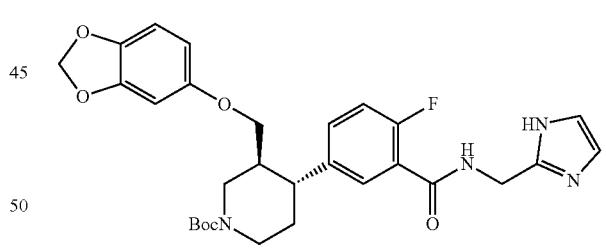

Prepared as described for intermediate 17a from intermediate 16 using 1H-imidazole-2-methanamine dihydrochloride. $^1$H NMR (400 MHz, Chloroform-d) δ 7.93 (dd, J=7.4, 2.4 Hz, 1H), 7.64 (dd, J=12.7, 6.1 Hz, 1H), 7.30 (ddd, J=7.9, 4.8, 2.4 Hz, 1H), 7.05 (dd, J=11.7, 8.5 Hz, 1H), 6.98 (s, 2H), 6.61 (d, J=8.4 Hz, 1H), 6.34 (d, J=2.5 Hz, 1H), 6.12 (dd, J=8.5, 2.5 Hz, 1H), 5.88 (d, J=1.2 Hz, 2H), 4.66 (d, J=5.8 Hz, 2H), 4.45 (s, 1H), 4.25 (s, 1H), 3.59 (dd, J=9.6, 2.8 Hz, 1H), 3.43 (dd, J=9.5, 6.3 Hz, 1H), 2.88-2.71 (m, 3H), 2.15-2.00 (m, 1H), 1.87-1.60 (m, 2H), 1.50 (s, 9H).

Preparation of tert-butyl (3S,4R)-4-(3-((2-(1H-imidazol-4-yl)ethyl)carbamoyl)-4-fluorophenyl)-3-((benzo[d][1,3]dioxol-5-yloxy)methyl)piperidine-1-carboxylate (17t)

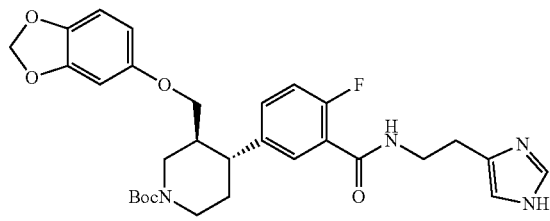 [SMILES: CC(C)(C)OC(=O)N1CC[C@@H](c2ccc(F)c(C(=O)NCCc3c[nH]cn3)c2)[C@H](COc2ccc3c(c2)OCO3)C1]

Prepared as described for intermediate 17a from intermediate 16 using histamine. $^1$H NMR (400 MHz, Chloroform-d) δ 7.87 (dd, J=7.4, 2.4 Hz, 1H), 7.59 (s, 1H), 7.35-7.28 (m, 1H), 7.24 (dq, J=7.2, 2.4 Hz, 1H), 7.01 (dd, J=11.4, 8.5 Hz, 1H), 6.85 (s, 1H), 6.61 (d, J=8.4 Hz, 1H), 6.33 (d, J=2.4 Hz, 1H), 6.12 (dd, J=8.5, 2.5 Hz, 1H), 5.87 (s, 2H), 4.44 (s, 1H), 4.24 (s, 1H), 3.76 (q, J=6.3 Hz, 2H), 3.57 (dd, J=9.5, 2.8 Hz, 1H), 3.43 (dd, J=9.5, 6.6 Hz, 1H), 2.92 (t, J=6.5 Hz, 2H), 2.88-2.66 (m, 3H), 2.14-2.03 (m, 1H), 1.82-1.64 (m, 2H), 1.50 (s, 9H). Example 7: 5-((3S,4R)-3-((benzo[d][1,3]dioxol-5-yloxy)methyl)piperidin-4-yl)-2-fluoro-N-(pyridin-2-ylmethyl)benzamide hydrochloride (CCG211998) (E07)

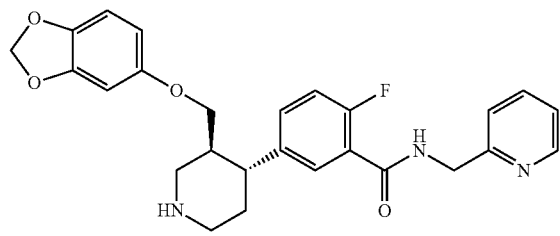

(3S,4R)-tert-butyl 3-((benzo[d][1,3]dioxol-5-yloxy)methyl)-4-(4-fluoro-3-((pyridin-2-ylmethyl)carbamoyl)phenyl)piperidine-1-carboxylate (0.088 g, 0.155 mmol) was added to dioxane (0.5 mL) followed by 4M HCl/dioxane (0.186 mL) and stirred at room temperature for one hour. The reaction was concentrated in vacuo, then diethyl ether was added to precipitate a white solid which was then further purified using 5% methanolic ammonia (7M) in ethyl acetate to give 5-((3S,4R)-3-((benzo[d][1,3]dioxol-5-yloxy)methyl)piperidin-4-yl)-2-fluoro-N-(pyridin-2-ylmethyl)benzamide hydrochloride as a white solid (0.026 g, 0.052 mmol, 34% yield). $^1$H NMR (CD$_3$OD, 400 MHz) δ: 8.49, 7.81, 7.68, 7.47-7.42, 7.31, 7.17, 6.59, 6.34, 6.14, 5.83, 4.69, 3.58, 3.50, 3.35, 3.16-3.10, 2.82-2.64, 2.17-2.07, 1.84-1.71.

The following Examples 8-16 were prepared from Intermediates 17b-j in a manner analogous to that described for Example 7.

Example 8: N-(2-(1H-pyrazol-4-yl)ethyl)-5-((3S,4R)-3-((benzo[d][1,3]dioxol-5-yloxy)methyl)piperidin-4-yl)-2-fluorobenzamide hydrochloride (CCG 224060) (E08)

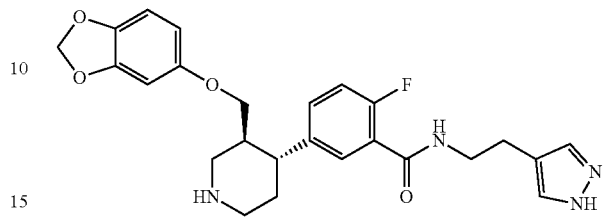

Prepared from Intermediate 17b as described for Example 7. $^1$H NMR (CD$_3$OD, 500 MHz) δ: 7.54, 7.50, 7.39, 7.12, 6.60, 6.34, 6.14, 5.83, 3.60-3.53, 3.50-3.47, 3.37, 3.19-3.15, 2.82-2.70, 2.15-2.10, 1.84-1.76.

Example 9: 5-((3S,4R)-3-((benzo[d][1,3]dioxol-5-yloxy)methyl)piperidin-4-yl)-2-fluoro-N-(2-methoxybenzyl)benzamide hydrochloride (CCG 211993) (E09)

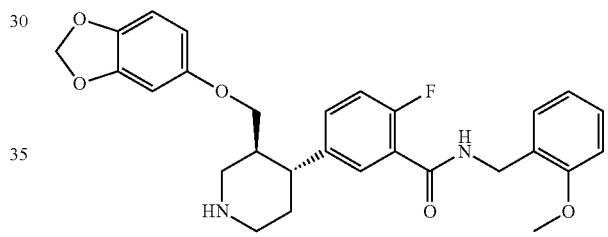

Prepared from intermediate 17c as described for Example 7. $^1$H NMR (CDCl$_3$, 400 MHz) δ 7.97 (m, 1H), 7.44 (m, 1H), 7.38-7.22 (m, 4H), 7.04 (m, 2H), 6.98-6.79 (m, 2H), 6.20 (s, 1H), 5.87 (s, 2H), 4.67 (d, J=5.9 Hz, 2H), 3.89 (s, 3H), 3.57 (m, 1H), 3.48-3.39 (m, 3H), 3.19 (m, 1H), 2.72-2.57 (m, 1H), 2.17 (m, 1H), 1.78-1.76 (s, 1H), 1.45-1.15 (m, 3H).

Example 10: 5-((3S,4R)-3-((benzo[d][1,3]dioxol-5-yloxy)methyl)piperidin-4-yl)-2-fluoro-N-(2-(trifluoromethyl)benzyl)benzamide hydrochloride (CCG211991) (E10)

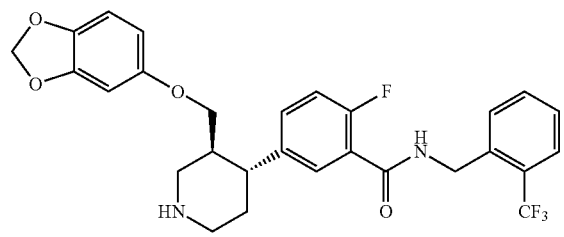 [SMILES: O=C(NCc1ccccc1C(F)(F)F)c1cc([C@@H]2CCNC[C@H]2COc2ccc3c(c2)OCO3)ccc1F]

Prepared from intermediate 17d as described for Example 7. $^1$H NMR (CD$_3$OD, 400 MHz) δ 8.75 (s, 2H), 7.81-7.01 (m, 9H), 6.94 (d, J=11.2 Hz, 2H), 6.37 (s, 2H), 5.91 (d, J=35.8 Hz, 2H), 4.77 (s, 3H), 4.06-3.33 (m, 5H), 2.88 (s, 3H), 2.05 (s, 2H), 1.78 (s, 2H), 1.41-0.82 (m, 9H), 5.01-4.91 (m, 1H).

Example 11: 5-((3S,4R)-3-((benzo[d][1,3]dioxol-5-yloxy)methyl)piperidin-4-yl)-N-(2,6-difluorobenzyl)-2-fluorobenzamide hydrochloride (CCG208947) (E11)

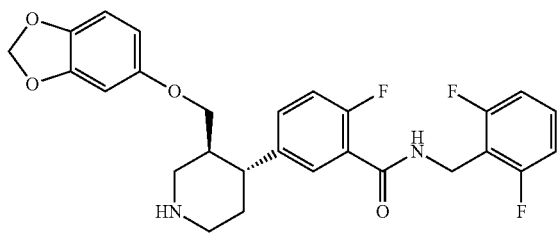 [SMILES: O=C(NCc1c(F)cccc1F)c1cc([C@@H]2CCNC[C@H]2COc2ccc3c(c2)OCO3)ccc1F]

Prepared from Intermediate 17e as described for Example 7. $^1$H NMR (CDCl$_3$, 400 MHz) δ 7.98 (dd, J=7.6, 2.4 Hz, 1H), 7.26 (s, 5H), 7.14 (s, 1H), 7.02 (dd, J=11.8, 8.4 Hz, 1H), 6.91 (t, J=7.8 Hz, 2H), 6.60 (d, J=8.4 Hz, 1H), 6.10 (dd, J=8.5, 2.5 Hz, 1H), 5.86 (s, 2H), 4.77 (d, J=5.7 Hz, 2H), 3.53-3.40 (m, 3H), 3.19-3.16 (m, 1H), 2.70-2.63 (m, 2H), 2.12 (s, 1H), 1.77-1.67 (m, 3H).

Example 12: 5-((3S,4R)-3-((benzo[d][1,3]dioxol-5-yloxy)methyl)piperidin-4-yl)-N-(2,6-difluorobenzyl)-2-fluorobenzamide (CCG2211990) (E12)

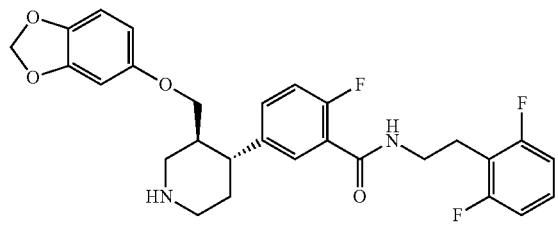 [SMILES: O=C(NCCc1c(F)cccc1F)c1cc([C@@H]2CCNC[C@H]2COc2ccc3c(c2)OCO3)ccc1F]

Prepared as from Intermediate 17f as described for Example 7. $^1$H NMR (CDCl$_3$, 400 MHz) δ 7.98 (dd, J=7.6, 2.4 Hz, 1H), 7.26 (s, 5H), 7.14 (s, 1H), 7.02 (dd, J=11.8, 8.4 Hz, 1H), 6.91 (t, J=7.8 Hz, 2H), 6.60 (d, J=8.4 Hz, 1H), 6.10 (dd, J=8.5, 2.5 Hz, 1H), 5.86 (s, 2H), 4.77 (d, J=5.7 Hz, 2H), 3.53-3.40 (m, 3H), 3.19-3.16 (m, 1H), 2.70-2.63 (m, 2H), 2.12 (s, 1H), 1.77-1.67 (m, 3H).

Example 13: 5-((3S,4R)-3-((benzo[d][1,3]dioxol-5-yloxy)methyl)piperidin-4-yl)-N-(2,6-dimethylbenzyl)-2-fluorobenzamide hydrochloride (CCG232403) (E13)

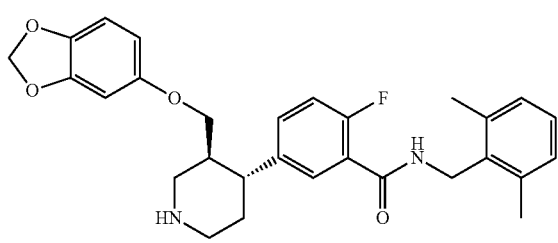 [SMILES: Cc1cccc(C)c1CNC(=O)c1cc([C@@H]2CCNC[C@H]2COc2ccc3c(c2)OCO3)ccc1F]

Prepared from Intermediate 17g as described for Example 7. $^1$H NMR (CD$_3$OD, 500 MHz) δ: 7.54, 7.41, 7.13, 7.11-6.99, 6.60, 6.38, 6.16, 5.86-5.81, 4.59, 3.73-3.60, 3.59-3.48, 3.16, 3.03, 2.51-2.40, 2.38, 2.07-2.00.

Example 14: 5-((3S,4R)-3-((benzo[d][1,3]dioxol-5-yloxy)methyl)piperidin-4-yl)-N-(2,6-bis(trifluoromethyl)benzyl)-2-fluorobenzamide hydrochloride (CCG232404) (E14)

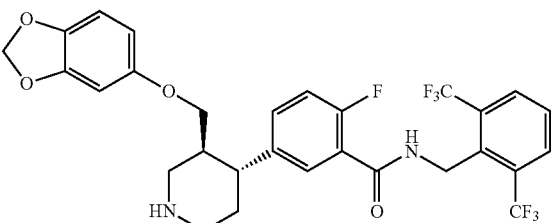

Prepared from Intermediate 17h as described for Example 7. $^1$H NMR (CD$_3$OD, 500 MHz) δ: 8.07, 7.76, 7.53, 7.44-7.39, 7.14, 6.60, 6.38, 6.17, 5.85, 4.86, 3.71-3.63, 3.58-3.50, 3.17, 3.10-2.99, 2.46, 2.11-2.01.

Example 15: 5-((3S,4R)-3-((benzo[d][1,3]dioxol-5-yloxy)methyl)piperidin-4-yl)-N-(2,6-dimethoxybenzyl)-2-fluorobenzamide hydrochloride (CCG232402) (E15)

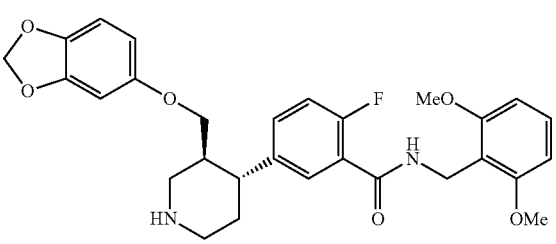 [SMILES: COc1cccc(OC)c1CNC(=O)c1cc([C@@H]2CCNC[C@H]2COc2ccc3c(c2)OCO3)ccc1F]

Prepared from Intermediate 17i as described for Example 7. $^1$H NMR (CD$_3$OD, 500 MHz) δ: 7.67, 7.41, 7.25, 7.15, 6.65, 6.60, 6.37, 6.17, 5.84, 4.85, 4.66, 3.84, 3.71-3.63, 3.60-3.49, 3.16, 3.02, 2.44, 2.09-1.97.

Example 16: 5-((3S,4R)-3-((benzo[d][1,3]dioxol-5-yloxy)methyl)piperidin-4-yl)-N-(2,6-dichlorobenzyl)-2-fluorobenzamide hydrochloride (CCG232407) (E16)

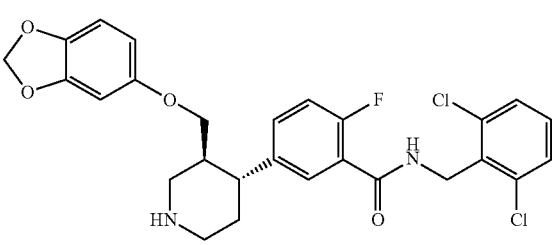 [SMILES: O=C(NCc1c(Cl)cccc1Cl)c1cc([C@@H]2CCNC[C@H]2COc2ccc3c(c2)OCO3)ccc1F]

Prepared from Intermediate 17j as described for Example 7. ¹H NMR (CD$_3$OD, 500 MHz) δ 7.57, 7.41, 7.30, 7.15, 6.61, 6.39, 6.17, 5.88-5.83, 4.87, 3.70-3.63, 3.61-3.44, 3.16, 3.03, 2.41, 2.10-1.96.

Synthetic Scheme 3

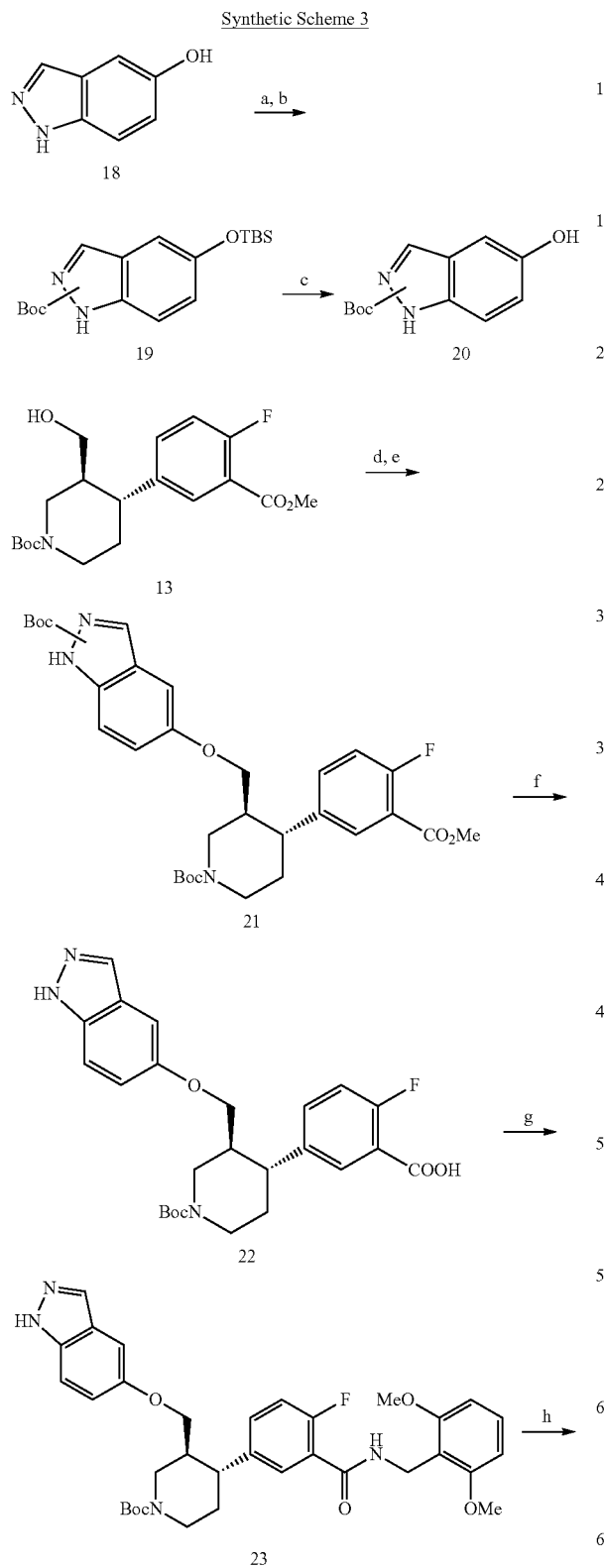

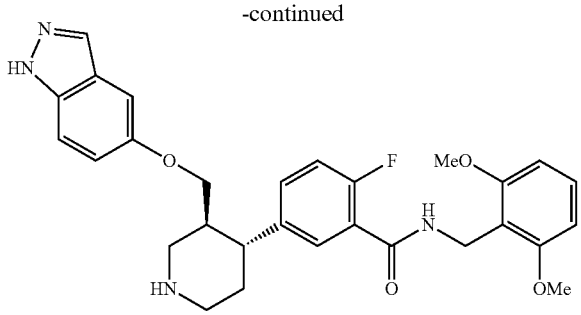

a) TBSCl, ImH, DIEA, DCM, b) Boc$_2$O, DMAP, DIEA, THF, c) TBAF, THF, d) Ms$_2$O, DIEA, DCM, 0° C., e) NaH, 20, DMF, 65° C., 10 min, f) NaOH, H$_2$O, THF, g) HATU, DIEA, 2,6-dimethoxybenzylamine, THF, h) 4M HCl/dioxanes Preparation of 5-((tert-butyldimethylsilyl)oxy)-1H-indazole (18)

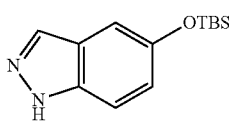 [SMILES: CC(C)(C)[Si](C)(C)Oc1ccc2[nH]ncc2c1]

1H-indazol-5-ol (1.00 g, 7.45 mmol) dissolved in 20 mL of anhydrous methylene chloride was added to a 100 mL round bottom flask. Tert-butyldimethylsilyl chloride (1.69 g, 11.18 mmol) and imidazole (0.51 g, 7.45 mmol) were added to the reaction vessel producing a cloudy white mixture. Lastly, N,N-diisopropylethylamine (1.95 mL, 11.18 mmol) was added, giving a clear solution. The reaction was stirred overnight at room temperature. Methylene chloride was used to dilute the reaction followed by washing with NaCl (2×). The organic layer was dried over MgSO$_4$, concentrated in vacuo, and purified using flash chromatography with a 20% EtOAc/Hexane gradient to give 5-((tert-butyldimethylsilyl)oxy)-1H-indazole (1.72 g, 93%). ¹H NMR (DMSO-d$_6$, 400 MHz) δ: 12.91 (s, 1H), 7.92 (s, 1H), 7.41 (d, J=9.0 Hz, 1H), 7.12 (d, J=1.5 Hz, 1H), 6.91 (dd, J=8.8, 2.3 Hz, 1H), 0.96 (s, 9H), 0.18 (s, 6H).

Preparation of tert-butyl 5-((tert-butyldimethylsilyl)oxy)-1H-indazole-1-carboxylate/tert-butyl 5-((tert-butyldimethylsilyl)oxy)-2H-indazole-2-carboxylate (19)

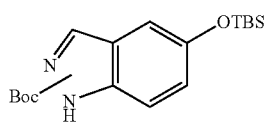

5-((tert-butyldimethylsilyl)oxy)-1H-indazole (1.00 g, 4.85 mmol) was dissolved in 20 mL of anhydrous tetrahydrofuran and added to a 100 mL round bottom flask. Di-tert-butyl dicarbonate (1.67 mL, 7.27 mmol), dimethylaminopyridine (0.06 g, 0.48 mmol), and diisopropylethylamine (1.44 mL, 8.24 mmol) were added to the reaction vessel and stirred overnight. Ethyl acetate and water were used to dilute the reaction followed by washing with NaCl (2×). The organic layer was dried over MgSO$_4$, concentrated in vacuo, and purified to give the regioisomers of tert-butyl 5-((tert-butyldimethylsilyl)oxy)-1H-indazole-1-carboxylate and tert-butyl 5-((tert-butyldimethylsilyl)oxy)-2H-indazole-2-carboxylate (1.07 g, 63%). ¹H NMR (DMSO-d₆, 400 MHz) δ: 8.67 (d, J=1.1 Hz, 1H), 8.28 (d, J=0.9 Hz, 1H), 7.95 (d, J=8.0 Hz, 1H), 7.61 (dt, J=8.9 Hz, 1.2 Hz, 1H), 7.28 (dd, J=2.4 Hz, 0.7 Hz, 1H), 7.15 (dd, J=8.9 Hz, 2.4 Hz, 1H), 7.03-6.94 (m, 2H), 1.63 (d, J=3.5 Hz, 18H), 0.96 (d, J=2.0 Hz, 18H), 0.21 (d, J=3.5 Hz, 12H).

Preparation of tert-butyl 5-hydroxy-1H-indazole-1-carboxylate/tert-butyl 5-hydroxy-2H-indazole-2-carboxylate (20)

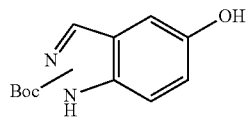

Tert-butyl 5-((tert-butyldimethylsilyl)oxy)-1H-indazole-1-carboxylate/tert-butyl 5-((tert-butyldimethylsilyl)oxy)-2H-indazole-2-carboxylate (1.69 g, 4.85 mmol) and tetra n-butylammonium fluoride (2.34 g, 9.70 mmol) was added to 20 mL of anhydrous tetrahydrofuran in a 100 mL round bottom flask at 0° C. and stirred for 2.5 hours. Ethyl acetate and water were used to dilute the reaction followed by washing with NaCl (2×). The organic layer was dried over MgSO₄, concentrated in vacuo, and purified using flash chromatography (0-10% EtOAc/Hexanes) to give the regioisomers tert-butyl 5-((tert-butyldimethylsilyl)oxy)-1H-indazole-1-carboxylate/tert-butyl 5-((tert-butyldimethylsilyl)oxy)-2H-indazole-2-carboxylate (0.4769 g, 42%). ¹H NMR (DMSO-d₆, 400 MHz) δ: 9.60 (s, 1H), 8.55 (d, J=1.1 Hz, 1H), 8.21 (d, J=0.8 Hz, 1H), 7.87 (dt, J=8.8 Hz, 0.9 Hz, 1H), 7.53 (dt, J=9.4 Hz, 1.0 Hz, 1H), 7.12-7.03 (m, 2H), 6.97 (dd, J=9.4 Hz, 2.3 Hz, 1H), 6.77 (dd, J=2.3 Hz, 0.9 Hz, 1H), 1.61 (d, J=2.8 Hz, 18H).

Preparation of tert-butyl (3S,4R)-3-(((1H-indazol-5-yl)oxy)methyl)-4-(4-fluoro-3-(methoxycarbonyl)phenyl)piperidine-1-carboxylate (21)

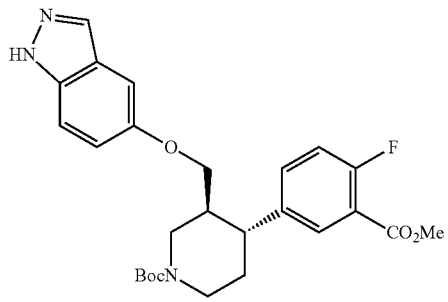 [SMILES: COC(=O)c1cc([C@@H]2CCN(C(=O)OC(C)(C)C)C[C@H]2COc2ccc3[nH]ncc3c2)ccc1F]

To a 0° C. solution of intermediate 20 (0.345 g, 1.474 mmol) in 4 mL DMF was added 60% sodium hydride in mineral oil (0.062 g, 1.54 mmol). The solution stirred for five minutes. To the reaction was added (3S,4R)-tert-butyl 4-(4-fluoro-3-(methoxycarbonyl)phenyl)-3-(((methylsulfonyl)oxy)methyl)piperidine-1-carboxylate (0.313 g, 0.702 mmol) in 4 mL DMF. The reaction was heated to 70° C. for 10 minutes then cooled to room temperature and treated with sat. NH₄Cl solution. Extracted with ethyl acetate/ether (2×), washed with brine, dried with MgSO₄, and concentrated in vacuo. Purified by flash chromatography using a gradient of 10% MeOH/DCM to give as a clear oil tert-butyl (3S,4R)-3-(((1H-indazol-5-yl)oxy)methyl)-4-(4-fluoro-3-(methoxycarbonyl)phenyl)piperidine-1-carboxylate (0.135 g, 0.279 mmol, 40% yield over two steps). ¹H NMR (DMSO, 400 MHz) δ: 8.21, 7.91, 7.72, 7.27, 7.10, 4.35, 4.05, 3.79, 3.70-3.62, 2.80, 2.14, 1.73, 1.62, 1.42.

Preparation of 5-((3S,4R)-3-(((1H-indazol-5-yl)oxy)methyl)-1-(tert-butoxycarbonyl)piperidin-4-yl)-2-fluorobenzoic acid (22)

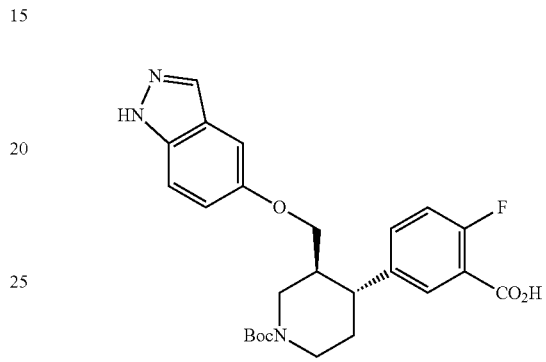

To a round bottom flask equipped with a stir bar was added tert-butyl 6-(((3S,4R)-1-(tert-butoxycarbonyl)-4-(4-fluoro-3-(methoxycarbonyl)phenyl) piperidin-3-yl)methoxy)-1H-indazole-1-carboxylate (0.270 g, 0.463 mmol), 1M NaOH (1.39 mL, 1.388 mmol), H₂O (10 mL), tetrahydrofuran (4 mL) and methanol (6 mL). The reaction was stirred overnight at room temperature. Ether was added to the reaction and the resulting layers were separated. To the aqueous layer 10% citric acid was added to give a pH of 4. The aqueous layer was then extracted 2× with ethyl acetate. The ethyl acetate layers were then combined and washed 1× with NaCl, dried with MgSO₄, and concentrated to give as an amorphous white solid 5-((3S,4R)-3-(((1H-indazol-5-yl)oxy)methyl)-1-(tert-butoxycarbonyl)piperidin-4-yl)-2-fluorobenzoic acid (0.201 g, 0.428 mmol, 92% yield). ¹H NMR (DMSO, 400 MHz) δ: 13.03, 7.86, 7.74, 7.59-7.53, 7.39, 7.23, 6.94-6.86, 4.37, 4.08, 3.61, 2.77, 2.20-2.04, 1.74, 1.69-1.53, 1.42.

Preparation of tert-butyl (3S,4R)-3-(((1H-indazol-5-yl)oxy)methyl)-4-(3-((2,6-dimethoxybenzyl)carbamoyl)-4-fluorophenyl)piperidine-1-carboxylate (23a)

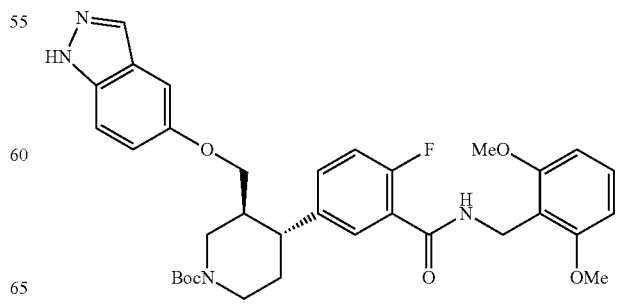

To a round bottom flask equipped with a stir bar was added 5-((3S,4R)-3-(((1H-indazol-6-yl)oxy)methyl)-1-(tert-butoxycarbonyl)piperidin-4-yl)-2-fluorobenzoic acid (0.090 g, 0.190 mmol), HATU (0.146 g, 0.383 mmol), diisopropylbenzylamine (0.067 mL, 0.383 mmol), 2,6-dimethoxybenzylamine (0.064 g, 0.383 mmol), and 2 mL THF. The reaction was stirred overnight at room temperature. The reaction was diluted with ethyl acetate and water and the layers were separated. The organic layer was washed 1× with saturated sodium bicarbonate, washed 2× with brine, dried with MgSO$_4$, and concentrated to give a yellow oil. The oil was then purified using flash chromatography (50-60% EtOAc/Hexanes) to give as an amorphous white solid (0.068 g, 0.111 mmol, 58% yield). $^1$H NMR (DMSO, 400 MHz) δ: 12.87, 7.99, 7.86, 7.52, 7.43-7.38, 7.25, 7.17, 6.91-6.89, 6.67, 4.48, 4.37, 4.07, 3.78, 3.61-3.57, 2.86-2.66, 2.17-2.09, 1.72, 1.59, 1.42.

Preparation of tert-butyl 6-(((3S,4R)-1-(tert-butoxycarbonyl)-4-(4-fluoro-3-((pyridin-2-ylmethyl)carbamoyl)phenyl)piperidin-3-yl)methoxy)-1H-indazole-1-carboxylate (23b)

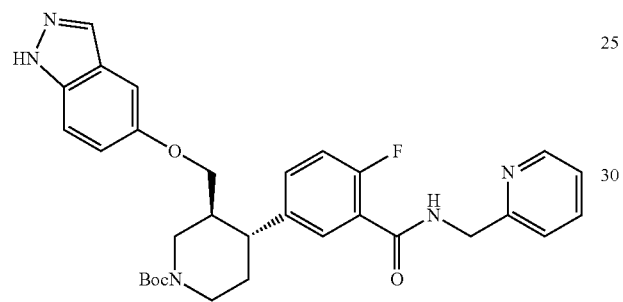

Intermediate 23b was prepared as described previously for intermediate 23a replacing 2,6-dimethoxybenzylamine with 2-picoylamine. $^1$H NMR (400 MHz, Methanol-d$_4$) δ 8.47 (ddd, J=5.0, 1.8, 0.9 Hz, 1H), 7.84 (s, 1H), 7.76 (td, J=7.7, 1.8 Hz, 1H), 7.71 (dd, J=7.0, 2.3 Hz, 1H), 7.46 (ddd, J=8.4, 4.8, 2.3 Hz, 1H), 7.43-7.35 (m, 2H), 7.29 (ddd, J=7.6, 5.0, 1.1 Hz, 1H), 7.17 (dd, J=10.8, 8.5 Hz, 1H), 6.99 (dd, J=9.2, 2.2 Hz, 1H), 6.92 (d, J=2.3 Hz, 1H), 4.66 (s, 2H), 4.48 (d, J=13.0 Hz, 1H), 4.22 (d, J=13.5 Hz, 1H), 3.73 (dd, J=9.8, 3.0 Hz, 1H), 3.63 (dd, J=9.8, 6.9 Hz, 1H), 2.97-2.83 (m, 3H), 2.16 (dq, J=7.4, 3.8 Hz, 1H), 1.83 (d, J=13.2 Hz, 1H), 1.74 (dd, J=12.6, 4.3 Hz, 1H), 1.49 (s, 9H).

Example 17: 5-((3S,4R)-3-(((1H-indazol-6-yl)oxy)methyl)piperidin-4-yl)-N-(2,6-dimethoxybenzyl)-2-fluorobenzamide hydrochloride (CCG232406) (E17)

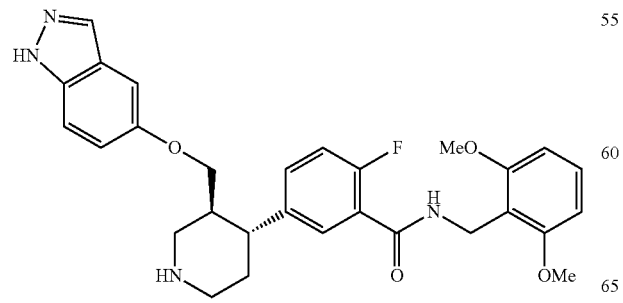

Prepared from Intermediate 23 as described for Example 7. $^1$H NMR (CD$_3$OD, 500 MHz) δ: 7.97, 7.73, 7.46-7.40, 7.25, 7.15, 7.07, 6.98, 6.65, 4.71-4.60, 3.83, 3.80, 3.76-3.65, 3.57-3.51, 3.25-3.15, 3.09, 2.54-2.45, 2.13-1.97.

Synthetic Scheme 4

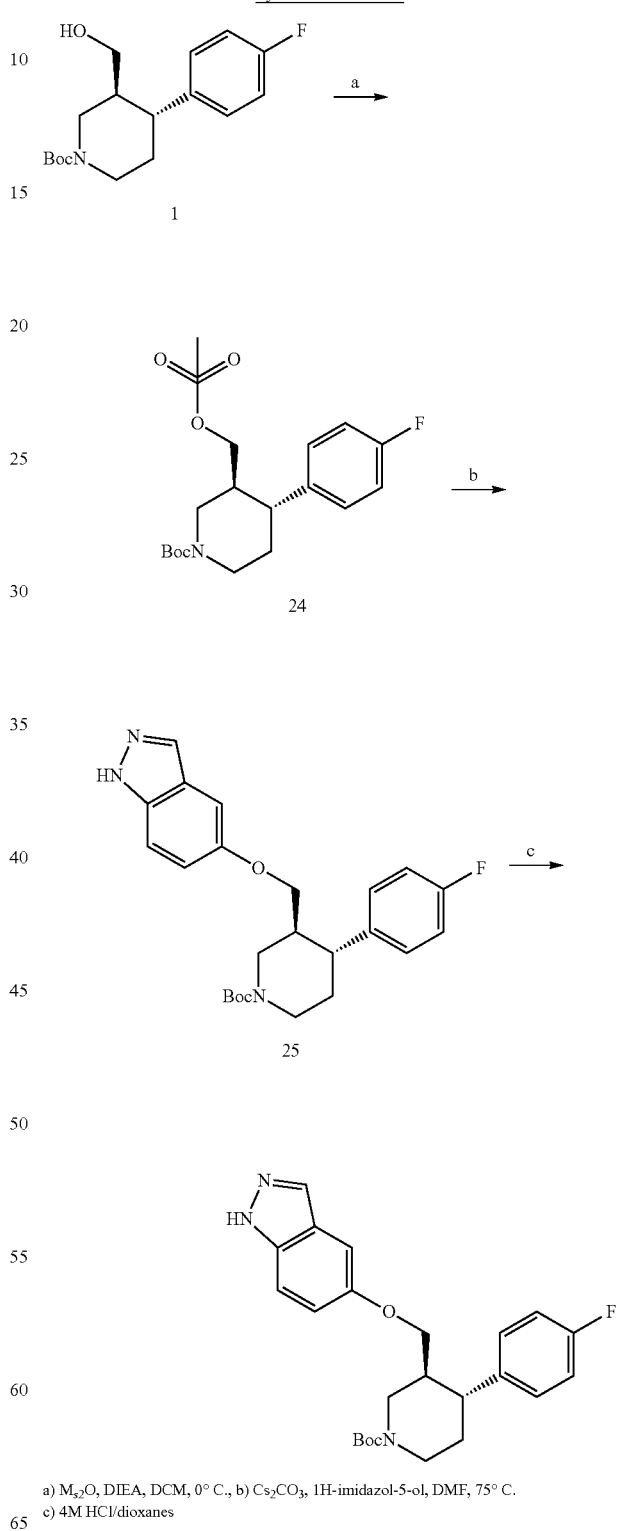

a) Ms$_2$O, DIEA, DCM, 0° C., b) Cs$_2$CO$_3$, 1H-imidazol-5-ol, DMF, 75° C.
c) 4M HCl/dioxanes Preparation of (3S,4R)-tert-butyl 4-(4-fluorophenyl)-3-(((methylsulfonyl)oxy)methyl)piperidine-1-carboxylate (24)

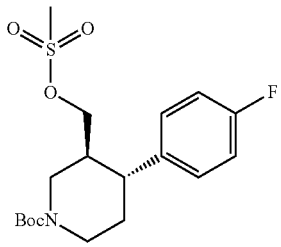 [SMILES: CC(C)(C)OC(=O)N1CC[C@@H](c2ccc(F)cc2)[C@H](COS(C)(=O)=O)C1]

To a 0° C. solution of (3S,4R)-tert-butyl 4-(4-fluorophenyl)-3-(hydroxymethyl)piperidine-1-carboxylate (0.250 g, 0.808 mmol) in 5 mL DCM was added diisopropylethylamine (0.423 mL, 2.42 mmol) followed by methanesulfonylanhydride (0.282 g, 1.62 mmol). The reaction was allowed to warm to room temperature and stirred overnight. Washed with water (1×), then brine (1×), dried over $MgSO_4$, and concentrated in vacuo to give (3S,4R)-tert-butyl 4-(4-fluorophenyl)-3-(((methylsulfonyl)oxy)methyl)piperidine-1-carboxylate as a yellow solid (0.342 g crude). Took to next step without further purification.

Preparation of tert-butyl (3S,4R)-3-(((1H-indazol-5-yl)oxy)methyl)-4-(4-fluorophenyl)piperidine-1-carboxylate (25)

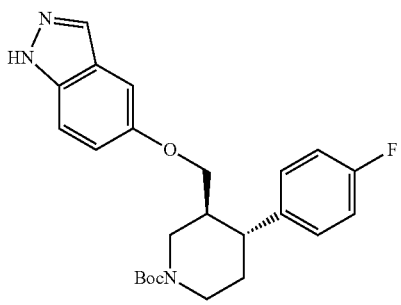 [SMILES: CC(C)(C)OC(=O)N1CC[C@@H](c2ccc(F)cc2)[C@H](COc2ccc3[nH]ncc3c2)C1]

To a 25 mL flask equipped with a stir bar and 1.5 mL DMF was added cesium carbonate (0.579 g, 1.778 mmol) and 1H-indazol-5-ol (0.217 g, 1.616 mmol) at 0° C. The reaction mixture was stirred for twenty minutes under argon and then (3S,4R)-tert-butyl 4-(4-fluorophenyl)-3-(((methylsulfonyl)oxy)methyl)piperidine-1-carboxylate (23) in 1.5 mL was slowly added. The reaction was then heated to 75° C. and stirred overnight. The reaction was quenched with $NH_4Cl$ and diluted with EtOAc and water. The layers were separated and the organic layer was washed 2× with brine, dried over $MgSO_4$, and concentrated in vacuo. Purification proceeded using preparative chromatography (MeOH/DCM) to give as a white amorphous solid tert-butyl (3S,4R)-3-(((1H-indazol-5-yl)oxy)methyl)-4-(4-fluorophenyl)piperidine-1-carboxylate (0.051 g, 0.120 mmol, 15% yield). $^1$H NMR ($CD_3OD$, 500 MHz) δ: 7.85, 7.40, 7.27-7.20, 7.04-6.98, 6.90, 4.50-4.40, 4.21, 3.72, 3.62, 2.89, 2.78, 2.15-2.07, 1.82-1.60, 1.48.

Preparation of tert-butyl 5-(((3S,4R)-1-(tert-butoxycarbonyl)-4-(4-fluorophenyl)piperidin-3-yl)methoxy)-6-fluoro-1H-indazole-1-carboxylate (26)

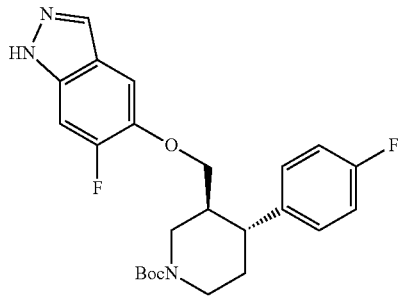 [SMILES: CC(C)(C)OC(=O)N1CC[C@@H](c2ccc(F)cc2)[C@H](COc2cc3cn[nH]c3cc2F)C1]

Intermediate 26 was synthesized as described for intermediate 15 replacing sesamol with intermediate 34. $^1$H NMR (400 MHz, Chloroform-d) δ 7.98 (s, 1H), 7.90 (d, J=11.0 Hz, 1H), 7.19-7.14 (m, 2H), 6.97 (t, J=8.5 Hz, 2H), 6.90 (d, J=7.8 Hz, 1H), 4.49 (d, J=13.3 Hz, 1H), 4.22 (s, 1H), 3.79 (dd, J=9.4, 2.7 Hz, 1H), 3.61 (dd, J=9.3, 6.1 Hz, 1H), 2.94-2.86 (m, 2H), 2.16-2.07 (m, 1H), 1.84 (d, J=12.8 Hz, 3H), 1.71 (s, 9H), 1.51 (s, 9H).

Example 18: 5-(((3S,4R)-4-(4-fluorophenyl)piperidin-3-yl)methoxy)-1H-indazole (CCG224061) (E18)

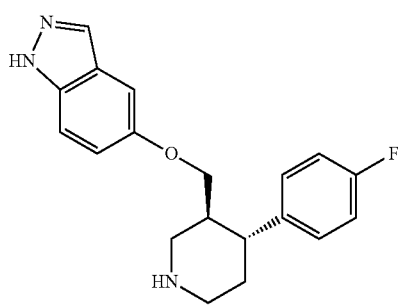 [SMILES: Fc1ccc([C@@H]2CCNC[C@H]2COc2ccc3[nH]ncc3c2)cc1]

Prepared from Intermediate 25 as described for Example 7. $^1$H NMR (DMSO, 400 MHz) δ: 12.91, 7.86, 7.38, 7.29, 7.11, 6.92-6.85, 3.61-3.47, 3.28, 3.00, 2.58, 2.05, 1.68-1.54.

Example 19: 5-((3S,4R)-3-((benzo[d][1,3]dioxol-5-yloxy)methyl)piperidin-4-yl)-N-benzyl-2-fluorobenzamide (CCG258202) (E19)

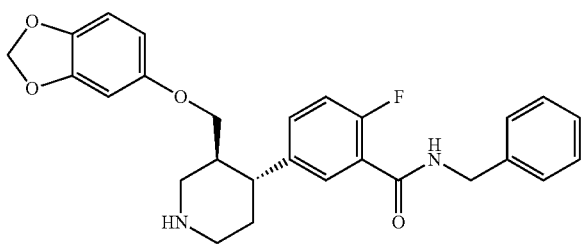 [SMILES: O=C(NCc1ccccc1)c1cc([C@@H]2CCNC[C@H]2COc2ccc3c(c2)OCO3)ccc1F]

Prepared from Intermediate 17k as described for Example 7. $^1$H NMR (400 MHz, Methanol-d4) δ 7.61 (dd, J=6.9, 2.4

Hz, 1H), 7.41 (ddd, J=8.5, 4.8, 2.4 Hz, 1H), 7.37-7.28 (m, 4H), 7.27-7.22 (m, 1H), 7.15 (dd, J=10.6, 8.5 Hz, 1H), 6.59 (d, J=8.5 Hz, 1H), 6.35 (d, J=2.5 Hz, 1H), 6.14 (dd, J=8.5, 2.5 Hz, 1H), 5.83 (d, J=1.3 Hz, 2H), 4.57 (s, 2H), 3.59 (dd, J=9.7, 3.0 Hz, 1H), 3.50 (dd, J=9.7, 6.5 Hz, 1H), 3.42 (dd, J=12.5, 3.8 Hz, 1H), 3.23 (d, J=12.5 Hz, 1H), 2.90-2.76 (m, 3H), 2.19 (dtd, J=16.0, 8.1, 4.0 Hz, 1H), 1.89-1.82 (m, 2H).

Example 20: 5-((3S,4R)-3-((benzo[d][1,3]dioxol-5-yloxy)methyl)piperidin-4-yl)-2-fluoro-N-phenethyl-benzamide (CCG258201) (E20)

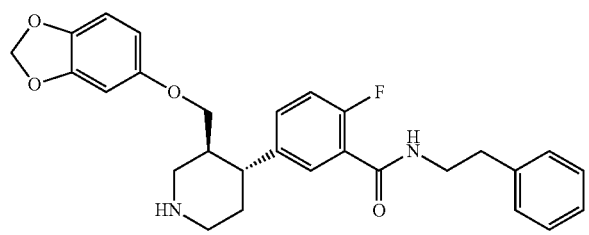 [SMILES: O=C(NCCc1ccccc1)c1cc([C@@H]2CCNC[C@H]2COc2ccc3c(c2)OCO3)ccc1F]

Prepared from Intermediate 17l as described for Example 7. $^1$H NMR (400 MHz, Methanol-$d_4$) δ 7.54 (dd, J=7.0, 2.4 Hz, 1H), 7.39 (ddd, J=8.5, 4.8, 2.4 Hz, 1H), 7.30-7.23 (m, 4H), 7.22-7.16 (m, 1H), 7.11 (dd, J=10.6, 8.5 Hz, 1H), 6.60 (d, J=8.5 Hz, 1H), 6.34 (d, J=2.4 Hz, 1H), 6.14 (dd, J=8.5, 2.5 Hz, 1H), 5.82 (s, 2H), 3.62-3.54 (m, 3H), 3.47 (dd, J=9.6, 6.6 Hz, 1H), 3.39-3.32 (m, 1H), 3.17-3.10 (m, 1H), 2.89 (dd, J=8.1, 6.7 Hz, 2H), 2.80-2.64 (m, 3H), 2.11 (dtd, J=11.0, 7.3, 3.3 Hz, 1H), 1.83-1.71 (m, 2H).

Example 21: 5-((3S,4R)-3-((benzo[d][1,3]dioxol-5-yloxy)methyl)piperidin-4-yl)-2-fluoro-N-(pyridin-3-ylmethyl)benzamide (CCG258203) (E21)

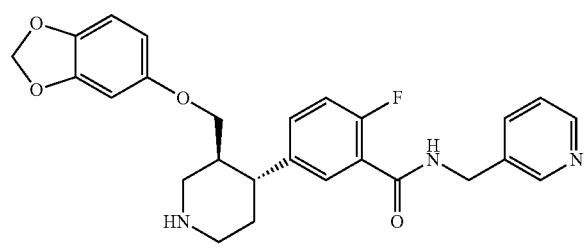 [SMILES: O=C(NCc1cccnc1)c1cc([C@@H]2CCNC[C@H]2COc2ccc3c(c2)OCO3)ccc1F]

Prepared from Intermediate 17m as described for Example 7. $^1$H NMR (400 MHz, Methanol-d4) δ 8.57 (d, J=2.2 Hz, 1H), 8.44 (dd, J=4.9, 1.6 Hz, 1H), 7.85 (dt, J=8.0, 1.9 Hz, 1H), 7.65 (dd, J=6.9, 2.4 Hz, 1H), 7.44 (ddd, J=12.8, 7.9, 4.8 Hz, 2H), 7.20 (dd, J=10.5, 8.5 Hz, 1H), 6.61 (d, J=8.5 Hz, 1H), 6.38 (d, J=2.5 Hz, 1H), 6.17 (dd, J=8.5, 2.5 Hz, 1H), 5.85 (s, 2H), 4.61 (s, 2H), 3.64 (td, J=11.6, 10.6, 3.1 Hz, 2H), 3.55 (dd, J=9.9, 6.0 Hz, 1H), 3.47 (d, J=12.8 Hz, 1H), 3.19-3.04 (m, 2H), 3.07-2.96 (m, 1H), 2.45-2.34 (m, 1H), 2.04 (d, J=3.4 Hz, 1H).

Example 22: 5-((3S,4R)-3-((benzo[d][1,3]dioxol-5-yloxy)methyl)piperidin-4-yl)-2-fluoro-N-(pyridin-4-ylmethyl)benzamide (CCG258204) (E22)

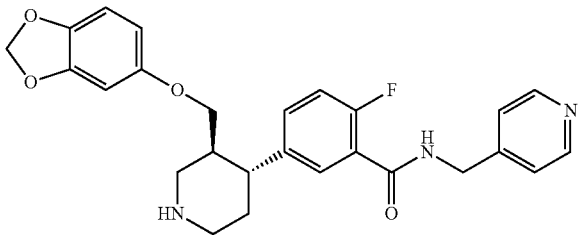 [SMILES: O=C(NCc1ccncc1)c1cc([C@@H]2CCNC[C@H]2COc2ccc3c(c2)OCO3)ccc1F]

Prepared from Intermediate 17n as described for Example 7. $^1$H NMR (400 MHz, Methanol-d4) δ 8.49-8.44 (m, 2H), 7.65 (dd, J=6.9, 2.4 Hz, 1H), 7.44 (ddd, J=8.5, 4.8, 2.4 Hz, 1H), 7.41-7.37 (m, 2H), 7.18 (dd, J=10.6, 8.5 Hz, 1H), 6.59 (d, J=8.5 Hz, 1H), 6.34 (d, J=2.5 Hz, 1H), 6.14 (dd, J=8.5, 2.5 Hz, 1H), 5.83 (d, J=1.4 Hz, 2H), 4.62 (s, 2H), 3.58 (dd, J=9.7, 3.0 Hz, 1H), 3.49 (dd, J=9.7, 6.4 Hz, 1H), 3.37 (dd, J=12.7, 3.8 Hz, 1H), 3.22-3.14 (m, 1H), 2.85-2.69 (m, 3H), 2.21-2.11 (m, 1H), 1.86-1.75 (m, 2H).

Example 23: 5-((3S,4R)-3-((benzo[d][1,3]dioxol-5-yloxy)methyl)piperidin-4-yl)-2-fluoro-N-(2-(pyridin-2-yl)ethyl)benzamide (CCG258205) (E23)

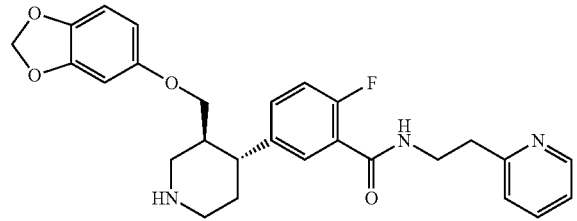 [SMILES: O=C(NCCc1ccccn1)c1cc([C@@H]2CCNC[C@H]2COc2ccc3c(c2)OCO3)ccc1F]

Prepared from Intermediate 17o as described for Example 7. $^1$H NMR (400 MHz, Methanol-d4) δ 8.46 (ddd, J=5.0, 1.8, 1.0 Hz, 1H), 7.76 (td, J=7.7, 1.8 Hz, 1H), 7.59 (dd, J=6.9, 2.4 Hz, 1H), 7.42 (ddd, J=8.5, 4.7, 2.4 Hz, 1H), 7.36 (dt, J=7.8, 1.1 Hz, 1H), 7.27 (ddd, J=7.5, 5.0, 1.2 Hz, 1H), 7.17 (dd, J=10.5, 8.6 Hz, 1H), 6.63 (d, J=8.5 Hz, 1H), 6.40 (d, J=2.5 Hz, 1H), 6.19 (dd, J=8.5, 2.5 Hz, 1H), 5.85 (s, 2H), 3.74 (t, J=7.1 Hz, 2H), 3.71-3.63 (m, 2H), 3.60-3.49 (m, 2H), 3.21-3.11 (m, 2H), 3.08 (t, J=7.1 Hz, 2H), 3.02 (dd, J=11.1, 5.8 Hz, 1H), 2.48-2.37 (m, 1H), 2.09-2.00 (m, 2H).

Example 24: 5-((3S,4R)-3-((benzo[d][1,3]dioxol-5-yloxy)methyl)piperidin-4-yl)-2-fluoro-N-(2-(pyridin-4-yl)ethyl)benzamide (CCG258206) (E24)

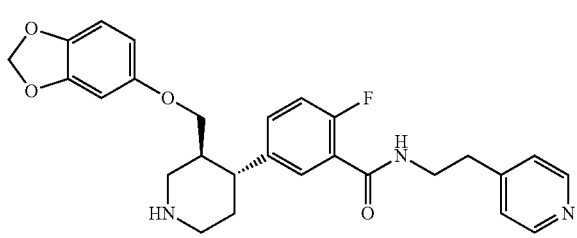 [SMILES: O=C(NCCc1ccncc1)c1cc([C@@H]2CCNC[C@H]2COc2ccc3c(c2)OCO3)ccc1F]

Prepared from Intermediate 17p as described for Example 7. $^1$H NMR (500 MHz, Methanol-d$_4$) δ 8.44 (d, J=5.1 Hz, 2H), 7.55 (dd, J=6.8, 2.4 Hz, 1H), 7.43 (ddd, J=8.5, 4.8, 2.4 Hz, 1H), 7.39-7.35 (m, 2H), 7.17 (dd, J=10.5, 8.5 Hz, 1H), 6.63 (d, J=8.5 Hz, 1H), 6.41 (d, J=2.5 Hz, 1H), 6.19 (dd, J=8.5, 2.5 Hz, 1H), 5.85 (s, 2H), 3.72-3.64 (m, 4H), 3.59-3.50 (m, 2H), 3.22-3.14 (m, 2H), 3.04 (ddd, J=11.4, 9.3, 6.9 Hz, 1H), 2.98 (t, J=7.1 Hz, 2H), 2.45 (dddt, J=11.5, 8.4, 5.9, 3.2 Hz, 1H), 2.09-2.02 (m, 2H).

Example 25: 5-((3S,4R)-3-((benzo[d][1,3]dioxol-5-yloxy)methyl)piperidin-4-yl)-2-fluoro-N-(2-(pyridin-3-yl)ethyl)benzamide (CCG258207) (E25)

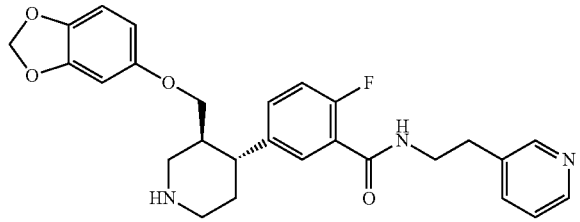 [SMILES: O=C(NCCc1cccnc1)c1cc([C@@H]2CCNC[C@H]2COc2ccc3c(c2)OCO3)ccc1F]

Prepared from intermediate 17q as described for Example 7. $^1$H NMR (400 MHz, Methanol-d4) δ 8.45 (d, J=1.7 Hz, 1H), 8.39 (dd, J=5.0, 1.6 Hz, 1H), 7.78 (dt, J=7.9, 1.9 Hz, 1H), 7.52 (dd, J=6.9, 2.4 Hz, 1H), 7.38 (dddd, J=10.7, 7.8, 4.9, 1.7 Hz, 2H), 7.13 (dd, J=10.5, 8.5 Hz, 1H), 6.61 (d, J=8.5 Hz, 1H), 6.36 (d, J=2.5 Hz, 1H), 6.16 (dd, J=8.5, 2.5 Hz, 1H), 5.84 (d, J=1.2 Hz, 2H), 3.64 (t, J=7.0 Hz, 2H), 3.59 (dd, J=9.7, 3.0 Hz, 1H), 3.53-3.42 (m, 2H), 3.27 (d, J=12.7 Hz, 1H), 2.95 (t, J=7.0 Hz, 2H), 2.86 (qd, J=12.4, 11.8, 3.8 Hz, 3H), 2.21 (tq, J=7.8, 4.4, 3.8 Hz, 1H), 1.91-1.79 (m, 2H).

Example 26: N-((1H-pyrazol-5-yl)methyl)-5-((3S,4R)-3-((benzo[d][1,3]dioxol-5-yloxy)methyl)piperidin-4-yl)-2-fluorobenzamide (CCG258208) (E26)

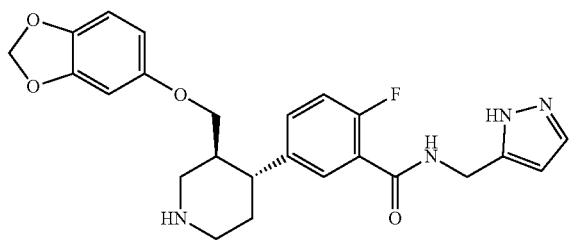 [SMILES: O=C(NCc1ccn[nH]1)c1cc([C@@H]2CCNC[C@H]2COc2ccc3c(c2)OCO3)ccc1F]

Prepared from intermediate 17r as described for Example 7. $^1$H NMR (400 MHz, Methanol-d4) δ 7.64 (dd, J=6.9, 2.4 Hz, 1H), 7.57 (s, 1H), 7.42 (ddd, J=8.5, 4.8, 2.4 Hz, 1H), 7.15 (dd, J=10.6, 8.5 Hz, 1H), 6.60 (d, J=8.5 Hz, 1H), 6.36 (d, J=2.5 Hz, 1H), 6.29 (d, J=2.2 Hz, 1H), 6.15 (dd, J=8.5, 2.5 Hz, 1H), 5.84 (q, J=1.1 Hz, 2H), 4.60 (s, 2H), 3.60 (dd, J=9.7, 3.0 Hz, 1H), 3.51 (dd, J=9.8, 6.4 Hz, 1H), 3.45 (dd, J=12.7, 3.8 Hz, 1H), 3.26 (d, J=12.9 Hz, 1H), 2.92-2.80 (m, 3H), 2.27-2.16 (m, 1H), 1.92-1.79 (m, 2H).

Example 27: N-((1H-imidazol-2-yl)methyl)-5-((3S,4R)-3-((benzo[d][1,3]dioxol-5-yloxy)methyl)piperidin-4-yl)-2-fluorobenzamide (CCG258209) (E27)

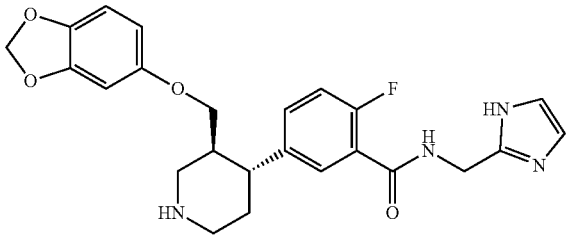 [SMILES: O=C(NCc1ncc[nH]1)c1cc([C@@H]2CCNC[C@H]2COc2ccc3c(c2)OCO3)ccc1F]

Prepared from intermediate 17s as described for Example 7. $^1$H NMR (400 MHz, Methanol-d$_4$) δ 7.72 (dd, J=6.9, 2.4 Hz, 1H), 7.43 (ddd, J=8.6, 4.8, 2.4 Hz, 1H), 7.17 (dd, J=10.7, 8.5 Hz, 1H), 6.98 (s, 2H), 6.60 (d, J=8.5 Hz, 1H), 6.37 (d, J=2.5 Hz, 1H), 6.16 (dd, J=8.5, 2.5 Hz, 1H), 5.84 (d, J=1.4 Hz, 2H), 4.62 (s, 2H), 3.62 (td, J=11.0, 10.4, 3.2 Hz, 2H), 3.54 (dd, J=9.8, 6.3 Hz, 1H), 3.40 (d, J=12.6 Hz, 1H), 3.08-2.90 (m, 3H), 2.40-2.29 (m, 1H), 2.01-1.90 (m, 2H).

Example 28: N-(2-(1H-imidazol-4-yl)ethyl)-5-((3S,4R)-3-((benzo[d][1,3]dioxol-5-yloxy)methyl)piperidin-4-yl)-2-fluorobenzamide (CCG258210) (E28)

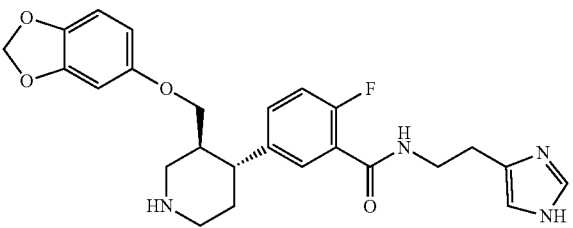 [SMILES: O=C(NCCc1c[nH]cn1)c1cc([C@@H]2CCNC[C@H]2COc2ccc3c(c2)OCO3)ccc1F]

Prepared from intermediate 17t as described for Example 7. $^1$H NMR (400 MHz, Methanol-d4) δ 7.57 (dd, J=6.9, 2.2 Hz, 1H), 7.40 (ddd, J=8.4, 4.8, 2.4 Hz, 1H), 7.14 (dd, J=10.6, 8.5 Hz, 1H), 7.62-7.59 (m, 1H), 6.89 (s, 1H), 6.62 (d, J=8.5 Hz, 1H), 6.37 (d, J=2.5 Hz, 1H), 6.17 (dd, J=8.5, 2.5 Hz, 1H), 5.84 (s, 2H), 3.66-3.59 (m, 3H), 3.57-3.47 (m, 2H), 3.33 (d, J=12.3 Hz, 2H), 3.01-2.84 (m, 5H), 2.31-2.22 (m, 1H), 1.96-1.89 (m, 2H).

Example 29: 5-((3S,4R)-3-(((1H-indazol-6-yl)oxy)methyl)piperidin-4-yl)-2-fluoro-N-(pyridin-2-ylmethyl)benzamide (E29)

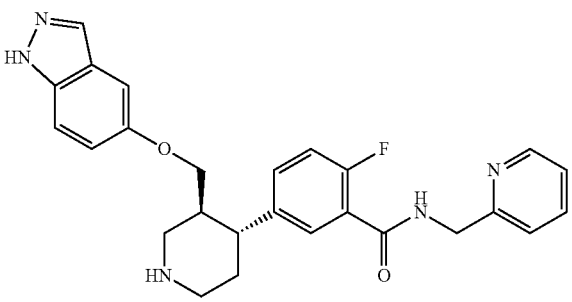 [SMILES: O=C(NCc1ccccn1)c1cc([C@@H]2CCNC[C@H]2COc2ccc3[nH]ncc3c2)ccc1F]

Example 29 was prepared from intermediate 23b as described previously for Example 17. ¹H NMR (400 MHz, Methanol-d4) δ 8.74 (d, J=5.3 Hz, 1H), 8.49 (td, J=7.9, 1.6 Hz, 1H), 7.98 (d, J=8.1 Hz, 1H), 7.92 (ddd, J=7.4, 5.8, 1.2 Hz, 1H), 7.87 (s, 1H), 7.80 (dd, J=6.9, 2.4 Hz, 1H), 7.54 (ddd, J=8.5, 4.8, 2.4 Hz, 1H), 7.41 (d, J=9.0 Hz, 1H), 7.25 (dd, J=10.9, 8.5 Hz, 1H), 7.03 (dd, J=9.0, 2.3 Hz, 1H), 6.95 (d, J=2.2 Hz, 1H), 4.88 (s, 2H), 3.83-3.65 (m, 3H), 3.55 (d, J=12.7 Hz, 1H), 3.25-3.08 (m, 3H), 2.60-2.48 (m, 1H), 2.08 (dt, J=9.4, 4.7 Hz, 2H).

Example 30: 6-fluoro-5-(((3S,4R)-4-(4-fluorophenyl)piperidin-3-yl)methoxy)-1H-indazole (E30)

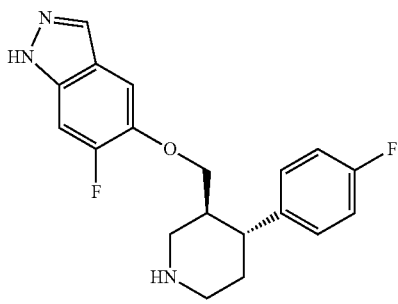 [SMILES: Fc1ccc([C@@H]2CCNC[C@H]2COc2cc3cn[nH]c3cc2F)cc1]

Prepared from Intermediate 26 as described for Example 7. ¹H NMR (500 MHz, Methanol-d4) δ 7.86 (d, J=1.0 Hz, 1H), 7.31-7.19 (m, 3H), 7.01 (td, J=8.8, 8.4, 5.9 Hz, 3H), 3.75 (dd, J=9.6, 2.9 Hz, 1H), 3.67-3.60 (m, 1H), 3.42 (dd, J=13.1, 4.1 Hz, 1H), 3.15 (d, J=12.5 Hz, 1H), 2.77 (ddq, J=15.9, 7.8, 3.7 Hz, 3H), 2.19 (dtd, J=10.8, 7.5, 3.4 Hz, 1H), 1.85-1.72 (m, 2H).

Synthetic Scheme 5

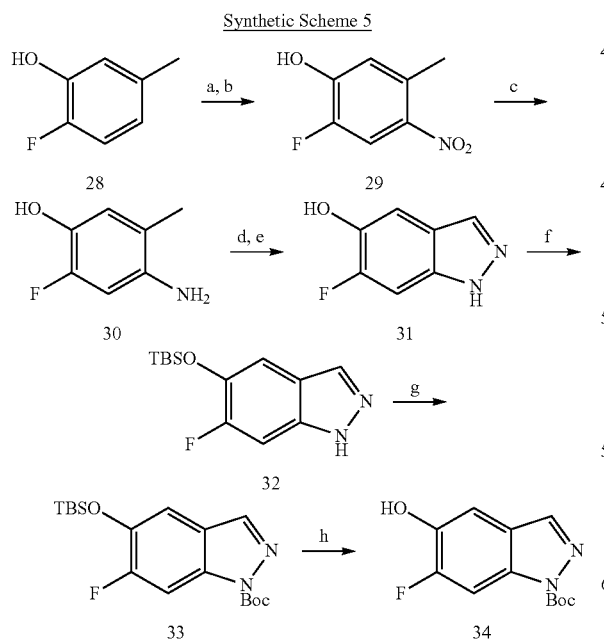

a) AcOH, H₂SO₄, 0° C., then NaNO₂, b) HNO₃, c) 10% Pd/C, H₂, EtOH, THF,
d) KOAc, Ac₂O, CHCl₃, 0° C., then isoamyl nitrite and 80° C.,
e) 6N HCl, MeOH, f) TBSCl, DIEA, ImH, DCM, g) Boc₂O,
DIEA, DMAP, THF, h) TBAF, THF Preparation of 2-fluoro-5-methyl-4-nitrophenol (29)

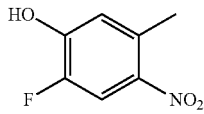

Added 2-fluoro-5-methylphenol (0.200 g, 1.59 mmol) to a 5 mL flask followed by AcOH (0.40 mL) and H₂SO₄ (0.058 mL) at 0° C. (ice-salt bath). Then sodium nitrite (0.29 mL of 5.5 M in water) was slowly added to the reaction to give a burnt orange color. The reaction was stirred for thirty minutes on the ice bath. Poured reaction over ice and then filtered off a light orange solid. Warmed 20% nitric Acid in water (5 mL) to 45° C. then added the orange solid in portions while stirring. The reaction was stirred for twenty minutes then diluted with water and cooled. The light orange solid was filtered off to give 2-fluoro-5-methyl-4-nitrophenol as a light orange solid (0.124 g, 46% yield). ¹H NMR (500 MHz, DMSO-d₆) δ 13.86 (s, 1H), 7.42 (d, J=11.6 Hz, 1H), 6.47 (dq, J=8.2, 1.3 Hz, 1H), 2.23 (d, J=1.3 Hz, 3H).

Preparation of 4-amino-2-fluoro-5-methylphenol (30)

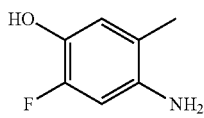

To a dry round bottom flask was added intermediate 29 (2.64 g, 15.42 mmol), 10% Pd/C (0.528 g), EtOH (20 mL), and THF (20 mL). Argon was bubbled through the reaction mixture and then the atmosphere was replaced with H₂. The reaction was stirred overnight at room temperature. Filtered the reaction through a pad of celite with EtOH/THF to give 4-amino-2-fluoro-5-methylphenol as an off white solid (2.0 g, 92%). ¹H NMR (500 MHz, DMSO-d₆) δ 8.48 (s, 1H), 6.53 (d, J=9.8 Hz, 1H), 6.38 (d, J=13.2 Hz, 1H), 4.42 (s, 2H), 1.94 (s, 3H).

Preparation of 6-fluoro-1H-indazol-5-ol (31)

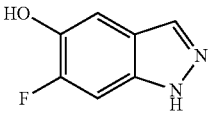 [SMILES: Oc1cc2cn[nH]c2cc1F]

In a pressure vessel intermediate 30 (0.659 g, 4.67 mmol) and potassium acetate (11.39 mmol, 1.12 g) were dissolved in chloroform (30 mL) at 0° C. Then acetic anhydride (21.01 mmol, 1.98 mL) was added drop wise to the reaction. The reaction was then warmed to room temperature and stirred for thirty minutes. After thirty minutes the reaction was heated to 80° C. and isopentyl nitrite (5.14 mmol, 0.69 mL) was added drop wise. The reaction was further stirred at 80° C. overnight turning a dark brown color. The reaction was neutralized with NaHCO₃ to pH 7. Dichloromethane was then added to dilute the reaction and the layers were separated. The organic layer was then washed 2× with NaCl, dried over MgSO₄, and concentrated. Dissolved resulting residue in MeOH (15 mL) and 6N HCl (15 mL) and refluxed overnight at 40° C. Neutralized the reaction with NaOH and then concentrated off the MeOH. Extracted the aqueous layer with ethyl acetate 2×, then washed the ethyl acetate 2× with NaCl, dried over MgSO₄, and concentrated to give a brown residue. Purified the resulting residue using a gradient of 40%-100% EtOAc/Hexanes to give 6-fluoro-1H-indazol-5-ol (31) (1.571 g, 60%). $^1$H NMR (400 MHz, DMSO-d6) δ 12.83 (s, 1H), 9.55 (s, 1H), 7.88 (s, 1H), 7.30 (dd, J=10.9, 1.1 Hz, 1H), 7.17 (d, J=8.5 Hz, 1H).

Preparation of 5-((tert-butyldimethylsilyl)oxy)-6-fluoro-1H-indazole (32)

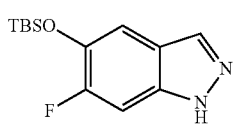 [SMILES: CC(C)(C)[Si](C)(C)Oc1cc2cn[nH]c2cc1F]

Intermediate 32 was prepared as described for intermediate 18 replacing 1H-indazol-5-ol with intermediate 31. $^1$H NMR (400 MHz, DMSO-d$_6$) δ 12.98 (s, 1H), 7.95 (s, 1H), 7.37 (d, J=10.6 Hz, 1H), 7.31 (d, J=8.2 Hz, 1H), 0.99 (s, 9H), 0.18 (d, J=0.8 Hz, 6H).

Preparation of tert-butyl 5-((tert-butyldimethylsilyl)oxy)-6-fluoro-1H-indazole-1-carboxylate (33)

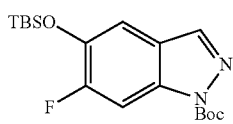 [SMILES: CC(C)(C)OC(=O)n1ncc2cc(O[Si](C)(C)C(C)(C)C)c(F)cc21]

Intermediate 33 was prepared as described for intermediate 19 replacing intermediate 18 with intermediate 32. $^1$H NMR (400 MHz, DMSO-d6) δ 8.30 (s, 1H), 7.81 (d, J=10.8 Hz, 1H), 7.50 (d, J=8.2 Hz, 1H), 1.63 (s, 9H), 0.98 (s, 9H), 0.20 (s, 6H).

Preparation of tert-butyl 6-fluoro-5-hydroxy-1H-indazole-1-carboxylate (34)

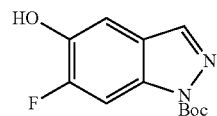

Intermediate 34 was prepared as described for intermediate 20 replacing intermediate 19 with intermediate 33. $^1$H NMR (400 MHz, Chloroform-d) δ 8.06 (d, J=0.9 Hz, 1H), 7.95 (d, J=10.7 Hz, 1H), 7.28 (d, J=8.2 Hz, 2H), 5.48 (s, 1H), 1.71 (s, 9H).

Synthetic Scheme 6

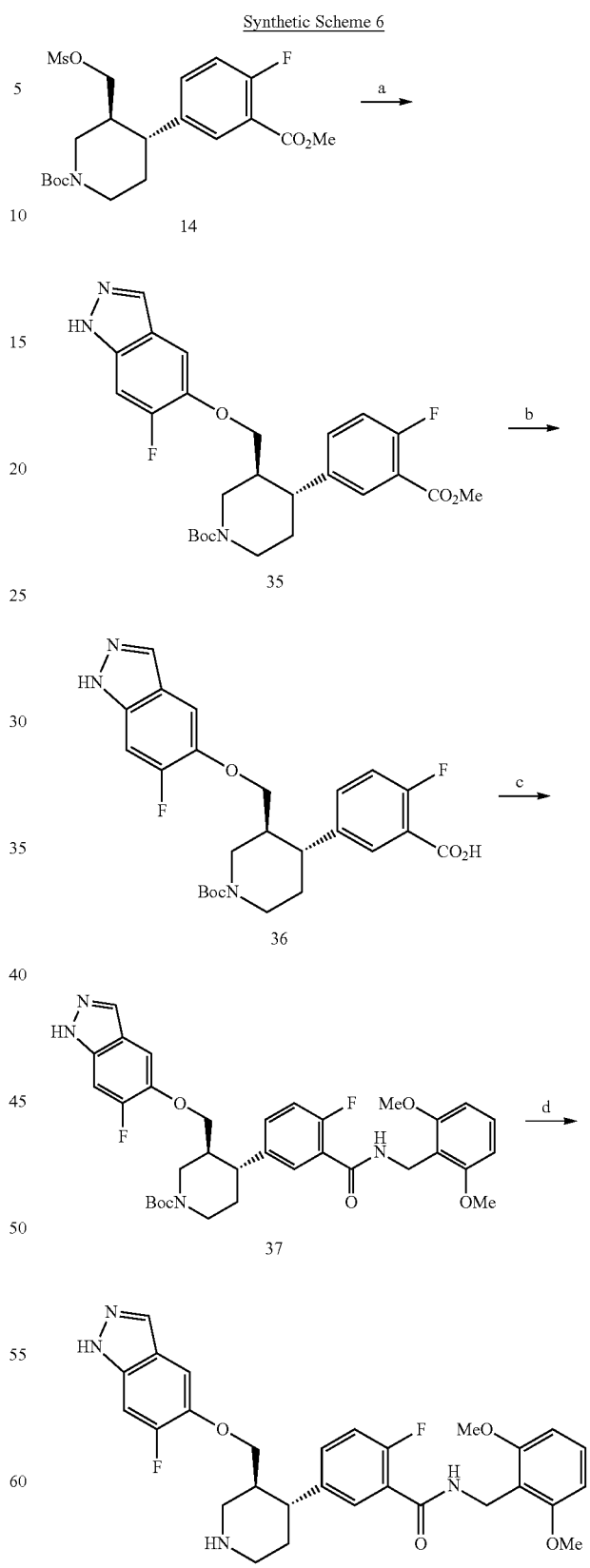

a) NaH, 32, DMF, b) NaOH, MeOH, H₂O, c) DIEA, EDC, HOBt, 2,6-dimethoxy benzylamine, d) 4M HCl/dioxanes Preparation of tert-butyl 5-(((3S,4R)-1-(tert-butoxycarbonyl)-4-(4-fluoro-3-(methoxycarbonyl)phenyl)piperidin-3-yl)methoxy)-6-fluoro-1H-indazole-1-carboxylate (35)

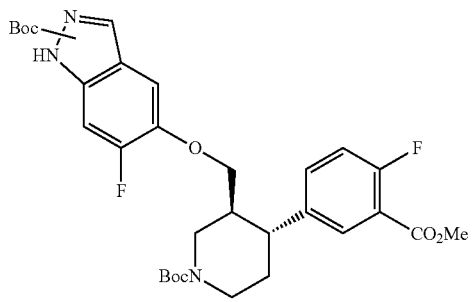

Intermediate 35 was prepared as described for intermediate 15 replacing sesamol with intermediate 34.

Preparation of 5-((3S,4R)-1-(tert-butoxycarbonyl)-3-(((6-fluoro-1H-indazol-5-yl)oxy)methyl)piperidin-4-yl)-2-fluorobenzoic acid (36)

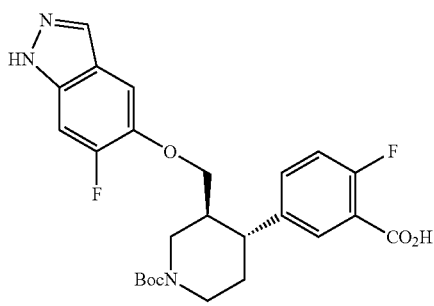 [SMILES: CC(C)(C)OC(=O)N1CC[C@@H](c2ccc(F)c(C(=O)O)c2)[C@H](COc2cc3cn[nH]c3cc2F)C1]

Intermediate 36 was prepared as described for intermediate 16 replacing intermediate 15 with intermediate 35. $^1$H NMR (400 MHz, Chloroform-d) δ 9.19 (s, 1H), 7.83 (d, J=1.0 Hz, 1H), 7.77 (dd, J=7.4, 2.2 Hz, 1H), 7.40 (ddd, J=7.6, 4.3, 2.4 Hz, 1H), 7.23 (d, J=10.2 Hz, 1H), 7.12 (dd, J=10.5, 8.4 Hz, 1H), 6.91 (d, J=7.8 Hz, 1H), 4.48 (d, J=13.0 Hz, 1H), 4.30 (s, 1H), 3.87 (d, J=10.2 Hz, 1H), 3.67 (dd, J=10.4, 5.6 Hz, 1H), 2.99 (t, J=12.4 Hz, 1H), 2.89 (d, J=17.8 Hz, 2H), 2.05 (s, 1H), 1.91-1.71 (m, 2H), 1.50 (s, 9H).

Preparation of tert-butyl (3S,4R)-4-(3-((2,6-dimethoxybenzyl)carbamoyl)-4-fluorophenyl)-3-(((6-fluoro-1H-indazol-5-yl)oxy)methyl)piperidine-1-carboxylate (37)

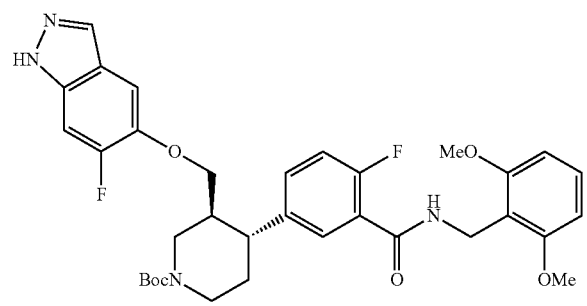 [SMILES: COc1cccc(OC)c1CNC(=O)c1cc([C@@H]2CCN(C(=O)OC(C)(C)C)C[C@H]2COc2cc3cn[nH]c3cc2F)ccc1F]

Intermediate 37 was prepared as described for intermediate 17i replacing intermediate 16 with intermediate 36. $^1$H NMR (500 MHz, Chloroform-d) δ 8.01 (dd, J=7.5, 2.4 Hz, 1H), 7.87 (s, 1H), 7.47 (dt, J=12.1, 5.3 Hz, 1H), 7.21 (d, J=8.3 Hz, 1H), 7.15 (d, J=10.3 Hz, 1H), 6.98 (dd, J=11.6, 8.4 Hz, 1H), 6.89 (d, J=7.8 Hz, 1H), 6.57 (d, J=8.4 Hz, 2H), 4.80-4.76 (m, 2H), 4.55-4.48 (m, 1H), 4.25 (s, 1H), 4.03 (hept, J=6.0 Hz, 1H), 3.85 (s, 6H), 3.70 (dd, J=9.5, 2.8 Hz, 1H), 3.55 (dd, J=9.6, 6.6 Hz, 1H), 2.86 (dd, J=13.4, 11.2 Hz, 2H), 2.16 (s, 1H), 1.82-1.67 (m, 2H), 1.50 (s, 9H).

Example 31: N-(2,6-dimethoxybenzyl)-2-fluoro-5-((3S,4R)-3-(((6-fluoro-1H-indazol-5-yl)oxy)methyl)piperidin-4-yl)benzamide (E31)

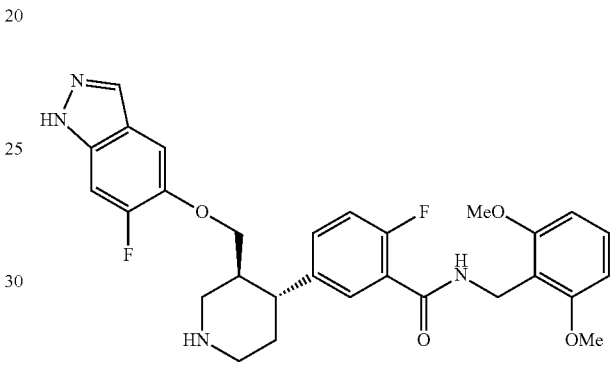

Prepared from intermediate 37 as described for Example 7. $^1$H NMR (400 MHz, Methanol-d4) δ 8.31 (s, 1H), 7.73-7.69 (m, 1H), 7.46 (s, 1H), 7.41 (d, J=10.3 Hz, 1H), 7.24 (t, J=8.3 Hz, 2H), 7.16 (dd, J=10.8, 8.4 Hz, 1H), 6.64 (d, J=8.4 Hz, 2H), 4.69-4.57 (m, 2H), 3.93-3.87 (m, 1H), 3.83 (s, 6H), 3.80-3.72 (m, 3H), 3.69-3.63 (m, 1H), 3.58-3.51 (m, 1H), 3.30-3.14 (m, 3H), 3.14-3.05 (m, 1H), 2.85 (s, 1H), 2.62 (s, 1H).

Preparation of ((3S,4R)-4-(4-fluorophenyl)-1-methylpiperidin-3-yl)methyl methanesulfonate (38)

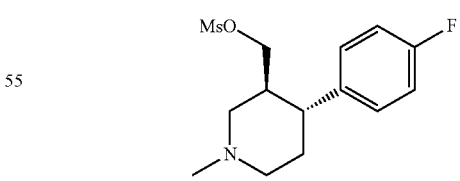

Intermediate 38 was prepared as described for intermediate 14 replacing tert-butyl (3S,4R)-4-(4-fluoro-3-(methoxycarbonyl)phenyl)-3-(hydroxymethyl)piperidine-1-carboxylate (intermediate 13) with ((3S,4R)-4-(4-fluorophenyl)-1-methylpiperidin-3-yl)methanol. The product was used in subsequent reactions without further purification.

Preparation of tert-butyl 5-(((3S,4R)-4-(4-fluorophenyl)-1-methylpiperidin-3-yl)methoxy)-1H-indazole-1-carboxylate (39)

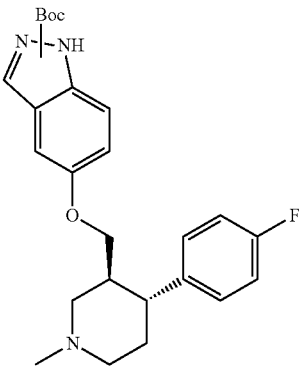

Intermediate 39 was prepared as described for tert-butyl (3S,4R)-3-(((1H-indazol-5-yl)oxy)methyl)-4-(4-fluorophenyl)piperidine-1-carboxylate (25) replacing (3S,4R)-tert-butyl 4-(4-fluorophenyl)-3-(((methylsulfonyl)oxy)methyl)piperidine-1-carboxylate (23) with ((3S,4R)-4-(4-fluorophenyl)-1-methylpiperidin-3-yl)methyl methanesulfonate (38). $^1$H NMR (400 MHz, Chloroform-d) δ 8.02 (d, J=9.2 Hz, 1H), 8.00 (d, J=0.8 Hz, 1H), 7.17 (dt, J=8.5, 6.0 Hz, 3H), 7.07 (dd, J=9.1, 2.4 Hz, 1H), 7.04-6.94 (m, 3H), 6.85 (d, J=2.3 Hz, 1H), 3.93 (dd, J=9.9, 3.1 Hz, 1H), 3.81 (dd, J=9.9, 6.9 Hz, 1H), 3.70 (dd, J=9.3, 3.0 Hz, 1H), 3.57 (dd, J=9.3, 7.0 Hz, 1H), 3.38-3.30 (m, 1H), 3.25 (ddd, J=11.2, 3.8, 1.6 Hz, 1H), 3.12 (ddd, J=11.3, 3.7, 1.8 Hz, 1H), 2.97 (dd, J=16.7, 12.2 Hz, 2H), 2.87 (s, 1H), 2.49 (td, J=11.4, 4.7 Hz, 1H), 2.38 (s, 3H), 2.36 (s, 1H), 2.33-2.20 (m, 2H), 2.08 (dt, J=11.8, 4.2 Hz, 2H), 1.96-1.81 (m, 3H), 1.71 (s, 9H).

Example 32: 5-(((3S,4R)-4-(4-fluorophenyl)-1-methylpiperidin-3-yl)methoxy)-1H-indazole (E32)

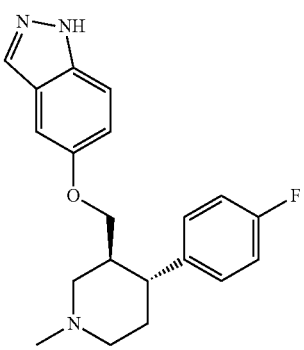 [SMILES: CN1CC[C@@H](c2ccc(F)cc2)[C@H](COc2ccc3[nH]ncc3c2)C1]

Example 32 was from intermediate 39 as described for Example 7. $^1$H NMR (500 MHz, Methanol-d$_4$) δ 7.84 (d, J=1.0 Hz, 1H), 7.38 (dt, J=9.0, 0.8 Hz, 1H), 7.29-7.24 (m, 2H), 7.05-6.95 (m, 3H), 6.89 (d, J=2.3 Hz, 1H), 3.69 (dd, J=9.6, 3.0 Hz, 1H), 3.60 (dd, J=9.7, 6.9 Hz, 1H), 3.29-3.24 (m, 1H), 3.01 (ddt, J=11.5, 4.1, 2.3 Hz, 1H), 2.60 (td, J=11.6, 4.6 Hz, 1H), 2.39 (s, 3H), 2.28 (tdt, J=10.7, 6.7, 3.3 Hz, 1H), 2.20-2.15 (m, 2H), 1.95-1.81 (m, 2H).

Assays for Inhibition of GRKs

GRK1, 2 and 5 kinetic assays were conducted in a buffer containing 20 mM HEPES pH 7.0, 5 µM ATP, 2 mM MgCl$_2$, and 0.025% DDM with 50 nM GRK and either 500 nM bROS or 500 nM soluble substrate tubulin in 5 min reactions. The low salt concentration and DDM were used to maximize GRK activity and disrupt small molecule aggregates from forming, respectively. Reactions were quenched with SDS loading buffer, separated via SDS-PAGE, dried and exposed with a phosphorimaging screen prior to quantification via Typhoon imager, as previously reported (see Thal et al., ACS Chemical Biology 7(11):1830-1839 (2012)). Data was analyzed and inhibition curves were fit via GraphPad Prism.

Results of the assays for inhibition of GRKs are shown in the Table, below.

| Compound | GRK1 IC$_{50}$ (µM) | GRK2 IC$_{50}$ (µM) | GRK5 IC$_{50}$ (µM) |
|---|---|---|---|
| Paroxetine | >100 | 1.13 | >100 |
| E01 | >100 | 2.53 | >100 |
| E02 | 95.3 | 0.42 | >100 |
| E03 | >100 | 3.65 | >100 |
| E04 | >100 | 0.62 | >100 |
| E05 | 59.2 | 3.61 | >100 |
| E06 | >100 | 0.64 | >100 |
| E07 | >100 | 0.44 | 15.2 |
| E08 | >100 | 1.75 | >100 |
| E09 | >100 | 48.5 | >100 |
| E10 | >100 | 12.5 | 61.9 |
| E11 | >100 | 1.53 | 45.5 |
| E12 | >100 | 1.97 | 9.31 |
| E13 | 11.3 | 1.01 | 56.4 |
| E14 | 23.6 | 0.77 | 41.1 |
| E15 | 22.0 | 1.39 | >100 |
| E16 | 16.6 | 1.21 | 33.6 |
| E17 | >100 | 0.32 | >100 |
| E18 | 65.7 | 0.07 | 12.8 |
| E19 | >100 | 0.77 | 84.3 |
| E20 | >100 | 2.68 | >100 |
| E21 | >100 | 1.52 | 76.3 |
| E22 | >100 | 2.04 | >100 |
| E23 | >100 | 3.28 | >100 |
| E24 | >100 | 3.24 | >100 |
| E25 | >100 | 3.02 | >100 |
| E26 | 87.3 | 0.03 | 7.09 |
| E27 | >100 | 0.75 | 14.8 |
| E28 | >100 | 0.60 | >100 |
| E29 | 4.09 | 0.10 | 0.50 |
| E30 | 3.67 | 0.14 | 0.82 |
| E31 | 40.1 | 0.40 | 8.12 |
| E32 | 51.8 | 0.29 | 33.0 |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step that is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A compound of Formula (I), or a pharmaceutically acceptable salt thereof:

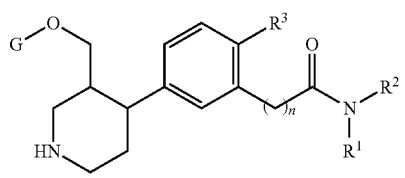

wherein:

G is

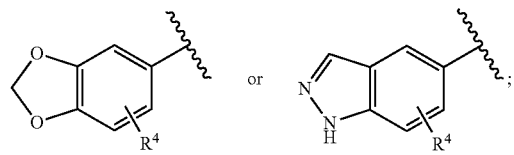

n is 0, 1, or 2;

$R^1$ is H, $C_{1-8}$alkyl, $C_{2-8}$alkenyl, $C_{3-8}$ cycloalkyl, $C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;

$R^2$ is $C_{1-8}$alkyl, $C_{2-8}$alkenyl, $C_{0-4}$alkylene-$C_{3-8}$ cycloalkyl, $C_{0-4}$alkylene-$C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;

$R^3$ is H, F, Cl, $CF_3$, $CHF_2$, $CH_2F$, or $CH_3$; and $R^4$ is H, F, or Cl.

2. The compound of claim 1, wherein $R^1$ is:

(a) H or; (b) $C_{1-8}$alkyl or $C_{2-8}$alkenyl.

3. The compound of claim 1, wherein $R^2$ is:

(a) $C_{1-8}$ alkyl; or (b) $C_{0-4}$alkylene-$C_{3-8}$ cycloalkyl or $C_{0-4}$alkylene-$C_{3-5}$ cycloalkenyl; or (c) $C_{1-4}$ alkylene-aryl or $C_{1-4}$ alkylene-heteroaryl.

4. The compound of claim 1, wherein $R^2$ is:

(a)

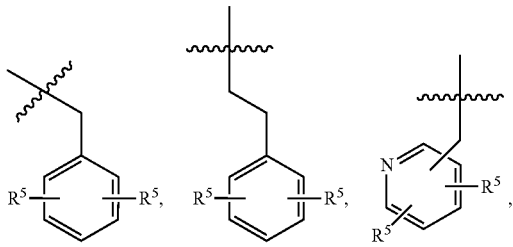

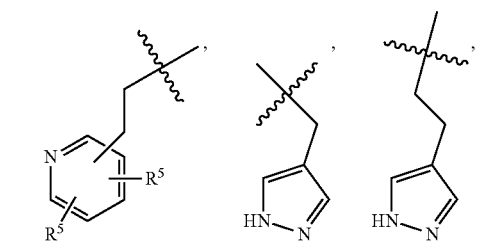

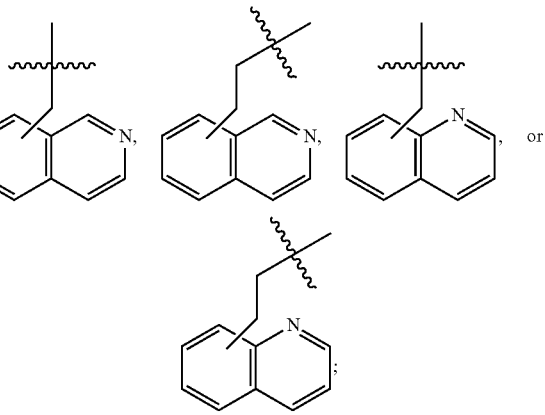

wherein each $R^5$ independently is H, halo, $C_{1-4}$ alkyl, or $C_{1-4}$ alkoxyl; or (b)

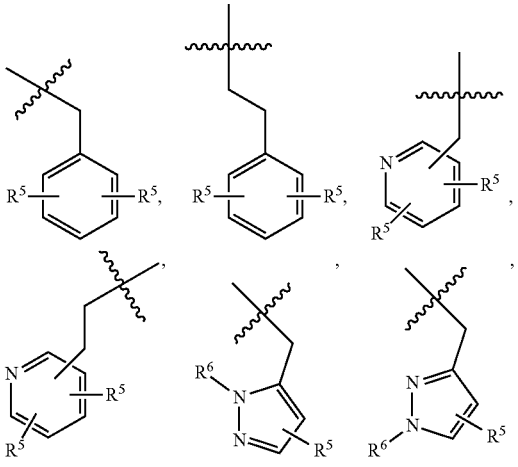

-continued

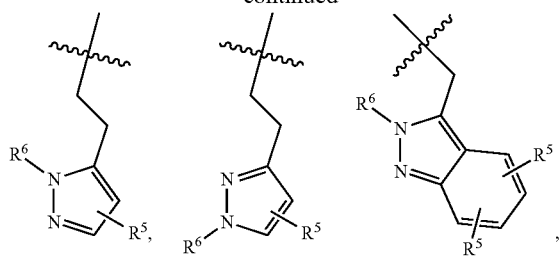

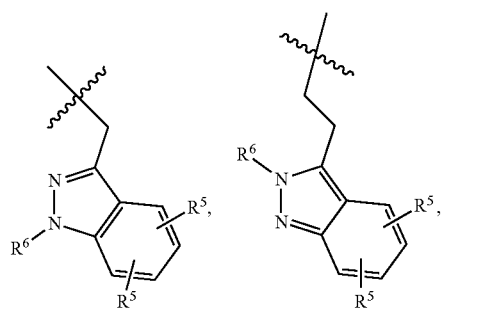

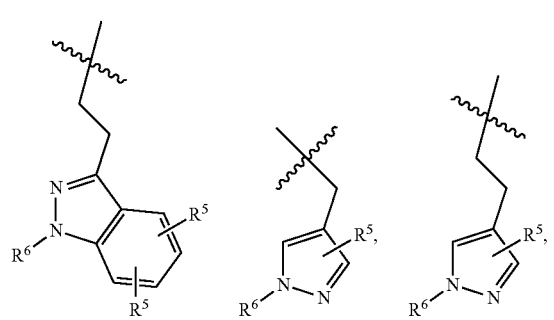

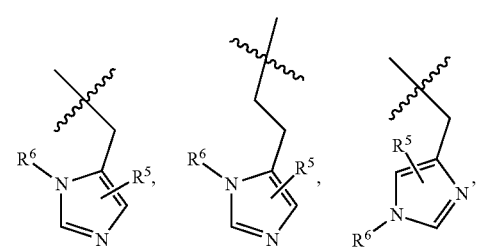

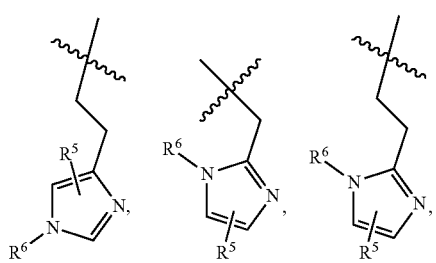

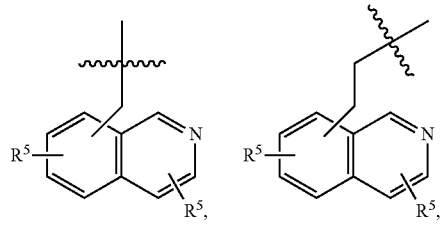

-continued

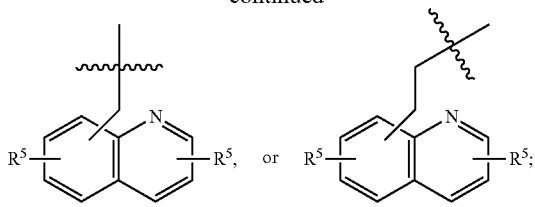

wherein each $R^5$ independently is H, halo, $C_{1-4}$ alkyl, or $C_{1-4}$ alkoxyl; and $R^6$ is H or $C_{1-5}$ alkyl; or (c)

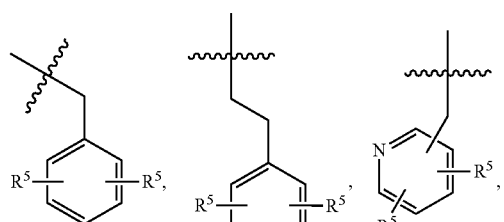

wherein each $R^5$ independently is H, halo, $C_{1-4}$ alkyl, or $C_{1-4}$ alkoxyl; and $R^6$ is H or $C_{1-5}$ alkyl.

5. The compound of claim 4, wherein:
(a) each $R^5$ is H; or
(b) one $R^5$ is H and one $R^5$ is selected from the group consisting of halo, $C_{1-4}$ alkyl, and $C_{1-4}$ alkoxyl; or
(c) one $R^5$ is H and one $R^5$ is F or Cl; or
(d) one $R^5$ is H and one $R^5$ is $CH_3$ or $CF_3$; or
(e) one $R^5$ is H and one $R^5$ is $OCH_3$ or $OCF_3$; or
(f) each $R^5$ is halo, $C_{1-4}$ alkyl, or $C_{1-4}$ alkoxyl; or
(g) each $R^5$ is F or Cl; or
(h) each $R^5$ is $C_{1-4}$ alkyl; or
(i) each $R^5$ independently is $CH_3$ or $CF_3$; or
(j) each $R^5$ is $C_{1-4}$ alkoxyl; or
(k) each $R^5$ independently is $OCH_3$ or $OCF_3$.

6. The compound of claim 4, wherein each $R^5$ is ortho.

7. The compound of claim 4, wherein $R^6$ is:
(a) H; or
(b) $C_{1-5}$ alkyl; or
(c) $NHC_{1-5}$ alkyl or $N(C_{1-5}$ alkyl$)_2$; or
(d) $NCH_3$.

8. The compound of claim 1, wherein $R^2$ is:
(a)
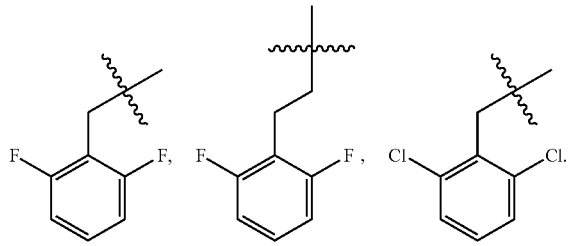
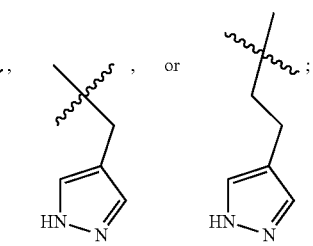
or
(b)
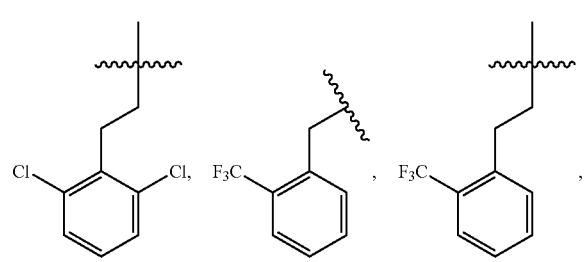
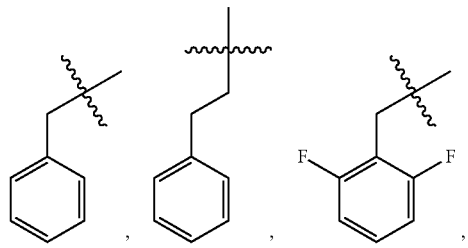
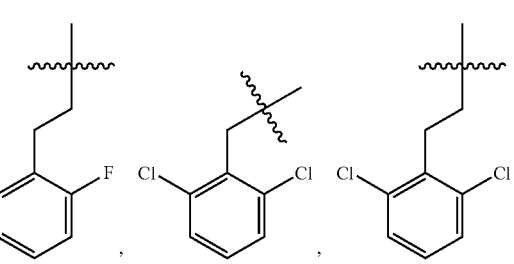
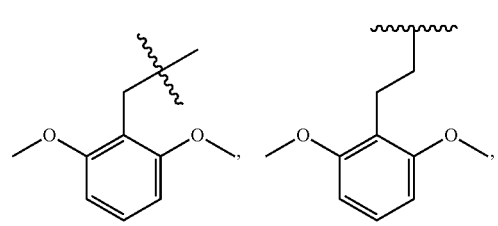
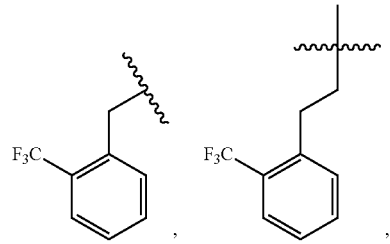
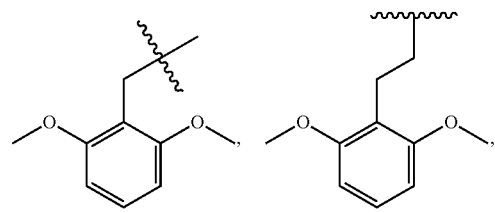
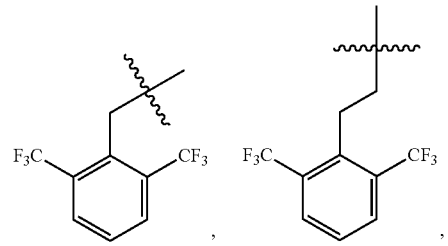
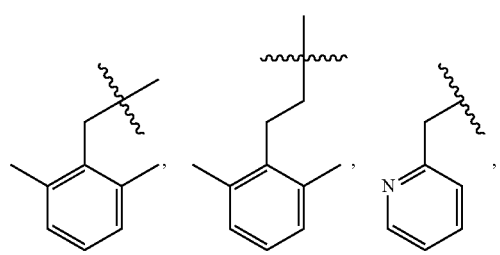
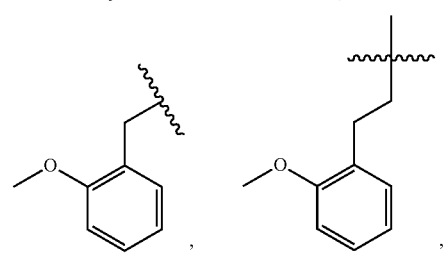

-continued

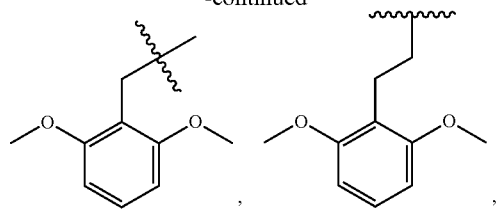

9. The compound of claim 1, wherein R³ is:
(a) H or Cl; or
(b) CF₃, CHF₂, CH₂F, or CH₃; or
(c) F.

10. The compound of claim 1, wherein R⁴ is:
(a) H; or
(b) Cl or
(c) F.

11. The compound of claim 1, wherein G is

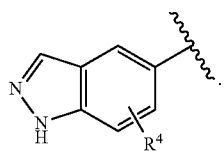

12. The compound of claim 1, wherein G is

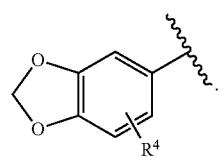

13. The compound of claim 1, having a structure of Formula (IA'):

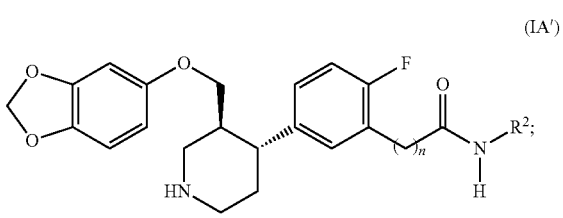
(IA')

wherein
n is 0 or 1; and
R² is $C_{1-2}$ alkylene-aryl or $C_{1-2}$ alkylene-heteroaryl;
or a pharmaceutically acceptable salt thereof.

14. A compound selected from the group consisting of:

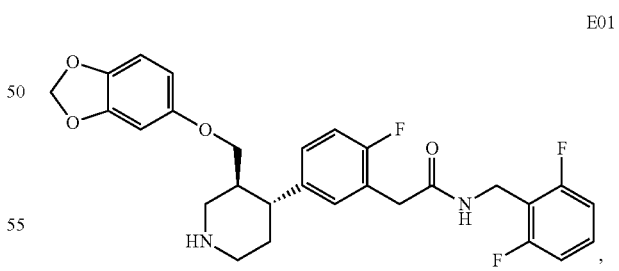
E01

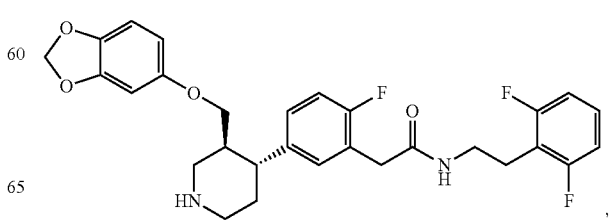
E02

E03
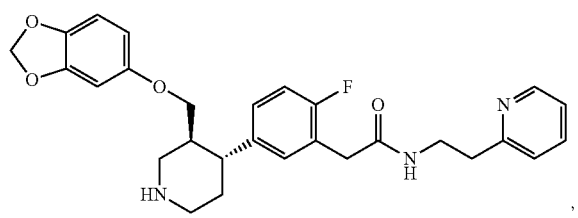
,
E04
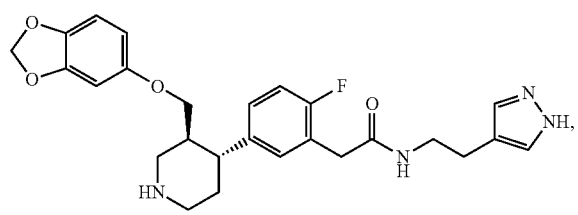
,
E05
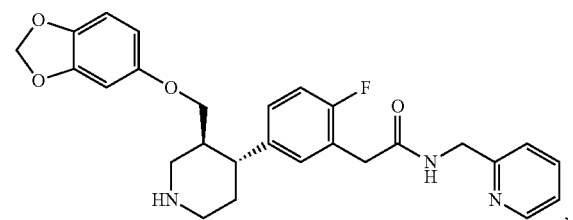
,
E06
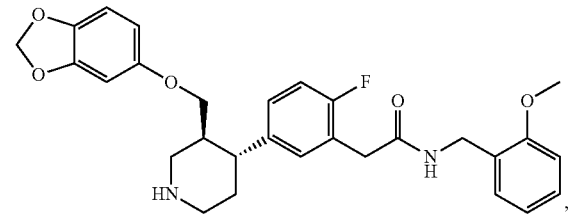
,
E07
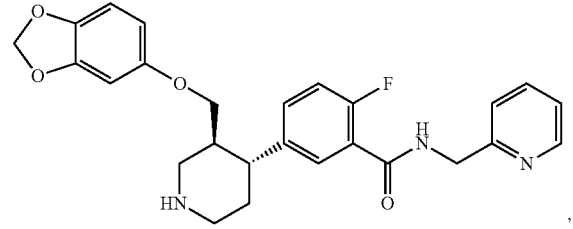
,
E08
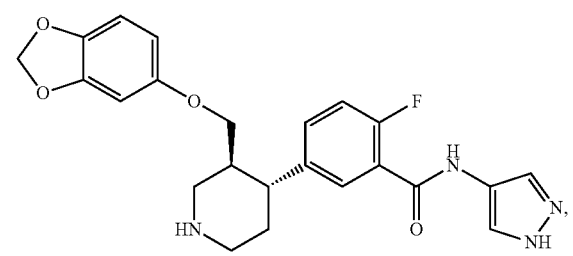
,
E09
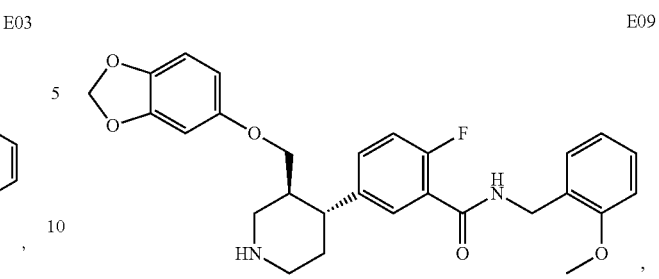
,
E10
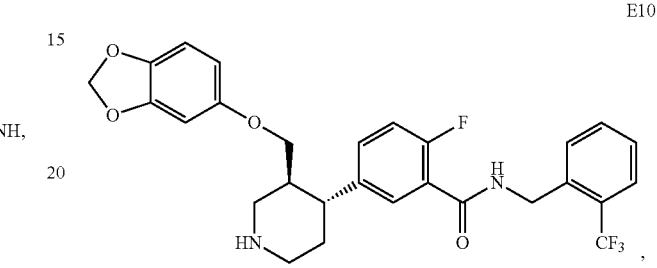
,
E11
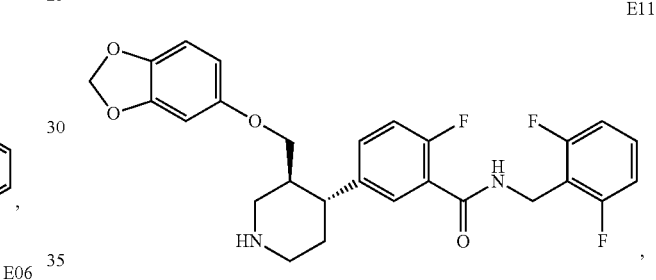
,
E12
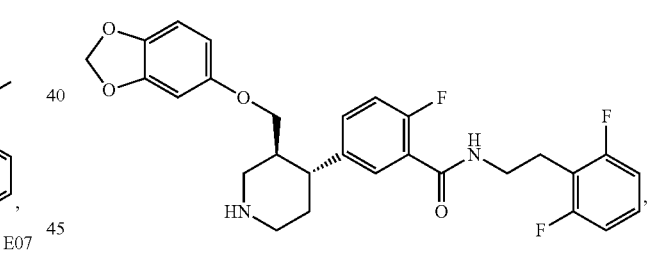
,
E13
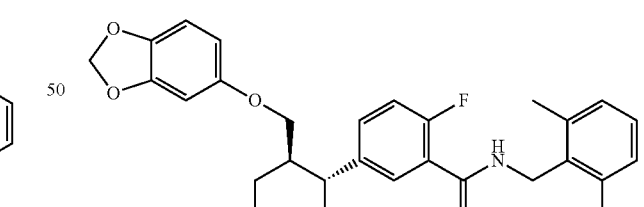
,
E14
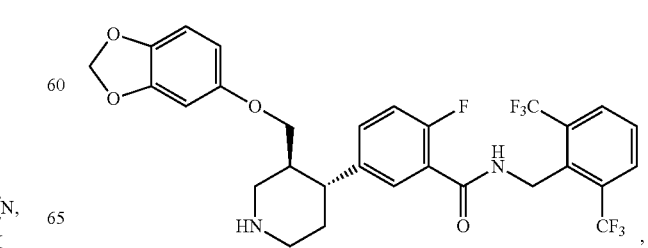
, E15
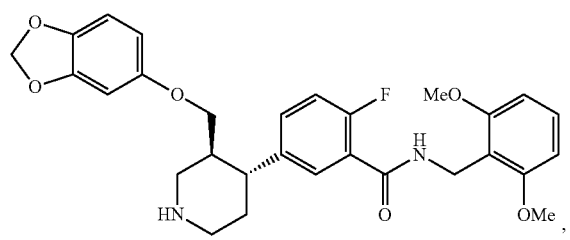,
E16
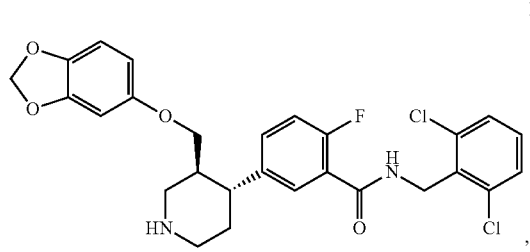,
E17
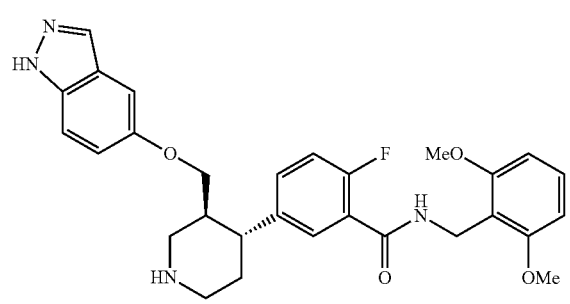,
E18
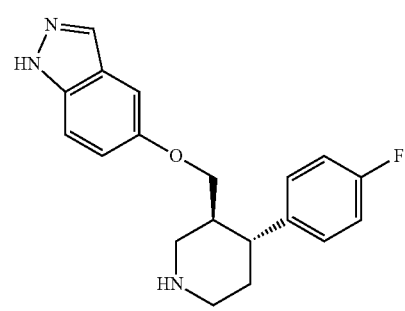
E19
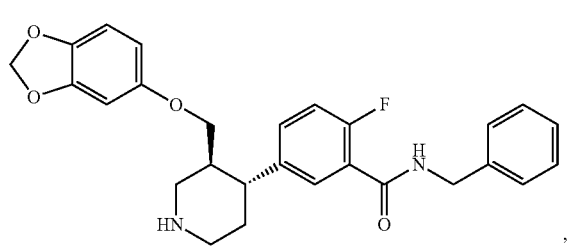,
E20
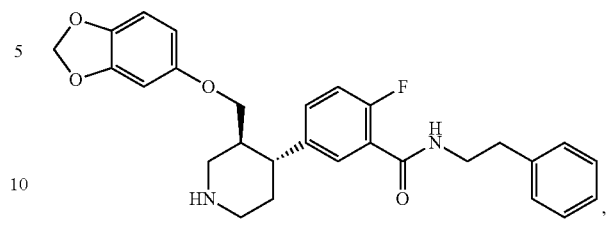,
E21
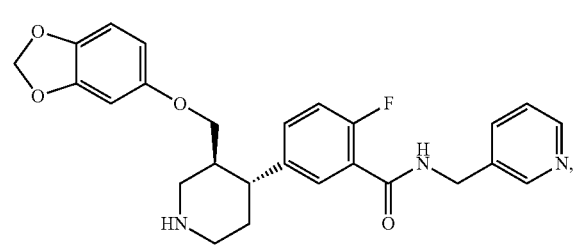,
E22
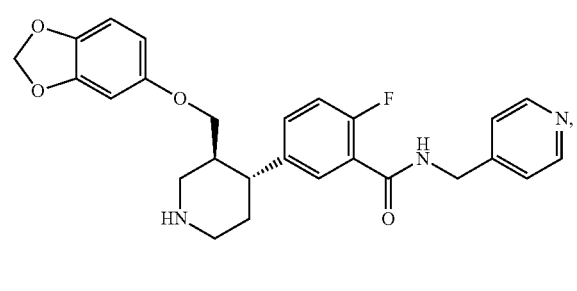,
E23
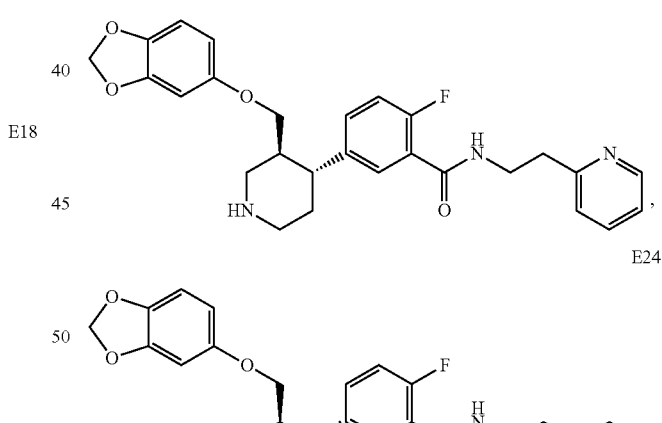,
E24
E25
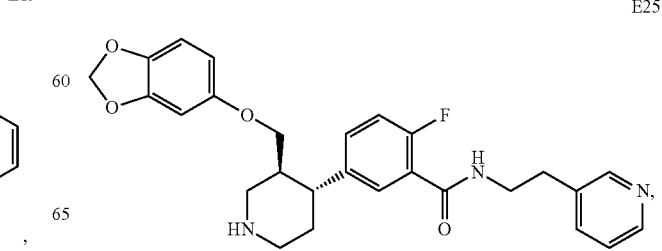, 101
-continued
E26
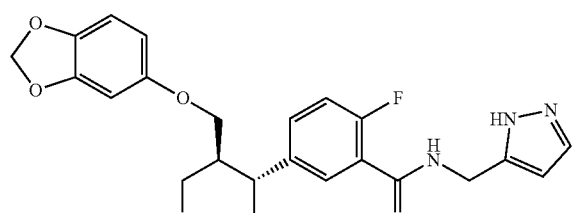
E27
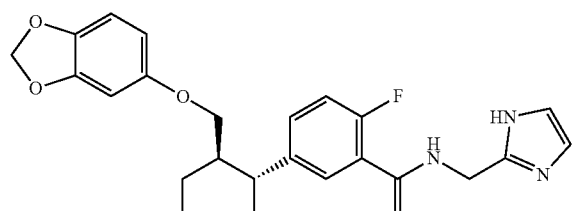
E28
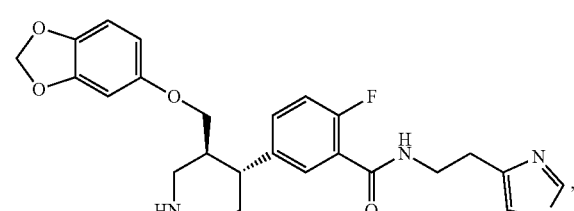
E29
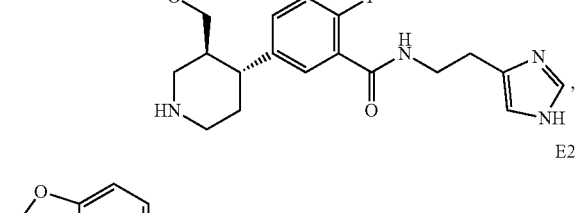
E30
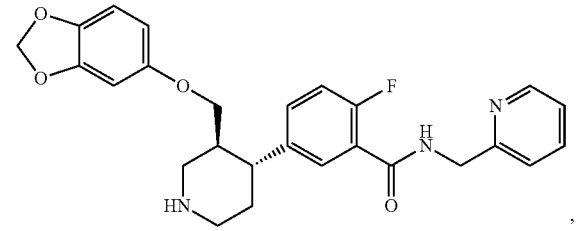
E31
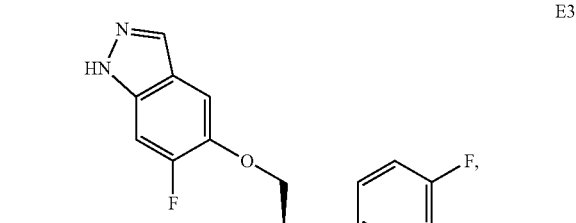, and
102
-continued
E32
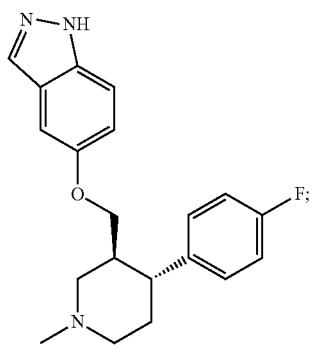
or a pharmaceutically acceptable salt thereof.
15. A pharmaceutical formulation comprising the compound of claim 1, or a compound selected from the group consisting of E01-E32, or a pharmaceutically acceptable salt thereof, and a pharmaceutically acceptable excipient, wherein E01-E32 have structures as shown below:
(E01)
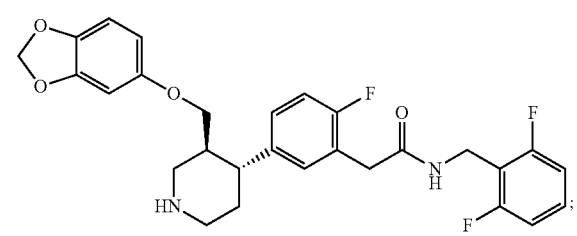
(E02)
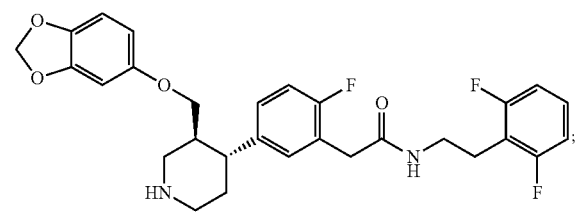
(E03)
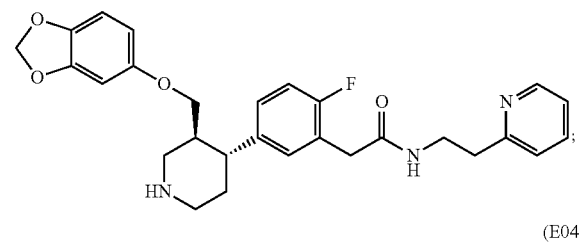
(E04)
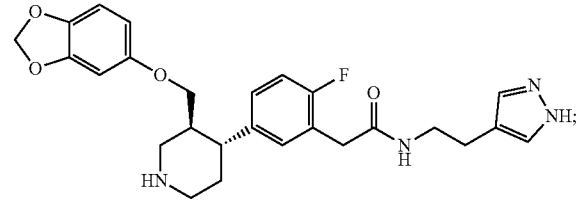

(E05)
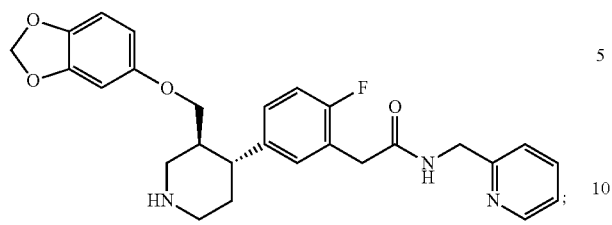
(E06)
(E07)
(E08)
(E09)
(E10)
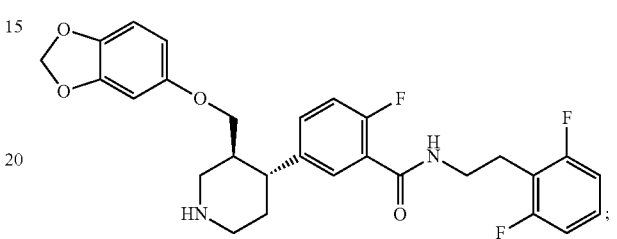
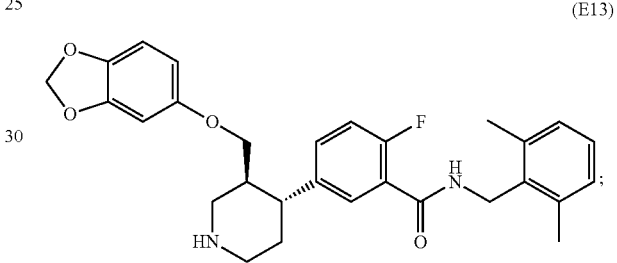
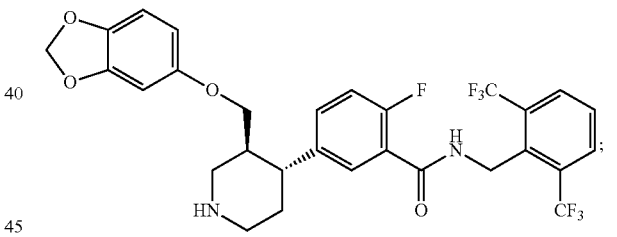
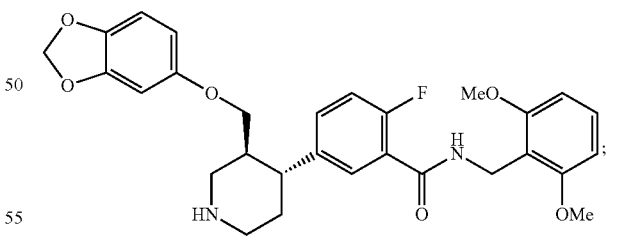
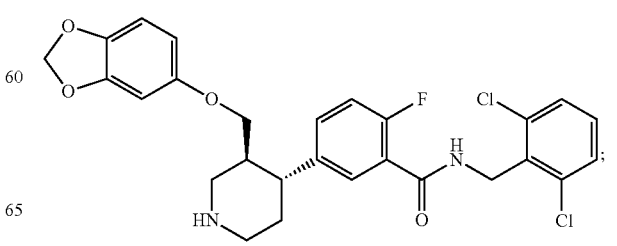
(E11)
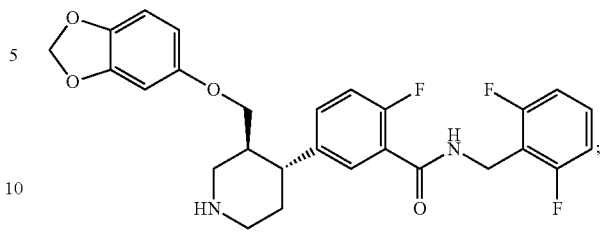
(E12)
(E13)
(E14)
(E15)
(E16)
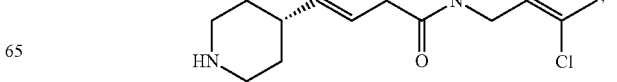

(E17)
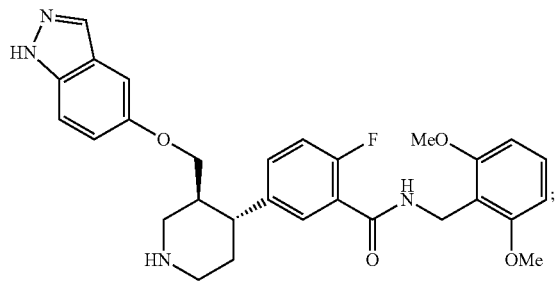
(E18)
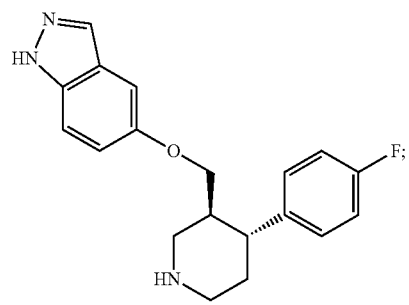
(E19)
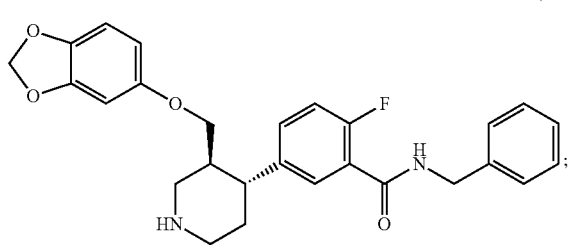
(E20)
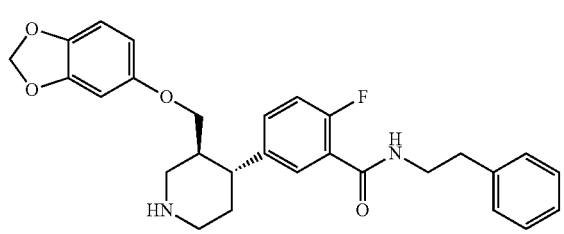
(E21)
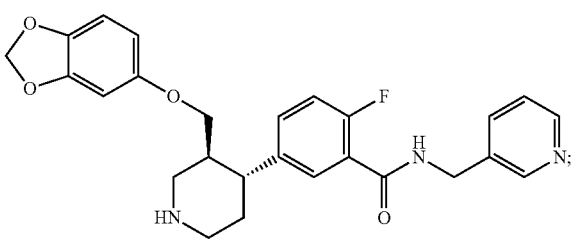
(E22)
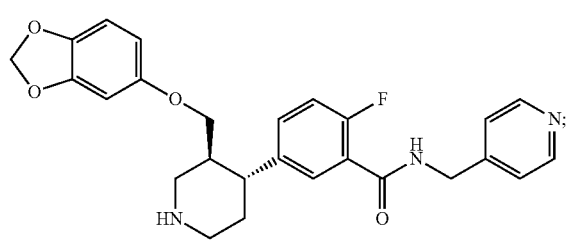
(E23)
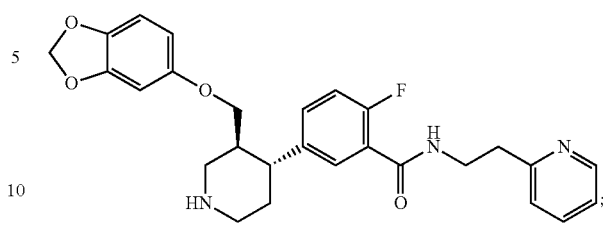
(E24)
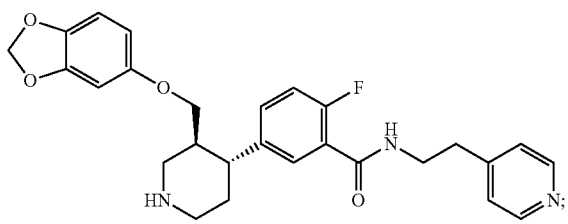
(E25)
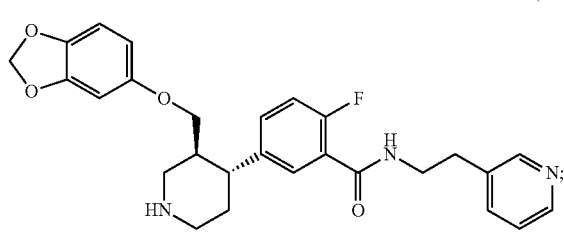
(E26)
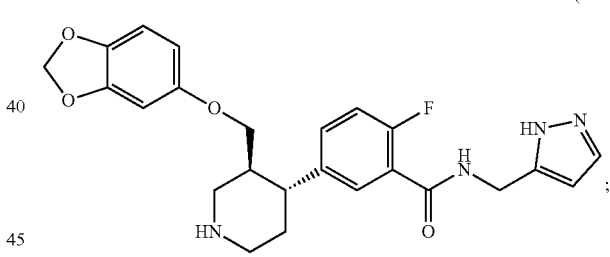
(E27)
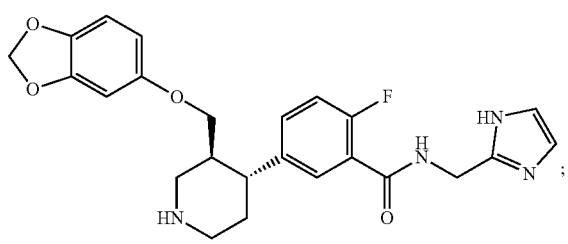
(E28)

wherein E01-E32 have structures as shown below:
(E29)
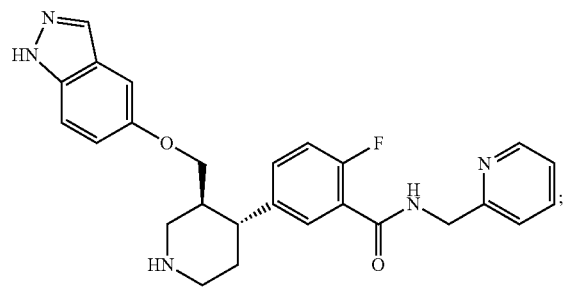
(E01)
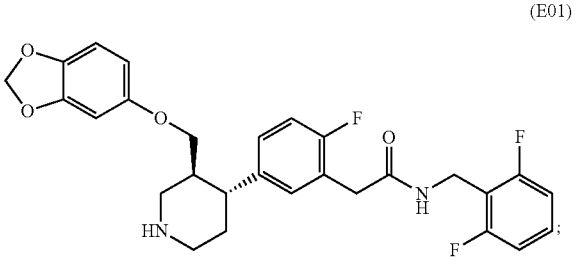
(E30)
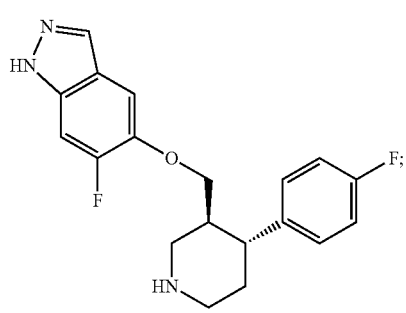
(E02)
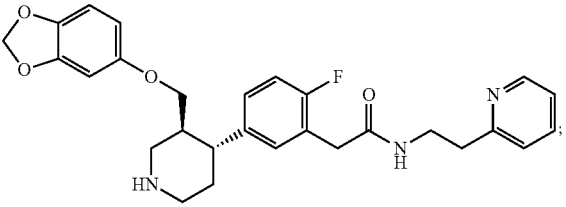
(E03)
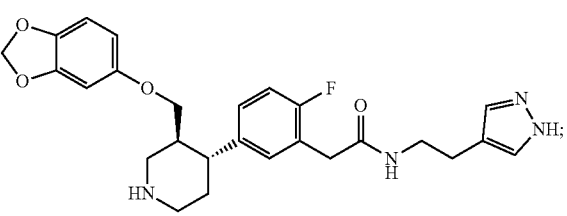
(E31)
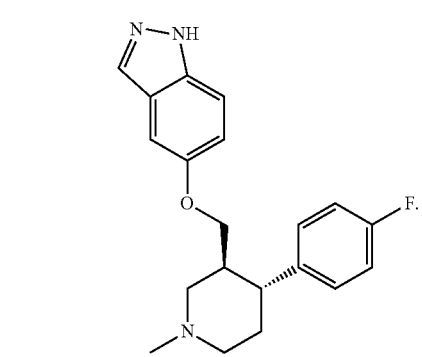
(E04)
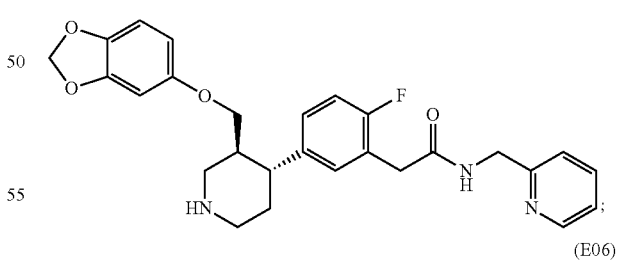
(E32)
(E05)
(E06)
16. A method of inhibiting GRK2, GRK5, or both in a cell, comprising contacting the cell with the compound of claim 1 or a compound selected from the group consisting of E01-E32, or a pharmaceutically acceptable salt thereof, in an amount effective to inhibit GRK2, GRK5, or both;

-continued
(E07)
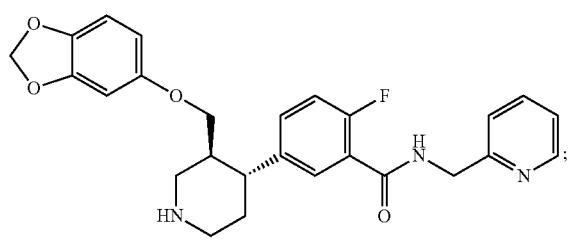
(E08)
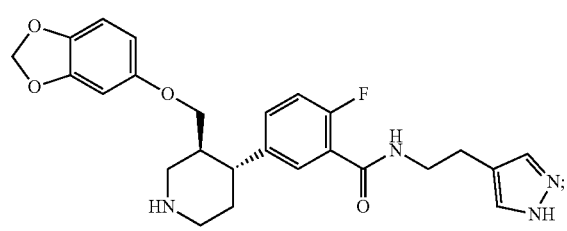
(E09)
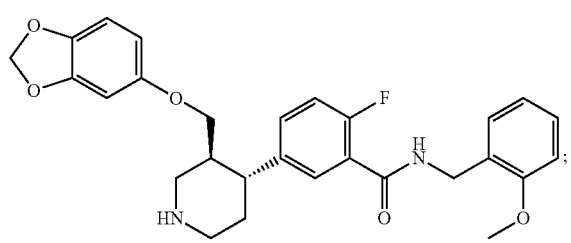
(E10)
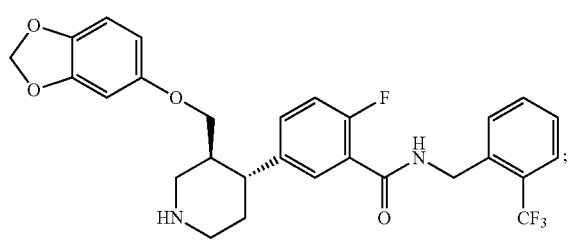
(E11)
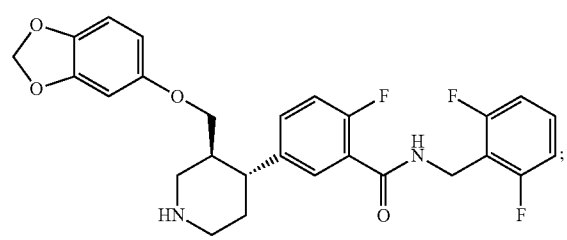
(E12)
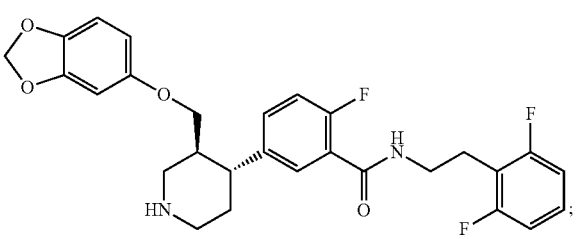
-continued
(E13)
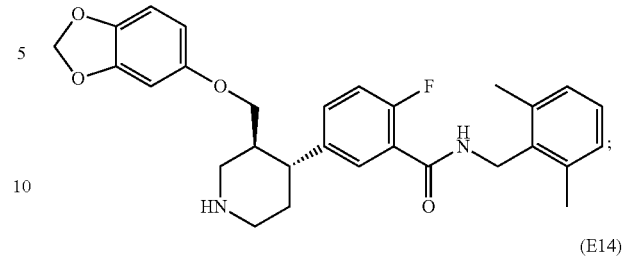
(E14)
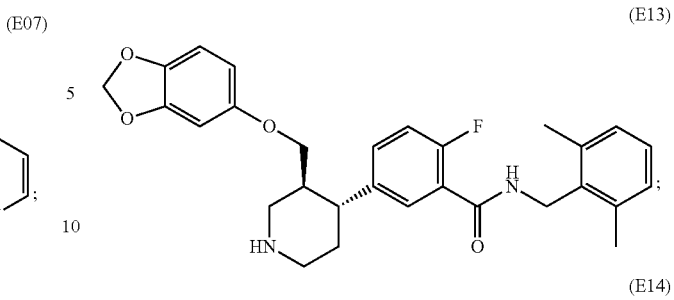
(E15)
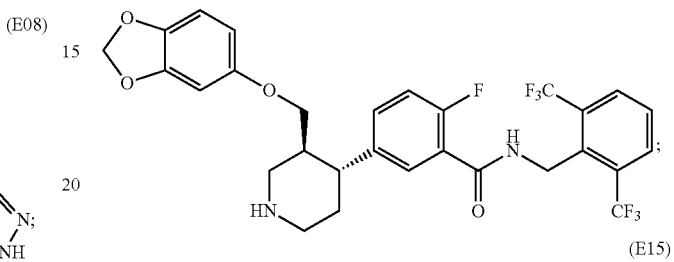
(E16)
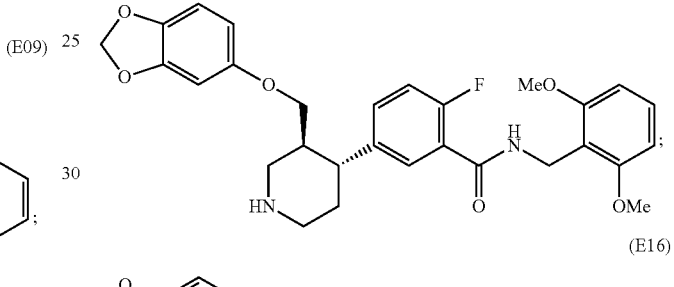
(E17)
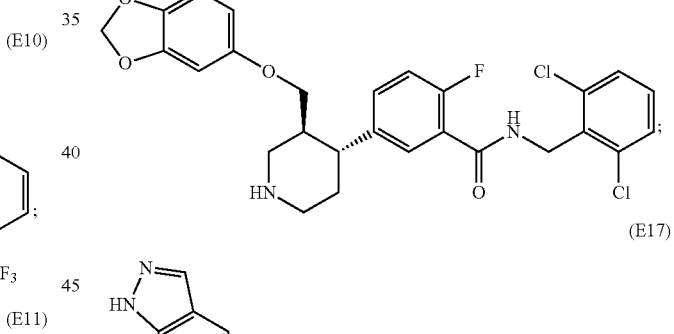
(E18)
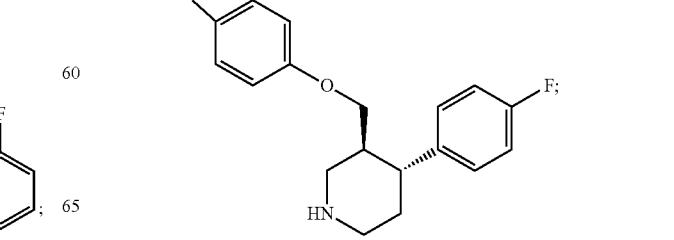

(E19)
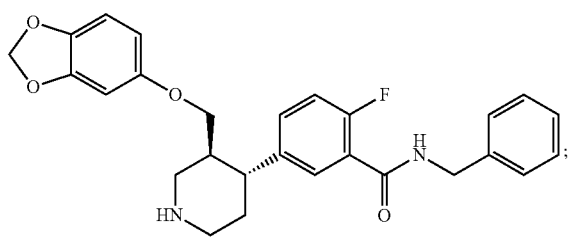
(E20)
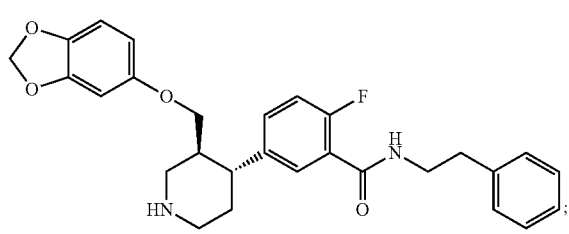
(E21)
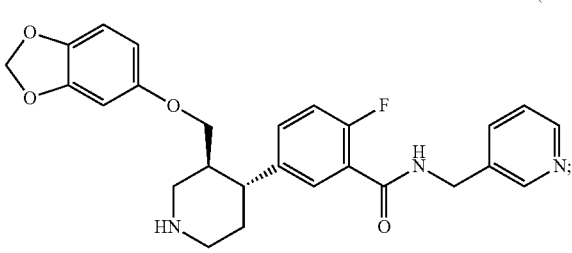
(E22)
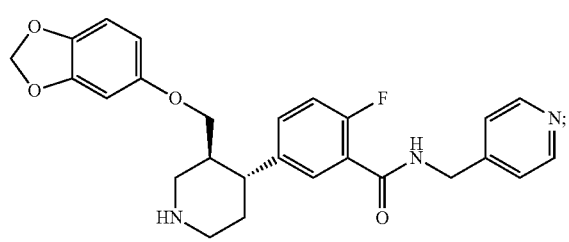
(E23)
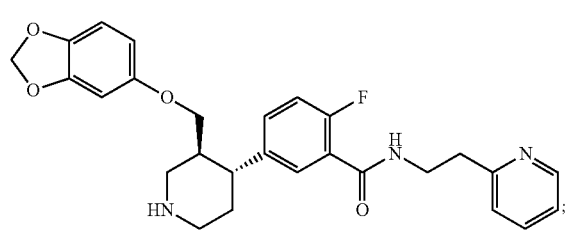
(E24)
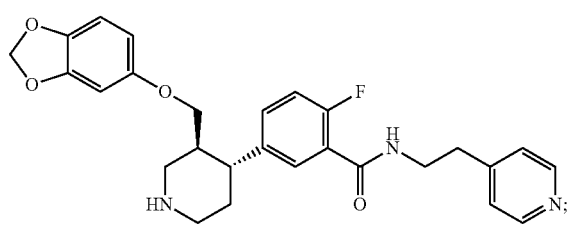
(E25)
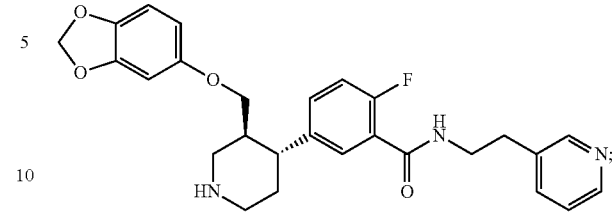
(E26)
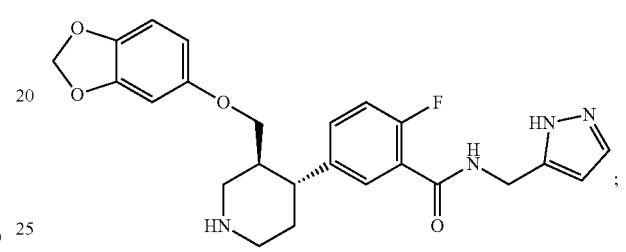
(E27)
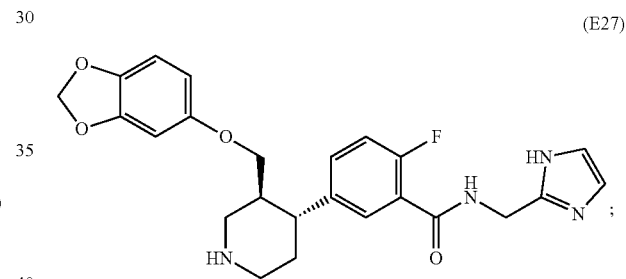
(E28)
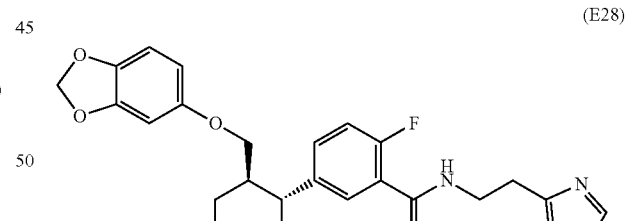
(E29)
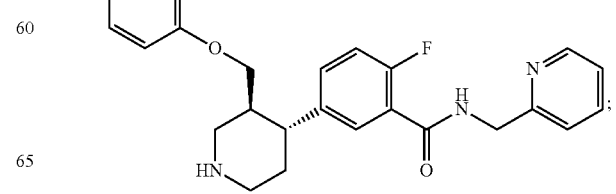

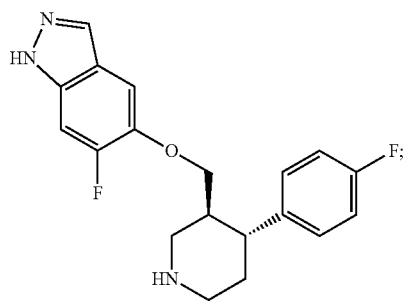

(E30)

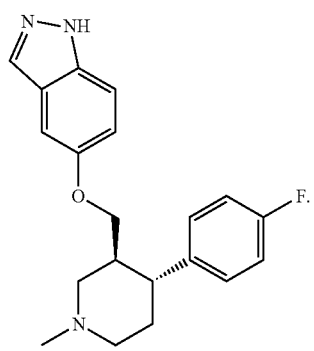

(E32)

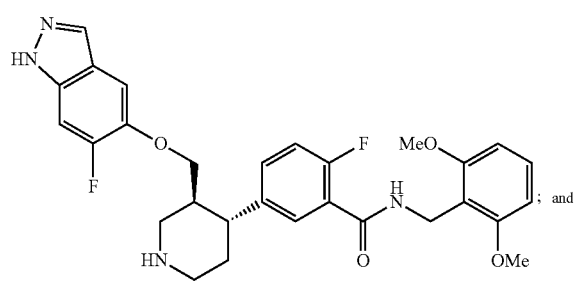

(E31)

; and

17. The method of claim 16, wherein the compound exhibits an $IC_{50}$ of less than about 100 μM for GRK2 or GRK5.

18. The method of claim 16, wherein the cell is a myocyte.

19. A method of treating heart disease in a subject comprising administering to the subject a therapeutically effective amount of the pharmaceutical formulation of claim 15.

20. The method of claim 19, wherein the heart disease is cardiac failure, cardiac hypertrophy, hypertension, or a combination thereof.

* * * * *

UNITED STATES PATENT AND TRADEMARK OFFICE
CERTIFICATE OF CORRECTION

PATENT NO. : 10,329,283 B2  
APPLICATION NO. : 15/738606  
DATED : June 25, 2019  
INVENTOR(S) : Scott D. Larsen et al.

Page 1 of 1

It is certified that error appears in the above-identified patent and that said Letters Patent is hereby corrected as shown below:

In the Claims

At Column 101, in structure "E29", " 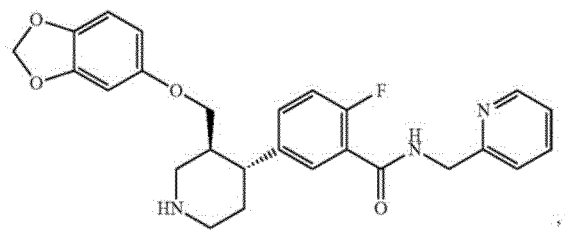 " should be 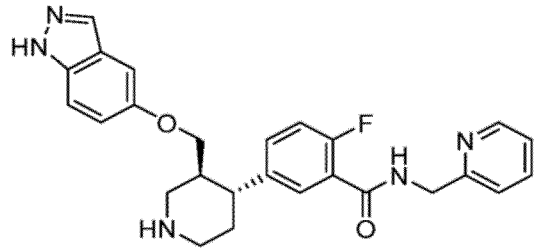

-- --.

Signed and Sealed this  
Fourteenth Day of January, 2020

Andrei Iancu  
*Director of the United States Patent and Trademark Office*